(12) United States Patent
Deng et al.

(10) Patent No.: US 10,073,087 B2
(45) Date of Patent: Sep. 11, 2018

(54) BIOPOLYMER-MEDIATED ASSEMBLY OF NANOPARTICLES USING GENETICALLY ENCODED PROTEINS

(71) Applicant: Massachusetts Institute of Technology, Cambridge, MA (US)

(72) Inventors: Zhengtao Deng, Cambridge, MA (US); Timothy Kuan-Ta Lu, Charlestown, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 297 days.

(21) Appl. No.: 14/597,575

(22) Filed: Jan. 15, 2015

(65) Prior Publication Data

US 2016/0238591 A1    Aug. 18, 2016

Related U.S. Application Data

(60) Provisional application No. 62/045,192, filed on Sep. 3, 2014, provisional application No. 61/927,924, filed on Jan. 15, 2014.

(51) Int. Cl.
*G01N 33/52* (2006.01)
*A61K 49/00* (2006.01)

(52) U.S. Cl.
CPC ....... *G01N 33/521* (2013.01); *A61K 49/0093* (2013.01)

(58) Field of Classification Search
None
See application file for complete search history.

(56) References Cited

FOREIGN PATENT DOCUMENTS

WO    WO2012/166906    * 12/2012
WO    WO 2012/166906    12/2012

OTHER PUBLICATIONS

Veggiani et al. (Trends in Biotechnology, 2014 pp. 1-7).*
Abe et al. (Bio conjugate Chem 2013, 24, 2342-250).*
Blum et al., Templated self-assembly of quantum dots from aqueous solution using protein scaffolds. Nanotechnology. 2006;17(20):5073-5079.
Boeneman et al., Optimizing protein coordination to quantum dots with designer peptidyl linkers. Bioconjug Chem. Feb. 20, 2013;24(2):269-81. doi: 10.1021/bc300644p. Epub Feb. 4, 2013.
Boeneman et al., Peptide linkers for the assembly of semiconductor quantum dot bioconjugates. SPIE. 2009;7189. 9 pages.
Chen et al., Synthesis and patterning of tunable multiscale materials with engineered cells. Nat Mater. May 2014;13(5):515-23. doi: 10.1038/nmat3912. Epub Mar. 23, 2014.
Liu et al., Compact cysteine-coated CdSe(ZnCdS) quantum dots for in vivo applications. J Am Chem Soc. Nov. 28, 2007;129(47):14530-1. Epub Nov. 6, 2007.
Zakeri et al., Peptide tag forming a rapid covalent bond to a protein, through engineering a bacterial adhesin. Proc Natl Acad Sci U S A. Mar. 20, 2012;109(12):E690-7. doi: 10.1073/pnas.1115485109. Epub Feb. 24, 2012.
Alivisatos et al., Organization of 'nanocrystal molecules' using DNA. Nature. Aug. 15, 1996;382(6592):609-11.
Bakalova et al., Quantum dots as photosensitizers? Nat Biotechnol. Nov. 2004;22(11):1360-1.
Barnhart et al., Curli biogenesis and function. Annu Rev Microbiol. 2006;60:131-47.
Bui et al., Programmable periodicity of quantum dot arrays with DNA origami nanotubes. Nano Lett. Sep. 8, 2010;10(9):3367-72. doi: 10.1021/nl101079u.
Callura et al., Genetic switchboard for synthetic biology applications. Proc Natl Acad Sci U S A. Apr. 10, 2012;109(15):5850-5. doi:10.1073/pnas.1203808109.
Chapman et al., Role of *Escherichia coli* curli operons in directing amyloid fiber formation. Science. Feb. 1, 2002;295(5556):851-5.
Darwin et al., Molecular basis of the interaction of *Salmonella* with the intestinal mucosa. Clin Microbiol Rev. Jul. 1999;12(3):405-28.
Deng et al., DNA functionalization of colloidal II-VI semiconductor nanowires for multiplex nanoheterostructures. Chem. Sci. 4, 2234-2240 (2013).
Deng et al., Robust DNA-functionalized core/shell quantum dots with fluorescent emission spanning from UV-vis to near-IR and compatible with DNA-directed self-assembly. J Am Chem Soc. Oct. 24, 2012;134(42):17424-7. doi: 10.1021/ja3081023.
Dong et al., Optical trapping with high forces reveals unexpected behaviors of prion fibrils. Nat Struct Mol Biol. Dec. 2010;17(12):1422-30. doi: 10.1038/nsmb.1954.
Dueholm et al., Functional amyloid in Pseudomonas. Mol Microbiol. Aug. 2010;77(4):1009-20. doi:10.1111/j.1365-2958.2010.07269.x.
Epstein et al., Spatial clustering of the curlin secretion lipoprotein requires curli fiber assembly. J Bacteriol. Jan. 2009;191(2):608-15. doi: 10.1128/JB.01244-08.
King et al., Computational design of self-assembling protein nanomaterials with atomic level accuracy. Science. Jun. 1, 2012;336(6085):1171-4. doi:10.1126/science.1219364.
Lutz et al., Independent and tight regulation of transcriptional units in *Escherichia coli* via the LacR/O, the TetR/O and AraC/I1-I2 regulatory elements. Nucleic Acids Res. Mar. 15, 1997;25(6):1203-10.
Michalet et al., Quantum dots for live cells, in vivo imaging, and diagnostics. Science. Jan. 28, 2005;307(5709):538-44.

(Continued)

*Primary Examiner* — James H Alstrum-Acevedo
*Assistant Examiner* — Tara L Martinez
(74) *Attorney, Agent, or Firm* — Wolf, Greenfield & Sacks, P.C.

(57) ABSTRACT

Various aspects and embodiments provided herein are directed to compositions that include at least one nanoparticle linked to a first polypeptide, and a biologically synthesizable polymer linked to at least one second polypeptide that binds covalently to the first polypeptide. Other aspects and embodiments provided herein are directed to methods of producing the foregoing compositions and components therein.

16 Claims, 18 Drawing Sheets

Specification includes a Sequence Listing.

(56) References Cited

OTHER PUBLICATIONS

Nenninger et al., Localized and efficient curli nucleation requires the chaperone-like amyloid assembly protein CsgF. Proc Natl Acad Sci U S A. Jan. 20, 2009;106(3):900-5. doi: 10.1073/pnas.0812143106.
Otoo et al., Candida albicans Als adhesins have conserved amyloid-forming sequences. Eukaryot Cell. May 2008;7(5):776-82.
Payne et al., Temporal control of self-organized pattern formation without morphogen gradients in bacteria. Mol Syst Biol. Oct. 8, 2013;9:697. doi: 10.1038/msb.2013.55.
Pinheiro et al., Challenges and opportunities for structural DNA nanotechnology. Nat Nanotechnol. Nov 6, 2011;6(12):763-72. doi:10.1038/nnano.2011.187.
Prigent-Combaret et al., Complex regulatory network controls initial adhesion and biofilm formation in *Escherichia coli* via regulation of the csgD gene. J Bacteriol. Dec. 2001;183(24):7213-23.
Ramsook et al., Yeast cell adhesion molecules have functional amyloid-forming sequences. Eukaryot Cell. Mar. 2010;9(3):393-404. doi: 10.1128/EC.00068-09.
Romero et al., Amyloid fibers provide structural integrity to Bacillus subtilis biofilms. Proc Natl Acad Sci U S A. Feb. 2, 2010;107(5):2230-4. doi: 10.1073/pnas.0910560107.
Sapsford et al., Functionalizing nanoparticles with biological molecules: developing chemistries that facilitate nanotechnology. Chem Rev. Mar. 13, 2013;113(3):1904-2074. doi: 10.1021/cr300143v.
Scheibel et al., Conducting nanowires built by controlled self-assembly of amyloid fibers and selective metal deposition. Proc Natl Acad Sci U S A. Apr. 15, 2003;100(8):4527-32.
Sharma et al., Control of self-assembly of DNA tubules through integration of gold nanoparticles. Science. Jan. 2, 2009;323(5910):112-6. doi: 10.1126/science.1165831.
Shewmaker et al., The functional curli amyloid is not based on in-register parallel beta-sheet structure. J Biol Chem. Sep. 11, 2009;284(37):25065-76. doi: 0.1074/jbc.M109.007054.
Smith et al., Characterization of the nanoscale properties of individual amyloid fibrils. Proc Natl Acad Sci U S A. Oct. 24, 2006;103(43):15806-11.
Smith et al., Tuning the optical and electronic properties of colloidal nanocrystals by lattice strain. Nat Nanotechnol. Jan. 2009;4(1):56-63. doi: 10.1038/nnano.2008.360.
Teertstra et al., The filament-specific Rep1-1 repellent of the phytopathogen Ustilago maydis forms functional surface-active amyloid-like fibrils. J Biol Chem. Apr. 3, 2009;284(14):9153-9. doi:10.1074/jbc.M900095200.
Zakeri et al., Peptide tag forming a rapid covalent bond to a protein, through engineering a bacterial adhesin. Proc Natl Acad Sci U S A. Mar. 20, 2012;109(12):E690-7. doi: 10.1073/pnas.1115485109.
Bakalova et al., Designing quantum-dot probes. Nature Photonics 1. 2007;487-489 doi: 10.1038/nphoton.2007.150.
Blum et al., Electronic properties of molecular memory circuits on a nanoscale scaffold. IEEE Trans Nanobioscience. Dec. 2007;6(4):270-4.
Braun et al., DNA-templated assembly and electrode attachment of a conducting silver wire. Nature. Feb. 19, 1998;391(6669):775-8.
Bruchez et al., Semiconductor nanocrystals as fluorescent biological labels. Science. Sep. 25, 1998;281(5385):2013-6.
Calvaresi et al., The devil and holy water: protein and carbon nanotube hybrids. Acc Chem Res. Nov. 19, 2013;46(11):2454-63. doi: 10.1021/ar300347d.
Chan et al., Quantum dot bioconjugates for ultrasensitive nonisotopic detection. Science. Sep. 25, 1998;281(5385):2016-8.
Chen et al., Synthesis and patterning of tunable multiscale materials with engineered cells. Nature Materials. 2014;13:515-523.
Choi et al., From artificial atoms to nanocrystal molecules: preparation and properties of more complex nanostructures. Annu Rev Phys Chem. 2010;61:369-89. doi:10.1146/annurev.physchem.012809.103311.
Dabbousi et al., (CdSe)ZnS Core—Shell Quantum Dots: Synthesis and Characterization of a Size Series of Highly Luminescent Nanocrystallites. J. Phys. Chem. B. 1997;101(46):9463-9475. DOI: 10.1021/jp971091y.

De Mello Donegá, Synthesis and properties of colloidal heteronanocrystals. Chem Soc Rev. Mar. 2011;40(3):1512-46. doi: 10.1039/c0cs00055h.
Deng et al., Aqueous synthesis of zinc blende CdTe/CdS magic-core/thick-shell tetrahedral-shaped nanocrystals with emission tunable to near-infrared. J Am Chem Soc. Apr. 28, 2010;132(16):5592-3. doi: 10.1021/ja101476b.
Deng et al., Solution synthesis of ultrathin single-crystalline SnS nanoribbons for photodetectors via phase transition and surface processing. ACS Nano. Jul. 24, 2012;6(7):6197-207. doi: 10.1021/nn302504p.
Djalali et al., Au nanowire fabrication from sequenced histidine-rich peptide. J Am Chem Soc. Nov. 20, 2002;124(46):13660-1.
Fletcher et al., Self-assembling cages from coiled-coil peptide modules. Science. May 3, 2013;340(6132):595-9. doi: 10.1126/science.1233936.
Fu et al., Assemblies of Metal Nanoparticles and Self-Assembled Peptide Fibrils—Formation of Double Helical and Single-Chain Arrays of Metal Nanoparticles. Adv. Mater., 2003;15: 902-906. doi:10.1002/adma.200304624.
Fu et al., Discrete nanostructures of quantum dots/Au with DNA. J Am Chem Soc. Sep. 8, 2004;126(35):10832-3.
Gao et al., Self-orienting nanocubes for the assembly of plasmonic nanojunctions. Nat Nanotechnol. Jun. 10, 2012;7(7):433-7. doi:10.1038/nnano.2012.83.
Groschel et al., Guided hierarchical co-assembly of soft patchy nanoparticles. Nature. Nov. 14, 2013;503(7475):247-51. doi: 10.1038/nature12610. Methods.
Gubeli et al., Synthetic biology for mammalian cell technology and materials sciences. Biotechnol Adv. Jan.-Feb. 2013;31(1):68-78. doi:10.1016/j.biotechadv.2012.01.007.
Hung et al., Large-area spatially ordered arrays of gold nanoparticles directed by lithographically confined DNA origami. Nat Nanotechnol. Feb. 2010;5(2):121-6. doi:10.1038/nnano.2009.450.
Juarez et al., Quantum Dot Attachment and Morphology Control by Carbon Nanotubes. Nano Lett. 2007;7(12):3564-3568. DOI: 10.1021/nl071225b.
Knowles et al., Nanomechanics of functional and pathological amyloid materials. Nat Nanotechnol. Jul. 31, 2011;6(8):469-79. doi: 10.1038/nnano.2011.102.
Kostiainen et al., Electrostatic assembly of binary nanoparticle superlattices using protein cages. Nat Nanotechnol. Jan. 2013;8(1):52-6. doi: 10.1038/nnano.2012.220.
Kuzyk et al., DNA-based self-assembly of chiral plasmonic nanostructures with tailored optical response. Nature. Mar. 14, 2012;483(7389):311-4. doi:10.1038/nature10889.
Larson et al., Water-soluble quantum dots for multiphoton fluorescence imaging in vivo. Science. May 30, 2003;300(5624):1434-6.
Liu et al., Three-dimensional plasmon rulers. Science. Jun. 17, 2011;332(6036):1407-10. doi: 10.1126/science.1199958.
Lundgren et al., Self-assembled arrays of dendrimer-gold-nanoparticle hybrids for functional cell studies. Angew Chem Int Ed Engl. Apr. 4, 2011;50(15):3450-3. doi: 10.1002/anie.201006544.
Medintz et al., Quantum dot bioconjugates for imaging, labelling and sensing. Nat Mater. Jun. 2005;4(6):435-46.
Murray et al., Synthesis and Characterization of Monodisperse Nanocrystals and Close-Packed Nanocrystal Assemblies. Annual Review of Materials Science. Aug. 2000;.30:545-610. DOI: 10.1146/annurev.matsci.30.1.545.
Nie et al., Self-assembly of metal-polymer analogues of amphiphilic triblock copolymers. Nat Mater. Aug. 2007;6(8):609-14.
Portney et al., Nanoscale memory characterization of virus-templated semiconducting quantum dots. ACS Nano. Feb. 2008;2(2):191-6. doi: 10.1021/nn700240z.
Qian et al., Imaging pancreatic cancer using surface-functionalized quantum dots. J Phys Chem B. Jun. 28, 2007;111(25):6969-72.
Schreiber et al., Hierarchical assembly of metal nanoparticles, quantum dots and organic dyes using DNA origami scaffolds. Nat Nanotechnol. Jan. 2014;9(1):74-8. doi: 10.1038/nnano.2013.253.
Smith, Semiconductor nanocrystals: structure, properties, and band gap engineering. Acc Chem Res. Feb. 16, 2010;43(2):190-200. doi: 10.1021/ar9001069.

(56) References Cited

OTHER PUBLICATIONS

Song et al., Principles of conjugating quantum dots to proteins via carbodiimide chemistry. Nanotechnology. Dec. 9, 2011;22(49):494006. doi:10.1088/0957-4484/22/49/494006.

Tikhomirov et al., DNA-based programming of quantum dot valency, self-assembly and luminescence. Nat Nanotechnol. Jul. 10, 2011;6(8):485-90. doi: 10.1038/nnano.2011.100.

Walker et al., Geometric curvature controls the chemical patchiness and self-assembly of nanoparticles. Nat Nanotechnol. Sep. 2013;8(9):676-81. doi: 10.1038/nnano.2013.158.

Wang et al., Self-assembled colloidal superparticles from nanorods. Science. Oct. 19, 2012;338(6105):358-63. doi: 10.1126/science.1224221.

Zakeri et al., Spontaneous intermolecular amide bond formation between side chains for irreversible peptide targeting. J Am Chem Soc. Apr. 7, 2010;132(13):4526-7. doi: 10.1021/ja910795a.

Zhang et al., A general strategy for the DNA-mediated self-assembly of functional nanoparticles into heterogeneous systems. Nat Nanotechnol. Nov. 2013;8(11):865-72. doi: 10.1038/nnano.2013.209.

Zhang et al., Controlling macromolecular topology with genetically encoded SpyTag-SpyCatcher chemistry. J Am Chem Soc. Sep. 18, 2013;135(37):13988-97. doi: 10.1021/ja4076452.

Zheng et al., Aqueous Synthesis of Glutathione-Capped ZnSe and $Zn_{1-x}Cd_xSe$ Alloyed Quantum Dots. Adv. Mater. 2007;19: 1475-1479. doi:10.1002/adma.200601939.

PCT/US2015/011534, Oct. 13, 2015, Invitation to Pay Additional Fees.

PCT/US2015/011534, Dec. 21, 2015, International Search Report and Written Opinion.

PCT/US2015/011534, Jul. 28, 2016, International Preliminary Report on Patentability.

\* cited by examiner

FIGs. 14 and 14A-14C
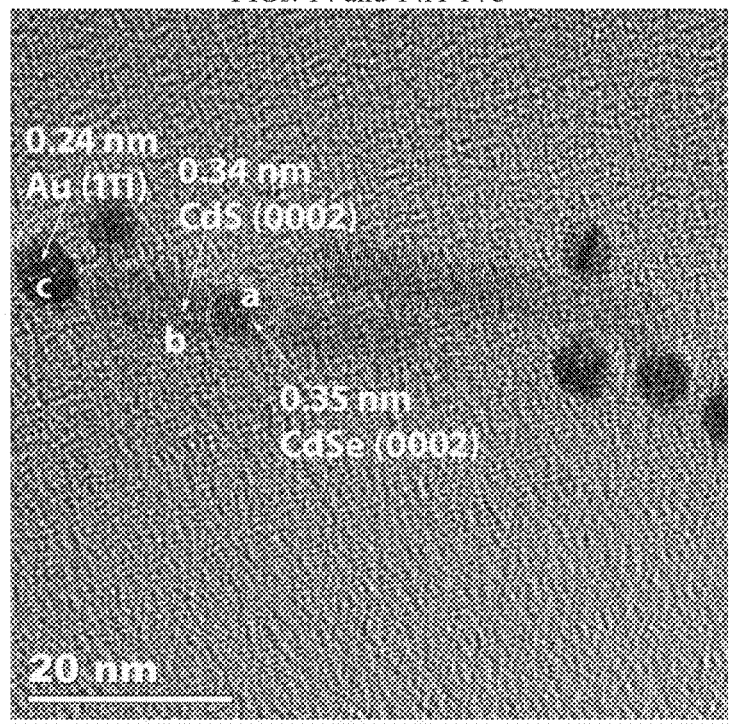
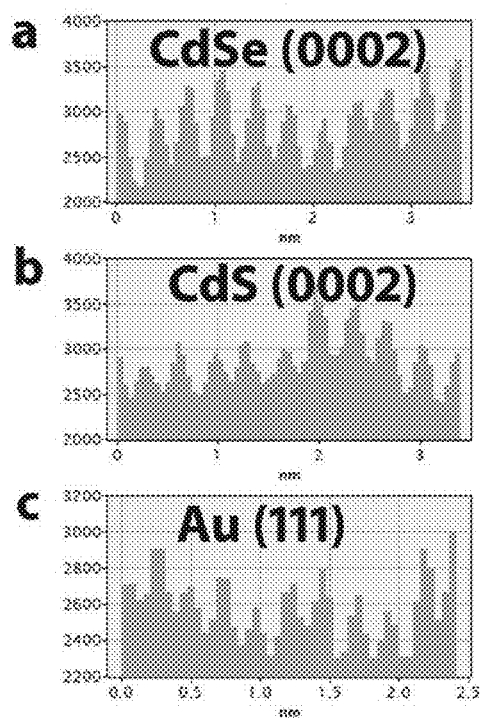

A

B

C

D

E

BIOPOLYMER-MEDIATED ASSEMBLY OF NANOPARTICLES USING GENETICALLY ENCODED PROTEINS

RELATED APPLICATIONS

This application claims the benefit under 35 U.S.C. § 119(e) of U.S. provisional application No. 61/927,924, filed Jan. 15, 2014, and U.S. provisional application No. 62/045,192, filed Sep. 3, 2014, the disclosures of each of which are incorporated by reference herein in their entirety.

FEDERALLY SPONSORED RESEARCH

This invention was made with government support under Contract No. W911NF-11-1-0281 awarded by the Army Research Office and under Contract No. N00014-11-1-0687 awarded by the Navy ONR. The government has certain rights in the invention.

BACKGROUND OF THE INVENTION

Nanomaterials, such as colloidal semiconductor nanocrystals and quantum dots (QDs), have useful physical properties, including high photoluminescence quantum yield, narrow and symmetric photoluminescence spectra, broad absorption profiles, large effective Stokes shift, high multiphoton excitation cross sections, and remarkable chemical, photonic, and colloidal stabilities.[29-32] The successful conjugation of colloidal semiconductor nanocrystals with biological molecules, such as proteins and DNA, is a critical step for their applications as fluorescent probes and bio-inspired self-assembled materials.[33, 34] Over the past 15 years, there have been continuous efforts to develop QD-biomolecule conjugation methods.[29-37] Among them, carbodiimide crosslinker chemistry,[33,37] such as 1-Ethyl-3-(3-dimethylaminopropyl)carbodiimide (EDC)/N-Hydroxysuccinimide (NHS), is often used to attach QDs with proteins, typically by amide bond formation between terminal carboxyls on QD ligands and amines on proteins.

SUMMARY OF THE INVENTION

The present disclosure provides, inter alia, a platform for producing robust and highly fluorescent self-assembling biopolymer scaffolds that are scalable, low-cost, and produced in part by recombinant cells (e.g., bacteria). The engineered biopolymers (e.g., amyloid fibrils) and genetically encoded chemistries provided herein enable the self-assembly of, for example, micron-level one-dimensional semiconductor nanocrystal chains and semiconductor-metal nanoheterostructures. The genetically programmable scaffolds of the present disclosure are useful for a variety of nanotechnology applications including, without limitation, facilitating the patterning of functional nanomaterials for large-area light harvesting and emitting devices as well as biological applications using, for example, low-cost and renewable scaffolds.

In one embodiment, a population of cells was genetically engineered to express biopolymers largely composed of protein subunits that self-assemble in the extracellular space (see Examples). These biopolymers were functionalized with peptide tags to organize nanoparticles-protein conjugates into higher-order structures through irreversible isopeptide binding of the peptide tags to the proteins of the conjugates.

Thus, some aspects of the present disclosure provide compositions that include at least one nanoparticle linked to a first polypeptide, and a biopolymer linked to at least one second polypeptide that binds covalently to the first polypeptide. In some embodiments, the second polypeptide is a heterologous polypeptide relative to the biopolymer.

In some embodiments, the at least one nanoparticle comprises at least one material selected from a metal, a noble metal, an oxide, a semiconductor material, or a combination of two or more of the foregoing. In some embodiments, the at least one material comprises at least one semiconductor material. For example, the at least one semiconductor material may be selected from cadmium sulfide (CdS), cadmium selenide (CdSe), cadmium telluride (CdTe), zinc sulfide (ZnS), zinc selenide (ZnSe), indium phosphide (InP), lead sulfide (PbS), and lead selenide (PbSe).

In some embodiments, the at least one nanoparticle comprises a core material and at least one shell material.

In some embodiments, the at least one nanoparticle is linked to the first polypeptide through a peptide linker such as, for example, a dipeptide linker. The dipeptide linker may be, but is not limited to, a cysteine-cysteine ($Cys_2$) linker or a histidine-histidine ($His_2$) linker.

In some embodiments, the peptide linker links a terminus of the first polypeptide to an external surface of the nanoparticle. For example, the peptide linker may link the N-terminus of the first polypeptide to an external surface of the nanoparticle.

In some embodiments, the biopolymer is an amyloid fibril, a pilus or a flagellum. In embodiments wherein the biopolymer is an amyloid fibril, the fibril may comprise at least one CsgA protein subunit.

In some embodiments, the biopolymer has a length of at least one micron. For example, the biopolymer may have a length of one micron to five microns.

In some embodiments, the second polypeptide forms an isopeptide bond with the first polypeptide.

In some embodiments, one of the first and second polypeptides comprises a peptide tag, and the other of the first and second polypeptides comprises a protein. For example, the first polypeptide may comprise the protein, and the second polypeptide may comprise the peptide tag.

Some aspects of the present disclosure provide compositions that include at least one semiconductor nanoparticle linked to a protein (e.g., SpyCatcher, pilin-C or pilin-N), and an amyloid fibril linked to at least one peptide tag (e.g., SpyTag, IsopepTagC or IsopepTagN) that binds covalently to the protein. The at least one semiconductor material may be selected from cadmium sulfide (CdS), cadmium selenide (CdSe), cadmium telluride (CdTe), zinc sulfide (ZnS), zinc selenide (ZnSe), indium phosphide (InP), lead sulfide (PbS), and lead selenide (PbSe).

Other aspects of the present disclosure provide a biopolymer linked to at least two polypeptides, each polypeptide covalently linked through an isopeptide bond to a nanoparticle-polypeptide conjugate.

In some embodiments, at least one of the polypeptides is different from at least one other of the polypeptides. In some embodiments, at least one of the nanoparticle-polypeptide conjugates is different from at least one other of the nanoparticle-polypeptide conjugates.

In some embodiments, a nanoparticle of the nanoparticle-polypeptide conjugate comprises at least one material selected from a metal, a noble metal, an oxide, a semiconductor material, or a combination of two or more of the foregoing. In some embodiments, the at least one material comprises at least one semiconductor material. For example, the at least one semiconductor material may be selected from cadmium sulfide (CdS), cadmium selenide (CdSe), cadmium telluride (CdTe), zinc sulfide (ZnS), zinc selenide (ZnSe), indium phosphide (InP), lead sulfide (PbS), and lead selenide (PbSe).

In some embodiments, the nanoparticle of a nanoparticle-polypeptide conjugate comprises a core material and at least one shell material.

In some embodiments, the nanoparticle and the polypeptide of a nanoparticle-polypeptide conjugate are linked to each other through a peptide linker. In some embodiments, the peptide linker is a dipeptide linker. A didpeptide linker may be, for example, a cysteine-cysteine ($Cys_2$) linker or a histidine-histidine ($His_2$) linker.

In some embodiments, a peptide linker links a terminus of the polypeptide to an external surface of the nanoparticle. For example, a peptide linker may link the N-terminus of the polypeptide to an external surface of the nanoparticle.

In some embodiments, a biopolymer is an amyloid fibril, a pilus or a flagellum. In some embodiments, an amyloid fibril comprises at least one CsgA protein subunit.

In some embodiments, a biopolymer has a length of at least one micron. For example, a biopolymer may have a length of one micron to five microns.

In some embodiments, each of the at least two polypeptides linked to the biopolymer comprises a peptide tag.

In some embodiments, the polypeptide of a nanoparticle-polypeptide conjugate is a protein that forms a covalent linked through an isopeptide bond to the peptide tag.

Also provided herein are pluralities of any of the foregoing biopolymers as well as compositions comprising any of the foregoing biopolymers.

Further aspects of the present disclosure provide nanocrystal structures and/or heteronanocrystals (HNCs) that include at least one amyloid fibril with repeating CsgA protein subunits linked to a peptide tag that forms an isopeptide bond with a protein of a nanoparticle-protein conjugate.

In some embodiments, the nanoparticle of a nanoparticle-protein conjugate comprises at least one material selected from a metal, a noble metal, an oxide, a semiconductor material, or a combination of two or more of the foregoing. In some embodiments, the at least one material comprises at least one semiconductor material. For example, the at least one semiconductor material may be selected from cadmium sulfide (CdS), cadmium selenide (CdSe), cadmium telluride (CdTe), zinc sulfide (ZnS), zinc selenide (ZnSe), indium phosphide (InP), lead sulfide (PbS), and lead selenide (PbSe).

In some embodiments, the nanoparticle of a nanoparticle-protein conjugate comprises a core material and at least one shell material.

In some embodiments, the nanoparticle and the protein of a nanoparticle-protein conjugate are linked to each other through a peptide linker. In some embodiments, the peptide linker is a dipeptide linker. For example, a dipeptide linker may be a cysteine-cysteine ($Cys_2$) linker or a histidine-histidine ($His_2$) linker.

In some embodiments, a peptide linker links a terminus of the protein to an external surface of the nanoparticle. For example, a peptide linker may link the N-terminus of the protein to an external surface of the nanoparticle.

In some embodiments, an amyloid fibril has a length of at least one micron. For example, an amyloid fibril may have a length of one micron to five microns.

Also provided herein are compositions that include a plurality of any of the foregoing nanocrystal structures.

Additional aspects of the present disclosure provide methods of conjugating a polypeptide to a semiconductor nanoparticle. In some embodiments, methods comprise synthesizing a nanoparticle core, solubilizing the nanoparticle core, thereby producing a solubilized nanoparticle core, combining the solubilized nanoparticle core with semiconductor precursors and a polypeptide comprising a peptide linker, thereby forming a reaction mixture, and incubating the reaction mixture under conditions that permit formation of a semiconductor shell around the solubilized nanoparticle core and conjugation of the polypeptide to a surface of the semiconductor shell through a peptide linker, thereby producing a nanoparticle-polypeptide conjugate. In some embodiments, methods include a ligand exchange step.

In some embodiments, the synthesized nanoparticle core is hydrophilic and does not require solubilization. Thus, in some embodiments, the solubilization step is optional. That is, in some embodiments, methods of conjugating a polypeptide to a semiconductor nanoparticle comprises synthesizing a nanoparticle core, combining the nanoparticle core with semiconductor precursors and a polypeptide comprising a peptide linker, thereby forming a reaction mixture, and incubating the reaction mixture under conditions that permit formation of a semiconductor shell around the solubilized nanoparticle core and conjugation of the polypeptide to a surface of the semiconductor shell through a peptide linker, thereby producing a nanoparticle-polypeptide conjugate. In some embodiments, methods include a ligand exchange step.

In some embodiments, methods further comprise purifying the reaction mixture. For example, a reaction mixture may be purified by filtration.

In some embodiments, semiconductor nanoparticles are solubilized through ligand exchange.

In some embodiments, a reaction mixture is incubated for a period of at least 10 minutes. For example, a reaction mixture may be incubated for a period of 10 minutes to 60 minutes. In some embodiments, a reaction mixture is incubated for a period of 30 minutes.

In some embodiments, a reaction mixture is incubated at a temperature of at least 80° C. For example, a reaction mixture may be incubated at a temperature of 80° C. to 100° C. In some embodiments, a reaction mixture is incubated at a temperature of 90° C.

In some embodiments, a nanoparticle core and/or semiconductor shell comprise(s) at least one material selected from cadmium sulfide (CdS), cadmium selenide (CdSe), cadmium telluride (CdTe), zinc sulfide (ZnS), zinc selenide (ZnSe), indium phosphide (InP), lead sulfide (PbS), and lead selenide (PbSe). In some embodiments, a nanoparticle core and a semiconductor shell comprise different materials.

In some embodiments, a peptide linker is a dipeptide linker. For example, a dipeptide linker may be a cysteine-cysteine (Cys2) linker or a histidine-histidine (His2) linker.

Other aspects of the present disclosure provide methods of producing a biopolymer scaffold. In some embodiments, methods comprise expressing in a first recombinant cell (e.g., recombinant bacterial cell) a first polynucleotide encoding a protein linked to a peptide linker, isolating the protein linked to a peptide linker, conjugating the protein to nanoparticles through the peptide linker, thereby forming nanoparticle-protein conjugates, expressing in a second recombinant cell (e.g., recombinant bacterial cell) a second polynucleotide encoding a subunit of a biopolymer linked to a peptide tag that forms a covalent isopeptide bond with the protein, thereby forming tag-displaying biopolymers, and combining the nanoparticle-protein conjugates with the tag-displaying biopolymers to form a reaction mixture, and incubating the reaction mixture under conditions that permit isopeptide bond formation between the proteins of the nanoparticle-protein conjugates and the peptide tags of the tag-displaying biopolymers, thereby producing a biopolymer scaffold.

Yet other aspects of the present disclosure provide methods of producing a nanostructure, comprising culturing in a structurally-defined shape recombinant cells (e.g., recombinant bacterial cells) that express a polynucleotide encoding a subunit of a biopolymer linked to a peptide tag that forms a covalent isopeptide bond with a protein, thereby producing tag-displaying biopolymers, and contacting the recombinant cells with nanoparticle-protein conjugates that comprise the protein linked to a peptide linker under conditions that permit isopeptide bond formation between proteins of the nanoparticle-protein conjugates and peptide tags of the tag-displaying biopolymers, thereby producing a nanostructure.

In some embodiments, methods further comprise isolating the biopolymer scaffold or the nanostructure.

In some embodiments, a nanoparticle comprises at least one material selected from a metal, a noble metal, an oxide, a semiconductor material, or a combination of two or more thereof. In some embodiments, the at least one material comprises at least one semiconductor material. For example, the at least one semiconductor material may selected from cadmium sulfide (CdS), cadmium selenide (CdSe), cadmium telluride (CdTe), zinc sulfide (ZnS), zinc selenide (ZnSe), indium phosphide (InP), lead sulfide (PbS), and lead selenide (PbSe).

In some embodiments, a nanoparticle comprises a core material and at least one shell material.

In some embodiments, a peptide linker is a dipeptide linker. For example, a dipeptide linker may be a cysteine-cysteine (Cys2) linker or a histidine-histidine (His2) linker.

In some embodiments, a peptide linker links a terminus of the protein to an external surface of the nanoparticle.

In some embodiments, the subunit of the biopolymer is a CsgA protein subunit.

In some embodiments, conditions that permit isopeptide bond formation include incubating the reaction mixture, or contacting the recombinant cells (e.g., recombinant bacterial cells) with nanoparticle-protein conjugates, at a temperature of 15° C. to 35° C. For example, conditions that permit isopeptide bond formation may include incubating the reaction mixture, or contacting the recombinant cells with nanoparticle-protein conjugates, at a temperature of 25° C. In some embodiments, conditions that permit isopeptide bond formation include incubating the reaction mixture, or contacting the recombinant cells with nanoparticle-protein conjugates, for a period of at least 15 minutes.

In some embodiments, conditions that permit isopeptide bond formation include incubating the reaction mixture, or contacting the recombinant cells with nanoparticle-protein conjugates, for a period of 15 minutes to 60 minutes. For example, conditions that permit isopeptide bond formation may include incubating the reaction mixture, or contacting the recombinant cells with nanoparticle-protein conjugates, for a period of 30 minutes.

In some embodiments, a biopolymer scaffold has a length of at least one micron. For example, a biopolymer scaffold may have a length of one micron to five microns.

In some embodiments, a nanoparticle is a semiconductor nanoparticle with a core and a shell, and a protein is conjugated to the semiconductor nanoparticle using a method that comprises synthesizing a nanoparticle core, optionally solubilizing the nanoparticle core, thereby producing a solubilized nanoparticle core, combining the solubilized nanoparticle core with semiconductor precursors and a polypeptide comprising a peptide linker, thereby forming a reaction mixture, and incubating the reaction mixture under conditions that permit formation of a semiconductor shell around the solubilized nanoparticle core and conjugation of the polypeptide to a surface of the semiconductor shell through a peptide linker, thereby producing a nanoparticle-polypeptide conjugate.

In some embodiments, the first bacterial cell and/or the second bacterial cell is an *Escherichia coli* cell.

Some aspects of the present disclosure provide rationally-designed nanostructures that comprise a plurality of tag-displaying biopolymers bound to a plurality of nanoparticle-protein conjugates.

Some aspects of the present disclosure provide methods of producing an optoelectronic device, comprising (a) culturing on a dielectric layer of a substrate recombinant cells (e.g., recombinant bacterial cells) that express (i) a first polynucleotide encoding a subunit of a biopolymer linked to a first peptide tag and (ii) a second polynucleotide encoding a subunit of a biopolymer linked to a second peptide tag, wherein the substrate contains a gate electrode on a surface of the substrate, (b) contacting the recombinant cells with (iii) a carbon nanotube linked to a first protein that forms a covalent isopeptide bond with the first peptide tag and (iv) a nanoparticle linked to a second protein that forms a covalent isopeptide bond with the second tag, and (c) depositing onto recombinant cells of (b) a source electrode and a draw electrode, thereby producing an optoelectronic device.

In some embodiments, the substrate comprises silicon.

In some embodiments, the dielectric layer comprises $SiO_2$.

In some embodiments, the gate electrode comprises gallium-indium eutectic.

In some embodiments, the source electrode and the draw electrode comprise silver paste.

In some embodiments, the nanoparticle comprises at least one material selected from a metal, a noble metal, an oxide, a semiconductor material, or a combination of two or more thereof. In some embodiments, the at least one material comprises at least one semiconductor material. In some embodiments, the at least one semiconductor material is selected from cadmium sulfide (CdS), cadmium selenide (CdSe), cadmium telluride (CdTe), zinc sulfide (ZnS), zinc selenide (ZnSe), indium phosphide (InP), lead sulfide (PbS), and lead selenide (PbSe). In some embodiments, the nanoparticle comprises a core material and at least one shell material.

In some embodiments, the peptide linker is a dipeptide linker. In some embodiments, the dipeptide linker is a cysteine-cysteine (Cys2) linker or a histidine-histidine (His2) linker.

In some embodiments, the peptide linker links a terminus of the protein to an external surface of the nanoparticle.

In some embodiments, the subunit of the biopolymer is a CsgA protein subunit.

In some embodiments, the optoelectronic device is a field effect transistor.

Also provided herein are optoelectronic devices produced by methods as provided herein.

Some aspects of the present disclosure provide optoelectronic devices comprising (a) a substrate containing a dielectric layer and a gate electrode on respective surfaces of the substrate, (b) a plurality of first biopolymers linked to first peptide tags and a plurality of second biopolymers linked to second peptide tags, (c) a plurality of carbon nanotubes linked to first proteins that form covalent isopeptide bonds with the first peptide tags and a plurality of nanoparticles linked to second proteins that form covalent isopeptide bonds with the second peptide tags, and (d) source and draw electrodes, wherein the plurality of (a), the plurality of (b), and the source and draw electrodes are located on the dielectric layer of the substrate.

BRIEF DESCRIPTION OF THE DRAWINGS

The accompanying drawings are not intended to be drawn to scale. In the drawings, each identical or nearly identical component illustrated in various figures is represented by a like numeral. For purposes of clarity, not every component may be labeled in every drawing.

FIG. 4A shows an image of the resulting self-assemblies illuminated with 365 nm UV light in dark conditions; TEM image from the middle glass dish in the image in FIG. 4A shows SpyTag-displaying amyloid fibrils organizing CdTe/CdS QD-SpyCatcher conjugates; the enlarged image in FIG. 4C corresponds to the area outlined by a white square in FIG. 4B;

FIG. 6B, ultraviolet light)

FIG. 14 (top image) shows an example of an HRTEM image of the area marked by the white square in FIG. 13; FIGS. 14A-14C show line scans of the TEM lattice fringes marked in the top image, confirming the lattice constants, respectively.

FIG. 15F is a high magnification image of the rectangular area of FIG. 15E, and the circles in FIG. 15F delineate single QDs.

FIG. 20A shows CNTs functionalized with Cys2-SpyCatcher proteins in 1×PBS buffer. FIG. 20B shows CNTs well-dispersed with SpyCatcher (bottle "1") but not dispersed without SpyCatcher (bottle "2"). FIG. 20C shows pictures and schematics illustrating the growth and organization of CNT-SpyCatcher and red QD-Pilin-N conjugates on mixed CsgASpyTag and CsgAIsopepTagN amyloid fibrils with live cells deposited on SiO$_2$-covered silicon wafers. FIGS. 20D-20H show scanning electron microscopy (SEM) and TEM images of the CNTs and QDs organized by E. coli in the channel of the device. FIG. 20I shows a schematic of FETs and photodetectors built via CNT-SpyCatcher and QD-Pilin-N assembled on curli amyloid fibrils. FIG. 20J shows I$_{ds}$ versus V$_{gs}$ characteristic of the CNT-QDs assembled on curli fibers from E. coli bridging two silver electrodes on SiO$_2$ in the dark at V$_{ds}$=1.0 V, exhibiting p-type semiconductor behavior. FIG. 20K shows drain current (I$_{ds}$) vs drain voltage (V$_{ds}$) at V$_{gs}$=0 V of the bacterially organized CNT device with QDs along without (black curve) and with (gray curve) optical illumination (532 nm light with P$_{light}$=20 mW cm−2). FIG. 20L shows Drain current (I$_{ds}$) over time under chopped illumination of the bacterially organized CNT-QD device at V$_{ds}$=0.5 V with 532 nm light.

FIG. 21A shows TEM images showing the wild-type curli fibrils with live cells before adding CNTs. FIG. 21B shows that adding CNT-SpyCatcher to the wild-type amyloid fibrils with live cells resulted in no significant organization of bacterial-CNT structures. FIGS. 21C and 21D show CNT-SpyCatcher self-organized with CsgASpyTag amyloid fibrils expressed by live cells. FIGS. 21E and 21F show CNT-SpyCatcher co-organized with red-emission CdTe/CdS QD-Pilin-N on mixed CsgASpyTag+CsgAIsopepTagN amyloid fibrils with live cells.

FIG. 22A shows an absence of biofilm growth on a silicon wafer in the absence aTc inducer. FIG. 22B shows biofilm growth on a silicon wafer in the presence of an aTc inducer before adding CNT-SpyCatcher conjugates. FIG. 22C shows CNT organization with the biofilm in the present of an aTc inducer after adding CNT-SpyCatcher conjugates. FIG. 22D shows CNT and QD co-organization with the biofilm in the present of an aTc inducer and the CNT-SpyCatcher and QD-Pilin-N conjugates.

DETAILED DESCRIPTION OF THE INVENTION

Figures 1A, 1O:
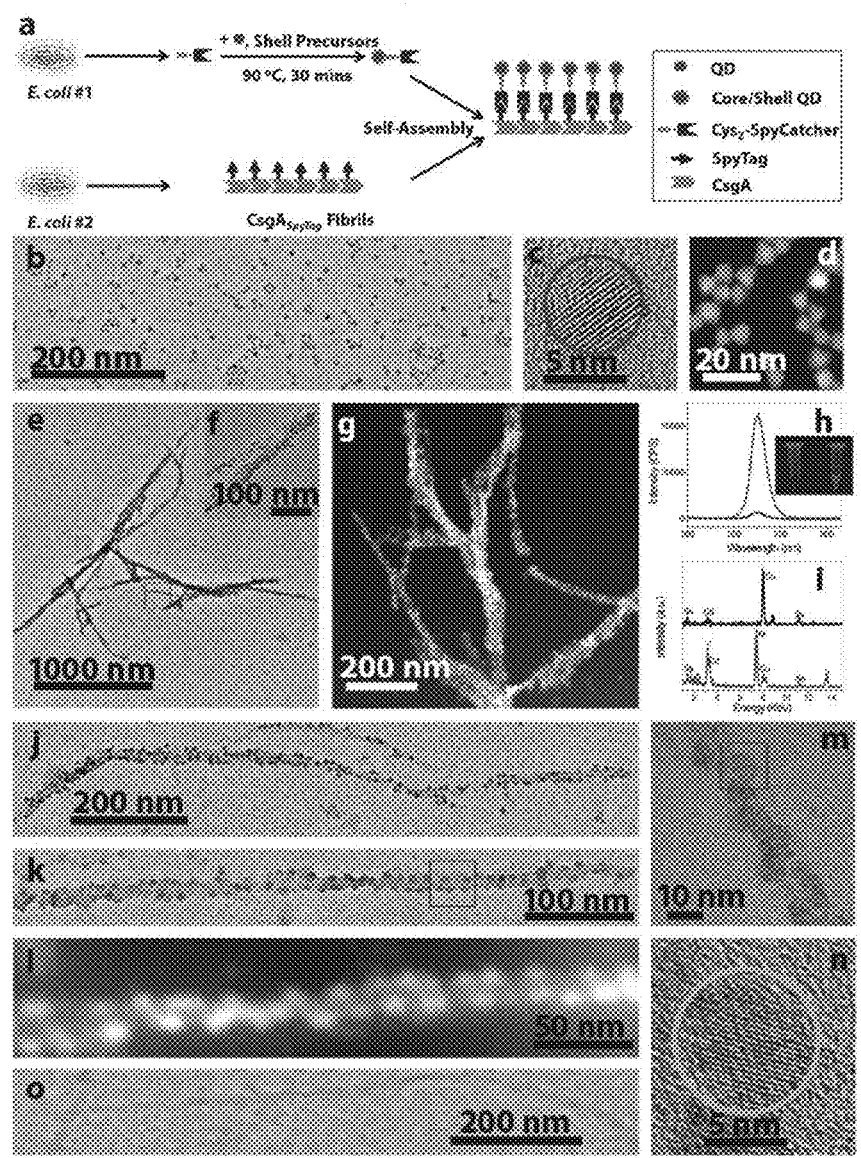
FIGS. 1A-1O show an example of the synthesis of CdSe/CdS core/shell quantum dot (QD)-SpyCatcher conjugates and their self-assembly on genetically encoded curli amyloid fibrils via specific SpyTag-SpyCatcher chemistry.

Provided herein, in various aspects and embodiments, are methods and compositions for synthesizing programmable self-assembling scaffolds for use with a variety of nanotechnology and/or biological applications. Also provided herein are methods for achieving rapid and robust nanoparticle-protein conjugation. As shown in FIG. 1A, aspects of the present disclosure use peptide linkages (e.g., cysteine (Cys) linkages) that are genetically encoded in proteins of a protein-peptide binding pair (e.g., SpyCatcher, pilin-C or pilin-N proteins expressed by Escherichia coli (E. coli)). These linkages are attached to the nanoparticle surface during nanoparticle synthesis. This synthetic route results, in many instances, in robust nanoparticle-protein conjugates that are highly stable and fluorescent, and can be used with a wide range of, for example, semiconductor materials with variable compositions, sizes, and morphologies. Nanoparticle-protein conjugates provided herein may then be used in combination with tag-displaying biopolymers (e.g., amyloid fibrils, pili, or flagella) provided herein to synthesize higher-order scaffolds such as, for example, micron-scale one-dimensional nanoparticle chains.

Nanoparticles

A "nanoparticle," as used herein, refers to a small object that behaves as a whole unit in terms of its transport and properties. The nanoparticles described herein are used, in some embodiments, to form nanomaterials and nanostructures, including for example nanoparticle-protein conjugates, nanocrystals and biopolymer scaffolds. In some embodiments, a nanoparticle has a diameter of 2500 nanometers or less. In some embodiments, a nanoparticle has a diameter of 1 to 1000 nanometers, 1 to 750 nanometers, 1 to 500 nanometers, 1 to 250 nanometers, 1 to 100 nanometers, 1 to 50 nanometers, 1 to 25 nanometers, or 1 to 10 nanometers. In some embodiments, a nanoparticle has a diameter of less than or equal to 100 nanometers. For example, in some embodiments, a nanoparticle has a diameter of 1, 2, 3, 4, 5, 6, 7, 8, 9, 10, 15, 20, 25, 30, 35, 40, 45, 50, 55, 60, 65, 70, 75, 80, 85, 90, 95 or 100 nanometers. In some embodiments, a nanoparticle has a diameter of 200, 300, 400, 500, 600, 700, 800, 900 or 1000 nanometers.

Nanoparticles provided herein may vary in their structure. For example, a nanoparticle may be uniform in that it includes only one type of material (e.g., single alloy or a binary alloy). Such nanoparticles are herein considered to have a core-only structure. In some embodiments, a nanoparticle may be structured such that it includes more than one type of material. For example, a nanoparticle may be layered. In some embodiments, a layered nanoparticle includes a core/shell or a core/(shell)$_n$ structure, where "n" is the number of shells (or layers), and the outer shell protects and insulates the inner shell(s) (or layer(s)) and core. For such layered nanoparticles, each layer (e.g., core, (shell)$_n$) typically includes a differed type of material. For example, a nanoparticle with a core/shell structure may include a core of CdSe or CdTe and a shell of CdS. It should be understood, however, that each of a core/shell structure may include only a single type of material (e.g., single alloy or a binary alloy). For example, a nanoparticle core may be synthesized with a material, and a shell may be synthesized with the same material. In this way, for example, a polypeptide may be linked, using a conjugation method provided herein, to nanoparticles that include only one type of material.

Nanoparticle materials for use in accordance with the present disclosure include, without limitation, semiconductor materials, insulator materials (e.g., $SiO_2$), noble metal materials, metal oxide materials, and polymeric materials. Polymeric nanoparticles are also contemplated (e.g., composed of proteins, polysaccharides and/or synthetic polymers).

In some embodiments, a core of a nanoparticle comprises a semiconductor material, a noble metal material, a metal oxide material, an insulator material, or a polymeric material, while a shell of the nanoparticle comprises a metallic material (e.g., a semiconductor material, a noble metal material, or a metal oxide material).

Common semiconductor materials used to synthesize nanoparticles include binary mixtures of II-VI, III-V and IV-VI semiconductor materials, but are not so limited.

Examples of II-VI semiconductor materials for use in synthesizing nanoparticles include, without limitation, cadmium selenide, cadmium sulfide, cadmium telluride, zinc oxide, zinc selenide, zinc sulfide, zinc telluride, cuprous chloride, copper sulfide, lead selenide, lead sulfide, lead telluride, tin sulfide, tin sulfide, tin telluride, lead tin telluride, thallium tin telluride, thallium germanium telluride and bismuth telluride. Other semiconductor materials may be used in accordance with the present disclosure.

Examples of III-V semiconductor materials for use in synthesizing nanoparticles include, without limitation, boron nitride, boron nitride, boron nitride, boron phosphide, boron arsenide, boron arsenide, aluminium nitride, aluminium phosphide, aluminium arsenide, aluminium antimonide, gallium nitride, gallium phosphide, gallium arsenide, gallium antimonide, indium nitride, indium phosphide, indium arsenide and indium antimonide.

Examples of IV-VI semiconductor materials for use in synthesizing nanoparticles include, without limitation, lead selenide, lead sulfide, lead telluride, tin sulfide, tin sulfide, tin telluride, lead tin telluride, thallium tin telluride and thallium germanium telluride.

In some embodiments, nanoparticles may be referred to as "semiconductor nanocrystals," or "quantum dots." It should be understood that the terms may be used interchangeable and refer to nanocrystalline particles commonly synthesized from binary mixtures of II-VI, III-V or IV-VI semiconductor materials including ZnS, ZnSe, CdS, CdSe, CdTe, InP, as well as other semiconductor materials. Quantum dots have several useful physical properties, including high photoluminescence quantum yield, narrow and symmetric photoluminescence spectra, broad absorption profiles, large effective Stokes shift, high multi-photon excitation cross sections, and remarkable chemical, photonic, and colloidal stabilities. Depending on the material used to synthesize the quantum dot, and the size of the quantum dot, its fluorescence spectra may vary.

Noble metals are elements characterized by an electron configuration that imparts a certain chemical inertia and resistance to corrosion and oxidation (Sapsford, K. E., et al., *Chemical Reviews,* 2013, 113, 1904-2074). Examples of noble metals for use herein include, without limitation, rhenium, ruthenium, rhodium, palladium, silver, osmium, iridium, platinum and gold.

Examples of metal oxides for use in synthesizing nanoparticles include, without limitation, iron oxide, silicon dioxide and titanium dioxide. Other metal oxides may be used in accordance with the present disclosure.

Examples of polymeric materials include proteins, polysaccharides and/or polymeric nanoparticles.

It should be understood that, in some embodiments, the invention contemplates the use of nanoparticles composed of other organic or inorganic materials that can be coated with a semiconductor material. For example, other materials (e.g., an oxide or polymeric materials) may form the core of a nanoparticle, while any of the semiconductor materials provided herein may for one or more shells of the nanoparticle.

Polypeptides

A "polypeptide," as used herein, refers to a chain of amino acids, of any length, linked by peptide (amide) bonds. A "protein" herein refers to a biological molecule that contains a chain of amino acids that is greater than 50 amino acids linked by peptide (amide) bonds. A protein may contain more than one amino acid chain. A "peptide" herein refers to a chain of amino acids that is 50 amino acids or fewer linked by peptide (amide) bonds. In some embodiments, a peptide may consist of less than 45, 40, 35, 30, 25, 20, 15, 10 or 5 amino acids. For example, a peptide may be a dipeptide, which refers to two amino acids linked by a single peptide bond. The term "polypeptide" herein encompasses proteins and peptides unless otherwise provided. For example, various aspects and embodiments of the present disclosure describe a polypeptide linked to a nanoparticle. It should be understood that the polypeptide may be a protein or peptide unless otherwise provided. That is, a protein or a peptide may be linked to a nanoparticle as disclosed herein. Likewise, various aspects and embodiments of the present disclosure describe a polypeptide linked to a biopolymer or a biopolymer subunit. In such aspects and embodiments, it should be understood that a protein or a peptide may be linked to a biopolymer or biopolymer subunit described herein unless otherwise provided.

In some embodiments, a polypeptide is a heterologous polypeptide. As used herein, a "heterologous polypeptide" (e.g., relative to a biopolymer such as an amyloid fiber) refers to a polypeptide within or appended to a biopolymer that is not normally expressed in the corresponding wild-type biopolymer. A heterologous polypeptide may be added at the N-terminus, C-terminus and/or internally within a biopolymer, such as an amyloid fiber. A peptide tag (e.g., linked to a biopolymer) and/or a peptide linker (e.g., linking a protein to a nanoparticle) as provided herein, for example, may be, and typically is, a heterologous polypeptide. It should be understood, however, that a peptide tag and/or peptide linker is not necessarily a heterologous peptide.

Some aspects of the present disclosure provide protein-protein and protein-peptide binding pairs that are used to organize nanoparticles into higher order structures. For brevity, the term "polypeptide binding pair" will encompass both protein-protein binding pairs and protein-peptide binding pairs, unless otherwise provided. Partners of a polypeptide binding pair as provided herein, in some embodiments, are considered to be highly reactive in that they undergo isopeptide bond formation (e.g., autocatalytic isopeptide bond formation), resulting in irreversible (e.g., covalent) amide bond formation between the partners of the binding pair. Thus, "a second polypeptide that binds covalently to a first polypeptide" herein refers to polypeptides of a binding pair that form a covalent bond with each other.

An example of a binding pair for use in accordance with the present disclosure includes SpyCatcher and SpyTag.[26, 27] SpyTag-SpyCatcher chemistry was developed by Howarth and co-workers[26] and involves a genetically encodable, highly reactive peptide-protein pair engineered by splitting the autocatalytic isopeptide-bond-containing CnaB2 domain from *Streptococcus pyogenes*. Upon simple mixing, SpyTag and SpyCatcher undergo autocatalytic isopeptide bond formation between $Asp_{117}$ on SpyTag (~1.3 kDa) and Lys31 on SpyCatcher (~12.3 kDa), resulting in irreversible amide bond formation in minutes within both in vitro and in vivo environments.[27] The reaction can occur in high yield upon mixing the binding pair and amidst diverse conditions of pH, temperature, and buffer.

Another example of a binding pair for use in accordance with the present disclosure includes isopeptag and pilin-C.[28] Similar to the SpyTag-SpyCatcher binding pair described above, the isopeptag-pilin-C system is derived from splitting a bacterial protein into a peptide tag and a binding partner protein. In its native form, the pilin-C subunits form two intramolecular isopeptide bonds that provide stability to the pilin structure. One of the isopeptide bonds is split to generate the isopeptag peptide and the protein binding pair. Isopeptag is a 16 amino acid peptide tag. When combined, isopeptag and the pilin-C bind pair form an isopeptide bond to irreversibly link (e.g., covalently link) the binding partners to each other.

Other covalent binding pair may be used in accordance with the present disclosure.

It should be understood that while various aspects and embodiments of the present disclosure describe linkage of a protein to a nanoparticle and linkage of its peptide tag binding partner to a subunit of a biopolymer (e.g., an amyloid fibril), the reverse is also contemplated. That is, in some embodiments, a peptide tag is linked to a nanoparticle, and its protein binding partner is linked to a subunit of a biopolymer. Thus, in some embodiments, a SpyCatcher protein is conjugated to a nanoparticle and its binding partner SpyTag is fused to a biopolymer subunit. In other embodiments, a SpyTag peptide is conjugated to a nanoparticle and its binding partner SpyCatcher protein is fused to a biopolymer subunit. Likewise, in some embodiments, a pilin-C protein is conjugated to a nanoparticle and its binding partner isopeptag peptide is fused to a biopolymer subunit. In other embodiments, an isopeptag peptide is conjugated to a nanoparticle and its binding partner pilin-C protein is fused to a biopolymer subunit.

Aspects of the present disclosure provide methods of engineering cells (e.g., bacterial cells such as *E. coli* cells) to produce polypeptides with peptide linkers. General methods of bacterial cell protein expression are known. In some embodiments, codons encoding peptide linkers may be introduced to a gene encoding, for example, a protein of a protein-peptide binding pair. In some embodiments, codons encoding one or more, preferably two or more, amino acids, such as cysteine residues, are introduced to a gene encoding, for example, a protein of a protein-peptide binding pair. The recombinant protein may then be expressed in cells (e.g., bacterial cells such as *E. coli* cells), and purified.[31,51] In some embodiments, codons encoding amino acids of a peptide linker are introduced after the start codon of a gene, while in other embodiments, codons encoding amino acids of a peptide linker are introduced before the stop codon of a gene.

Peptide Linkers

In some embodiments, a polypeptide is linked to an external surface (e.g., shell) of a nanoparticle. A polypeptide, in some embodiments, may be linked to a nanoparticle through a peptide linker. A "peptide linker," as used herein, refers to a short chain of amino acids linked by peptide (amide) bonds that links two molecules to each other. A "peptide bond" is herein considered to be a covalent chemical bond formed between two molecules when the carboxyl group of one molecule reacts with the amino group of the other molecule, causing the release of a molecule of water (i.e., $H_2O$).

A peptide linker may be 1 to 30 amino acids in length. For example, a peptide linker may be 1 to 5, 1 to 10, 1 to 15, 1 to 20, 1 to 25, or 1 to 30 amino acids in length. In some embodiments, a peptide linker is 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 amino acids in length. In some embodiments, a peptide linker is more than 30 amino acids in length.

A peptide linker may comprise any combination of amino acids. Amino acids for use with peptide linkers provided herein include alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine. The amino acids may be unmodified or modified.

In some embodiments, a peptide linker is a dipeptide linker (e.g., two amino acids joined by a single peptide bond). A dipeptide linker may include the same amino acids or different amino acids. In some embodiments, a dipeptide linker includes cysteine ("Cys" or "C") amino acids, designated herein as a "$Cys_2$ linker." In some embodiments, a dipeptide linker includes histidine ("His" or "H") amino acids, designated herein as a "$His_2$" linker. Examples of methods of conjugating a polypeptide to a nanoparticle via a peptide linker are provided herein.

In some embodiments, a peptide linker links a terminus (i.e., 5' (N-terminus) or 3' (C-terminus)) of a polypeptide to an external surface of a nanoparticle. In other embodiments, a peptide linker links an internal or central region of a polypeptide to an external surface of a nanoparticle. In some embodiments, the polypeptide is synthesized with the peptide linker already attached to one of its termini. For example, in some embodiments, a protein with a peptide linker may be synthesized by introducing, to the 5' end of a gene encoding the protein, codons encoding specific amino acid residues (e.g., two cysteine residues). For example, codons encoding amino acids of a peptide linker may be introduced after the start codon of (e.g., adjacent to and in frame with) a gene encoding a protein. In other embodiments, a protein with a peptide linker may be synthesized by introducing, to the 3' end of a gene encoding the protein, codons encoding specific amino acid residues (e.g., two cysteine residues). For example, codons encoding amino acids of a peptide linker may be introduced before the stop codon of (e.g., adjacent to and in frame with) a gene encoding a protein.

Nanoparticle-Polypeptide Conjugates

Aspects of the present disclosure provide a nanoparticle linked to a polypeptide, referred to herein as a "nanoparticle-polypeptide conjugate." A polypeptide may be linked (e.g., attached to, or coupled to) a nanoparticle directly or indirectly.

Some aspects of the present disclosure provide methods for achieving rapid and robust conjugation of a polypeptide (e.g., protein) to a nanoparticle comprising a core-only or a core-shell structure, where the overcoating shell includes a semiconductor material that serves to, for example, protect and passivate the core and, in some instances, prevent leaching. In some embodiments, provided herein are methods of conjugating a polypeptide (e.g., protein) to nanocrystalline particles commonly referred to as colloidal quantum dots. Quantum dots may, in some embodiments, be synthesized from binary mixtures or II-VI, III-V and IV-VI semiconductor materials (e.g., ZnS, ZnSe, CdS, CdSe, CdTe and/or InP), as provided herein.

A conjugation method of the present disclosure includes synthesizing a nanoparticle core. In some embodiments, the nanoparticle core comprises a semiconductor material. Methods of synthesizing nanoparticle cores that comprise semiconductor materials are known in the art and may be used as provided herein.[21, 38] The synthesis of monodisperse quantum dots, for example, may be achieved by using the pyrolysis of organometallic precursors in the presence of hydrophobic coordinating ligands in organic media (Donega, C. D. *Chem. Soc. Rev.* 2011, 40, 1512; Murray, C. B. et al., *Annu. Rev. Mater. Sci.* 2000, 30, 545; and Dabbousi, B. O., et al., *J. Phys. Chem. B* 1997, 101, 9463). The present disclosure also contemplates the direct synthesis of hydrophilic quantum dots in aqueous solutions.

In some embodiments, nanoparticle cores are synthesized with one or more carboxylic acid(s) having alkane or alkene chains. In some embodiments, the carboxylic acid has 5 or more (e.g., 5, 6, 7, 8, 9, 10 or more) carbon atoms in an alkane or alkene chain. Examples of carboxylic acids for use in accordance with the present disclosure include, without limitation, oleic acid, hepatic acid, ethylhexanoic acid, linoleic acid, arachidic acid, valeric acid, caproic acid, enanthic acid, caprylic acid, pelargonic acid, capric acid, undecylic acid, lauric acid, tridecylic acid, myristic acid, palmitic acid, margaric acid and stearic acid.

In some embodiments, for example, in which the synthesized nanoparticle cores are hydrophobic (or insoluble), the synthesized nanoparticles are further solubilized to yield hydrophilic nanoparticle cores. In some embodiments, cap exchange, or ligand exchange, is used to solubilize the nanoparticle cores. Ligand exchange includes, for example, the replacement of carboxylic acids (e.g., with long alkane or alkene chains) with bifunctional ligands on a surface of the nanoparticle (e.g., nanoparticle core). The surface of the nanoparticle core may, in some embodiments, be exchanged with bifunctional ligands that attach to the nanoparticle at one end by, for example, thiol interactions, and provide solubility at the other through functional groups such as carboxylates or PEGs. Examples of other bifunctional agents include, without limitation, 3-mercaptopropionic acid, L-cysteine, mercaptosuccinic acid, 11-mercaptoundecanoic acid and L-glutathione.

Solubilized nanoparticle cores may then be combined, in solution, with semiconductor precursors and a polypeptide comprising a peptide linker, as provided herein. A "semiconductor precursor," as used herein, refers to any substance that can produce a semiconductor material (e.g., CdS or ZnS) when heated (e.g., at least 80° C. or at least 90° C.). This combination, or reaction mixture, is then incubated under conditions that permit formation of a semiconductor shell around the solubilized nanoparticle core and conjugation of the polypeptide to a surface of the semiconductor shell through a peptide linker to yield nanoparticle-polypeptide conjugates.

Parameters affecting conditions that permit formation of a semiconductor shell around a solubilized nanoparticle core and conjugation of a polypeptide to a surface of the semiconductor shell through a peptide linker include time and temperature. Other parameters include the ratio of nanoparticle to polypeptide in the reaction mixture.

In some embodiments, a reaction mixture is incubated (or heated) for a period of at least 10 minutes. For example, a reaction mixture may be incubated (or heated) for a period of 10 minutes to 60 minutes, or more. In some embodiments, a reaction mixture is incubated (or heated) for a period of 10 to 20 minutes, 10 to 30 minutes, 10 to 40 minutes, 10 to 50 minutes, 20 to 30 minutes, 20 to 40 minutes, 20 to 50 minutes, 20 to 60 minutes, 30 to 40 minutes, 30 to 50 minutes, 30 to 60 minutes, 40 to 50 minutes, 40 to 60 minutes or 50 to 60 minutes. In some embodiments, a reaction mixture is incubated (or heated) for a period of 10, 15, 20, 25, 30, 35, 40, 45, 50, 55 or 60 minutes. In some embodiments, a reaction mixture is incubated (or heated) for a period of 30 minutes. The period of time during which a reaction mixture is incubated (or heated) may depend of the composition and properties of the nanoparticle (see Methods). For example, a quantum dot with a photoluminescence emission peak at 720 nm may require a longer incubation time relative to a quantum dot with a with a photoluminescence emission peak at 520 nm.

In some embodiments, a reaction mixture is incubated at a temperature of at least 80° C. For example, a reaction mixture may be incubated at a temperature of 80° C. to 100° C. In some embodiments, a reaction mixture is incubated at a temperature of 80° C. to 90° C., or 90° C. to 100° C. In some embodiments, a reaction mixture is incubated at a temperature of 80° C., 85° C., 90° C., 95° C. or 100° C. In some embodiments, a reaction mixture is incubated at a temperature of 90° C. Following heating, the reaction may be cooled (e.g., in an ice bath), for example, to stop the reaction.

The ratio of nanoparticle to polypeptide in a reaction mixture may vary depending, for example, on the surface area of the nanoparticle and the size of the polypeptide. That is, the ratio of nanoparticle to polypeptide in the reaction mixture may depend on the valency of the conjugates. In some embodiments, the ratio of nanoparticle to polypeptide in a reaction mixture ranges from 1:100 to 1:1. For example, the ratio of nanoparticle to polypeptide in a reaction mixture may be 1:100, 1:90, 1:80, 1:70, 1:60, 1:50, 1:40, 1:30, 1:20, 1:10, 1:5 or 1:1. In some embodiments, the ratio of nanoparticle to polypeptide in a reaction is 1:20. Other nanoparticle to polypeptide ratios are contemplated herein.

In some embodiments, nanoparticle-polypeptide conjugates are purified. For example, nanoparticle-polypeptide conjugates may be purified by filtration, such as ultrafiltration. Other purification methods, for example, chromatographic methods, may be used.

Contemplated herein are a variety of uses for the nanoparticle-polypeptide conjugates provided herein. For example, nanoparticle-polypeptide conjugates may be used as sensors or probes, for cellular delivery, for in vivo imaging and diagnostics, and for bioelectronics as well as molecular memory (see, e.g., Medintz, I., et al., *Nat. Mater.* 2005, 4, 435; Bakalova, R., et al. *Nat. Biotechnol.* 2004, 22, 1360; Bakalova, R., et al. *Nat. Photonics* 2007, 1, 487; Portney, N. G., et al., *ACS Nano* 2008, 2, 191; and Blum, A. S., et al., *IEEE Trans. NanoBiosci.* 2007, 6, 270). While many aspects and embodiments of the invention describe the use of nanoparticle-polypeptide conjugates in the self-assembly of scaffolds, it should be understood that the invention is not so limited.

Polypeptide-Displaying Biopolymers

Aspects of the present disclosure provide a biopolymer linked to a polypeptide, referred to herein as a "polypeptide-displaying biopolymer." In some embodiments, a biopolymer, or a protein subunit thereof (e.g., a CsgA protein subunit) is linked to a peptide, also referred to herein as a "peptide tag," in which case, such a configuration may be referred to herein as a "tag-displaying biopolymer." In other embodiments, a biopolymer, or a protein subunit thereof (e.g., a CsgA protein subunit) is linked to a protein, in which case, such a configuration may be referred to herein as a "protein-displaying biopolymer." A "biopolymer" herein refers to a polymer that is composed of repeating structural units and that can be synthesized by a cell (e.g., a recombinant bacterial cell). Several non-limiting examples of polymers that are compatible with aspects of the present disclosure are amyloids, pili and flagella. As used herein, an "amyloid" refers to an aggregate of proteins or peptides with cross-beta structure and fibrillar morphology. Amyloid fiber structure includes of fl-strands which are perpendicular to the fiber axis and fl-sheets which stack parallel to the fiber axis. It should be appreciated that any kind of polymer expressed by a cell can be compatible with aspects of the present disclosure.

In some embodiments, a cell is genetically engineered to express at least one biopolymer that assembles into a nanostructure on the surface of the cell, outside the cell or inside the cell. In some embodiments, the biopolymer is an amyloid, pilus or flagellum. A biopolymer may be modified or unmodified. In some embodiments, the cell is a bacterial cell, fungal cell (including a yeast cell) or mammalian cell. In some embodiments, the cell is a bacterial cell, such as a cell of the *Escherichia, Salmonella, Pseudomonas, Bacillus, Citrobacter, Shigella* or *Enterobacter* genus. For example, the cell may be an *Escherichia coli* (*E. coli*) cell, a *Pseudomonas aeruginosa* (*P. aeruginosa*) cell or a *Bacillus subtilis* (*B. subtilis*) cell.

In some embodiments, the cell is an *E. coli* cell, and the biopolymer is an amyloid fiber, such as a curli amyloid fiber. In some embodiments, curli fibers are optimally expressed naturally in conditions that include temperatures below 30° C., low osmolarity, nutrient limitation, stationary phase, and a microaerophilic environment (Barnhart et al., *Annu Rev Microbiol* 60:131 (2006)). Methods of expressing biopolymers, such as curli amyloid fibers, are described in International Publication No. WO 2012/166906, incorporated by reference herein in its entirety.

The *E. coli* curli operon comprises csgBAC and csgDEFG. The csgBAC transcriptional unit is positively regulated by CsgD and negatively regulated by the CpxA/CpxR system and Rcs, both of which are responsive to membrane stress. Id. Positive regulators of the csgDEFG transcriptional unit include the OmpR/EnvZ system, RpoS, Crl, MlrA, and IHF while negative regulators include the CpxA/CpxR system and the Rcs system. Id.

CsgA, which is the major curlin subunit, is secreted as a soluble protein. CsgA is polymerized into fibrils by CsgB, which is the minor curlin subunit and is an outer-membrane-associated protein. CsgA and CsgB share sequence homology and form a cross-β sheet complex with five repeating strand-loop-strand structures. Both CsgA and CsgB can form amyloid fibrils on their own (Shewmaker et al., *J Biol Chem* 284:25065 (2009); Barnhart et al., *Annu Rev Microbiol* 60:131 (2006)).

CsgD is a positive regulator of csgBAC expression. CsgE is a chaperone-like protein thought to be involved in the stability of CsgA and CsgB. CsgF is a chaperone-like protein which is secreted to the cell surface and is involved in associating CsgB with the cell surface helping CsgB nucleate curli fiber formation (Nenninger et al., *Proc Natl Acad Sci USA* 106:900 (2009)). CsgG is a lipoprotein which participates in the secretion of CsgA, CsgB, and CsgF (Id.; Epstein et al., *JBacteriol* 191:608 (2009)). CsgG interacts with the N22 domain of CsgA to mediate secretion to the cell surface (Chapman et al., *Science* 295:851 (2002)).

It should be appreciated that the genes encoding amyloid fibers can be obtained from a variety of sources. A non-limiting example of a homologous operon to the *E. coli* Csg operons includes the agfoperon in *Salmonella* (Darwin et al. *Clin Microbiol Rev* 12:405-428 (1999)). Related operons have also been identified in *Pseudomonas* (Dueholm et al. *Mol Microbiol* Epub Jun. 21 (2010)) and in *Bacillus subtilis* (Romero et al., *Proc Natl Acad Sci USA* 107:2230-2234 (2010)), comprising the fap and Tas operons, respectively.

Functional amyloids have also been identified in yeast. For example, in *Candida albicans*, the Als Adhesins have been demonstrated to form amyloid-like fibers (Otoo et al., *Eukaryotic Cell* 7:776-782 (2008)). Amyloid formation has also been demonstrated for adhesion proteins in *Saccharomyces cerevisiae* (Ramsook et al. *Eukaryotic Cell* 9:393-404 (2010)). Rep1-1 to Rep1-11 peptides have also been shown to form surface-active amyloid fibrils in fungi (Teertstra et al., *J Biol Chem* 284:9153-9159 (2009)).

Aspects of the present disclosure provide methods of engineering cells (e.g., bacterial cells such as *E. coli* cells) to produce biopolymers displaying polypeptides (e.g., heterologous peptides).[43-44] A polypeptide may be, for example, a protein or a peptide. Protein-displaying biopolymers of provided herein, in some embodiments, express one of a pair of protein-protein or protein-peptide binding partners (e.g., SpyTag of the SpyCatcher-SpyTag binding pair). In some embodiments, a polynucleotide (e.g., DNA) encoding a desired polypeptide may be appended to the 3' end of a polynucleotide encoding a protein subunit (e.g., protein subunit such as CsgA) of a biopolymer. In other embodiments, a polynucleotide encoding a desired polypeptide may be appended to the 5' end of a polynucleotide encoding a protein subunit of a biopolymer.

In some embodiments, a protein-displaying biopolymer assembles (e.g., from protein-displaying subunits as shown in FIG. 1A) at the surface of a cell, while in other embodiments, a protein-displaying biopolymer assembles inside the cell or outside the cell. Assembly of biopolymers, such as amyloid fibrils, is described in International Publication No. WO 2012/166906, incorporated by reference herein in its entirety. In some embodiments, protein-displaying subunits of biopolymers are produced in a cell, subsequently purified, and then assembled in vitro into protein-displaying biopolymers.

As used herein, the term "nucleic acid" refers to at least two nucleotides covalently linked together, and in some instances, may contain phosphodiester bonds (e.g., a phosphodiester "backbone"). In some embodiments, a nucleic acid may be considered to be a nucleic acid analog, which may contain other backbones comprising, for example, phosphoramide, phosphorothioate, phosphorodithioate, O-methylphophoroamidite linkages, and/or peptide nucleic acids. Nucleic acids (e.g., components, or portions, of the nucleic acids) may be naturally occurring or engineered. Engineered nucleic acids include recombinant nucleic acids and synthetic nucleic acids. "Recombinant nucleic acids" may refer to molecules that are constructed by joining nucleic acid molecules and, in some embodiments, can replicate in a living cell. "Synthetic nucleic acids" may refer to molecules that are chemically or by other means synthesized or amplified, including those that are chemically or otherwise modified but can base pair with naturally occurring nucleic acid molecules. Recombinant and synthetic nucleic acids also include those molecules that result from the replication of either of the foregoing.

In some embodiments, a nucleic acid encoding a protein subunit of a biopolymer (e.g., csgBAC and/or csgDEFG) is expressed in a cell on a plasmid under the control of an inducible promoter. It should be appreciated that a cell that expresses such plasmids may also express endogenous copies of the nucleic acid (e.g., csgBAC and/or csgDEFG). Alternatively, in some embodiments, endogenous copies of the nucleic acid (e.g., csgBAC and/or csgDEFG) are mutated or deleted (e.g., knocked out). A variety of inducible promoters may be used as provided herein. As used herein, an "inducible promoter" is one that is characterized by initiating or enhancing transcriptional activity when in the presence of, influenced by or contacted by an inducer or inducing agent. In some embodiments, inducible synthetic promoters such as pLtetO, which is induced by anhydrotetracycline (aTc), or pLlacO, which is induced by isopropyl β-D-1-thiogalactopyranoside (IPTG) (Lutz et al., *Nucleic Acids Res* 25:1203 (1997)) is used. In some embodiments, inducible synthetic promoters are regulated using non-transcription based regulators of gene expression. In some embodiments, the non-transcription based regulators of gene expression are riboregulators, such as LacI riboregulators, TetR riboregulators or LuxR riboregulators.

In some embodiments, a tightly regulated anhydrotetracycline (aTc)-inducible system[49] is used to express modified csgA genes.[44]

Cells described herein can endogenously express wild-type biopolymers, such as amyloid fibers, and can also be engineered to express modified biopolymers, such as amyloid fibers. A "modified biopolymer" expressed by a cell herein refers to a biopolymer that is different from a wild-type biopolymer. In some embodiments, a modified biopolymer has at least one nucleotide difference in its nucleic acid sequence relative to a wild-type biopolymer. In some embodiments, a modified biopolymer has at least one amino acid difference in its protein sequence relative to a wild-type biopolymer. In other embodiments, a modified biopolymer does not have any amino acid differences relative to a wild-type biopolymer. In some embodiments, a modified biopolymer has a different three-dimensional structure than a wild-type biopolymer.

Figures 9A, 9B:
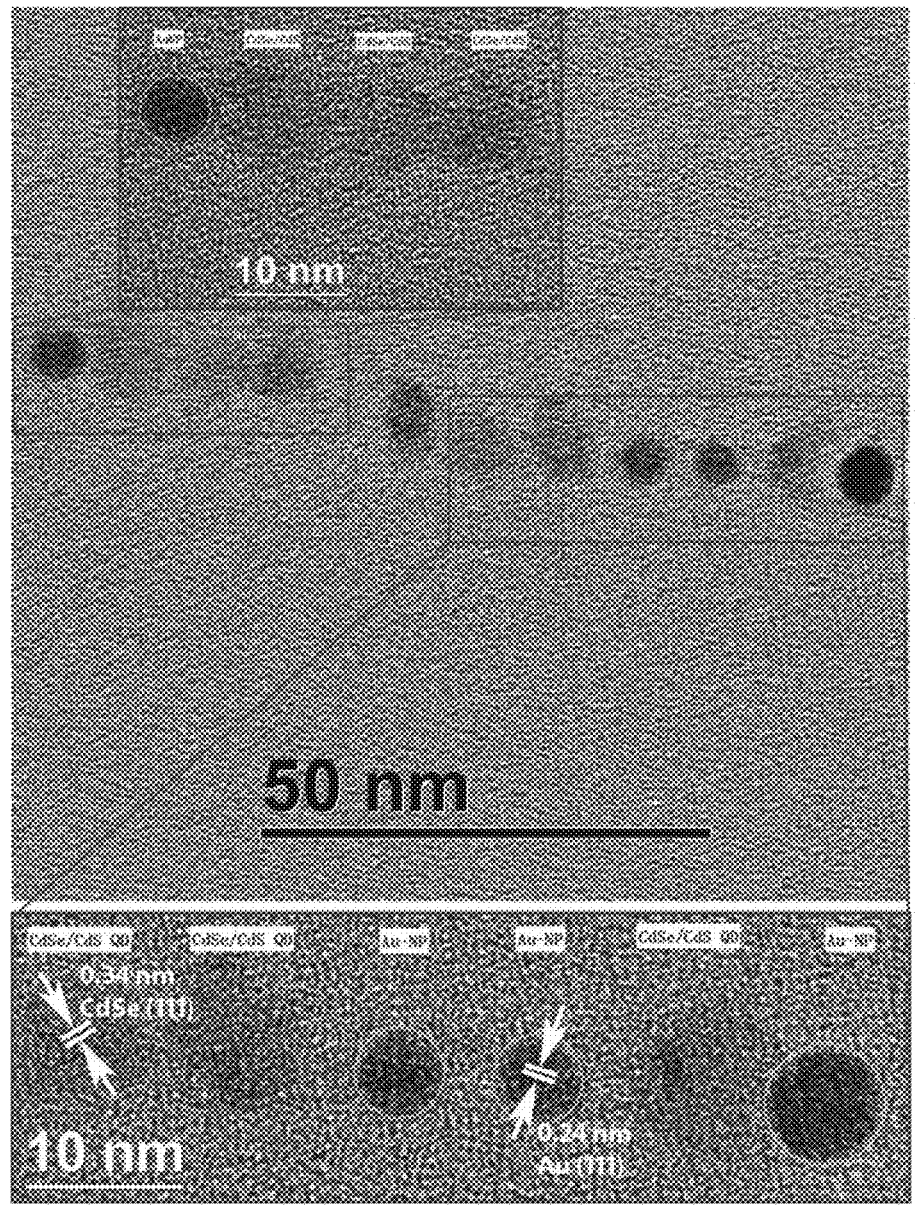
FIGS. 9A and 9B show enlarged TEM images of FIG. 7H, which shows that CdSe/CdS QD-pilin-C conjugates and Au-NiNTA NPs co-self-assembled onto amyloid fibrils of mixed $CsgA_{isopeptag}$ and $CsgA_{HisTag}$ subunits.
Figures 10A, 10B:
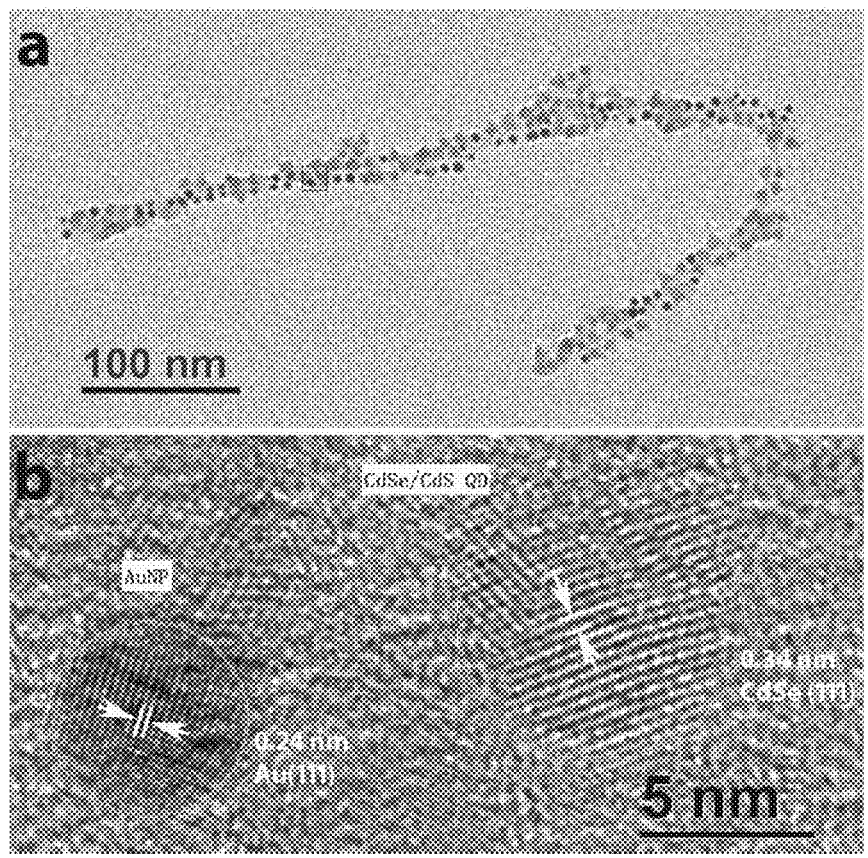
FIGS. 10A and 10B show additional TEM and HRTEM images of examples of CdSe/CdS QD-pilin-C conjugates and Au-NiNTA NPs co-self-assembled onto amyloid fibrils of mixed $CsgA_{isopeptag}$ and $CsgA_{HisTag}$ subunits; the enlarged image in FIG. 10B corresponds to the area outlined by a white square in FIG. 10A; the enlarged image in FIG. 10A corresponds to FIG. 7G.

Modified biopolymers, such as amyloid fibers, can be genetically engineered to contain heterologous polypeptides, as described herein. A biopolymer, such as an amyloid fiber, can contain two or more heterologous polypeptides, which can be the same as or different from each other. In some embodiments, a biopolymer, such as an amyloid fiber, contains 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more than 50 heterologous polypeptides. In some embodiments, heterologous polypeptides within a biopolymer are the same, while in other embodiments, heterologous polypeptides within a biopolymer are different from each other. For example, FIGS. 9A and 9B show TEM images of "dual-tag-displaying" amyloid fibrils of mixed $CsgA_{isopeptag}$ and $CsgA_{HisTag}$ subunits (see Example 2). Thus, simultaneous expression of different protein subunits can create modified biopolymers (e.g., amyloid fibers) that have interdigitated, interspersed, and different functional polypeptides.

In some embodiments, the genetic sequence of a biopolymer, such as an amyloid fiber, is modified such that it contains nucleic acid sequences encoding for at least one heterologous polypeptide. In some embodiments, at least one peptide binding partner is introduced into a biopolymer, such as an amyloid fiber. For example, at least one SpyTag or isopeptag peptide may be introduced into a biopolymer, such as an amyloid fiber. In some embodiments, a polypeptide is expressed in the cell independently from the biopolymer, is secreted from the cell, and then interacts with the biopolymer on the cell surface.

In some embodiments, the endogenous gene encoding a protein subunit of the biopolymer is knocked out (removed or inactivated) in cells to ensure that all biopolymers formed are composed of genetically engineered subunits. In some embodiments, the endogenous csgA gene is knocked out (ΔcsgA) to ensure that all amyloid fibrils formed are composed of genetically engineered CsgA subunits. In some embodiments, cells are mutated. For example, in some embodiments, an ompR234 mutation is introduced to cells to enable fibril production in liquid media.[51]

Self-Assembly of Nanoparticle-Polypeptide Conjugates with Polypeptide-Displaying Biopolymers.

Aspects of the present disclosure provide compositions that include at least one nanoparticle linked to a first polypeptide, and a biopolymer linked to at least one second polypeptide that binds covalently to the first polypeptide. Upon binding of the first and second polypeptides, a scaffold is formed. FIG. 1A depicts one embodiment of the synthesis and assembly of such a scaffold. Recombinant *E. coli* cells (*E. coli* #1) are engineered to express SpyCatcher protein fused to a peptide linker, $Cys_2$. The expressed tagged proteins, $Cys_2$-SpyCatcher, are collected and conjugated to quantum dots (QDs) during shell synthesis of the QDs such that the $Cys_2$-SpyCatcher proteins are conjugated to an external surface of the shell of the QD, thereby producing a QD-$Cys_2$-Spycatcher conjugate. A separate population of recombinant *E. coli* cells (*E. coli* #2) is engineered to express CsgA protein subunits fused to a peptide tag, Spytag. Assembly of theses Spytag-displaying CsgA subunits forms a chain-like structure. Upon binding of SpyCatcher protein to Spytag peptide, the chain-like structure is populated with QDs.

Nanoparticle-polypeptide conjugates can self-assemble with polypeptide-displaying biopolymers by combining the two components (e.g., in buffer) at 20° C. to 30° C. (e.g., 25° C.) for at least 10 minutes. In some embodiments, the two components are combined for 10 to 60 minutes. For example, nanoparticle-polypeptide conjugates can self-assemble with polypeptide-displaying biopolymers when combined at 20° C. to 30° C. (e.g., 25° C.) for 10, 15, 20, 25, 30, 35, 40, 45, 50, 55 or 60 minutes, or more.

The ratio of biopolymer to conjugate ratio may vary depending, for example, on the diameter of the nanoparticle-polypeptide conjugates and the length of the polypeptide-displaying biopolymer. In some embodiments, the ratio of biopolymer to conjugate in a reaction mixture ranges from 1:1000 to 1:1. For example, the ratio of biopolymer to conjugate in a reaction mixture may be 1:1000, 1:900, 1:800, 1:700, 1:600, 1:500, 1:400, 1:300, 1:200, 1:100, 1:50, 1:10 or 1:1. In some embodiments, the ratio of biopolymer to conjugate in a reaction mixture is 1:200. Other biopolymer to conjugate ratios are contemplated herein.

In some embodiments, higher-order structures self-assembled from nanoparticle-polypeptide conjugates and polypeptide-displaying biopolymers are purified. For example, the structures may be purified by centrifugation, or filtration (e.g., with a 0.1/0.2/0.5 micron (pore size) column or with Amicon® columns (e.g., 30 kDa or 100 kDa cut off)).

Additional aspects and embodiments of the present disclosure are described below by way of several non-limiting examples.

Higher-order structures containing nanoparticle-polypeptide conjugates and polypeptide-displaying biopolymers, also referred to herein as nanostructures, in some embodiments, may be rationally designed. A nanostructure is considered to be "rationally-designed" if one or more of its structural parameters (e.g., shape and/or size, include height, width, length, diameter) is determined prior to production of the nanostructure. In general, rational design is a method of creating new molecules with a certain functionality, based on the ability to predict how the molecules' structure will affect their behavior through physical models.

Examples of rationally-designed nanostructures are shown in Example 4. Thus, in some embodiments, recombinant cells growth is constrained to a defined shape or pattern (e.g., stencil) such that the shape or pattern formed by the growing cells determines the shape or pattern of the resulting nanostructure formed by self-assembly of nanoparticle-polypeptide conjugates and polypeptide-displaying biopolymers produced by the cells.

Assembly of Functional Optoelectronic Devices

Various aspects of the present disclosure contemplate the production of optoelectronic devices (e.g., field-effect transistors) using nanoparticle-polypeptide conjugates and polypeptide-displaying biopolymers. In some embodiments, methods of producing optoelectronic devices include (a) culturing on a dielectric layer of a substrate recombinant bacterial cells that express (i) a first polynucleotide encoding a subunit of a biopolymer linked to a first peptide tag and (ii) a second polynucleotide encoding a subunit of a biopolymer linked to a second peptide tag, wherein the substrate contains a gate electrode on a surface of the substrate, (b) contacting the recombinant bacterial cells with (iii) a carbon nanotube linked to a first protein that forms a covalent isopeptide bond with the first peptide tag and (iv) a nanoparticle linked to a second protein that forms a covalent isopeptide bond with the second tag, and (c) depositing onto recombinant bacterial cells of (b) a source electrode and a draw electrode, thereby producing an optoelectronic device.

An "optoelectronic device" refers to an electronic device that sources, detects and controls light (e.g., visible light, gamma rays, X-rays, ultraviolet and infrared). Phototransistors, such as field-effect transistors, are examples of optoelectronic devices.

A "substrate" refers to a surface that can be modified to contain a dielectric layer and at least one electrode. In some embodiments, a substrate comprises or is glass, silica, silicon, nitride, paper, gallium arsenide, germanium, silicone, polydimethylsiloxane (PDMS), polycarbonate, poly(methyl methacrylate), zeonax, cyclic olefin polymer (COP), polyester toner (PeT) or cellulose. In some embodiments, a substrate comprises silicon.

A "dielectric layer" refers to a layer of a substrate (e.g., a membrane layer) that can be polarized by an applied electric field. In some embodiments, a dielectric layer comprises or is at least one of alumina ($Al_2O_3$), silicon dioxide ($SiO_2$), hafnium oxide ($HfO_2$), titanium oxide ($TiO_2$), titanium nitride (TiN), graphene, hexagonal boron nitride (hBN), silicene, zinc oxide (ZnO), indium arsenide (InAs), bismuth selenide (BiSe), bismuth telride ($BeTe_2$), lead selenide ($PbSe_2$), nickel silicide (NiSi), tungsten diselenide ($WSe_2$), copper oxide (CuO), gallium nitride (GaN), molybdenum disulfide ($MoS_2$), niobium diselenide ($NbSe_2$), and $Bi_2Sr_2CaCu_2O$. Dielectric layers may comprise other semiconductor materials.

A "carbon nanotube" refers to an allotrope of carbon with a cylindrical nanostructure. The size of a carbon nanotube may be nanometer or micrometer in size. In some embodiments, the length-to-diameter ratio of a carbon nanotube is 10:1 to 10,000:1 (e.g., 10:1 to 100:1, 10:1 to 500:1, 10:1 to 1000:1, 10:1 to 5000:1). A carbon nanotube may be single-walled or multi-walled. Other carbon nanotubes sizes and structures are contemplated herein.

A "gate electrode" refers to the electrode of a semiconductor (e.g., metal oxide semiconductor) optoelectronic device (e.g., field-effect transistor) that controls the flow of electrical current between the source and the drain of the device. In some embodiment, the gate electrode comprises gallium-indium eutectic or other liquid metal alloy. In some embodiments, the source and drain of a device comprises, or is, a silver paste.

EXAMPLES

Example 1

This Example describes the synthesis of CdSe/CdS core/shell quantum dot (QD)-SpyCatcher conjugates and their self-assembly on genetically encoded curli amyloid fibrils via specific SpyTag-SpyCatcher chemistry.

Figures 2A, 2B:
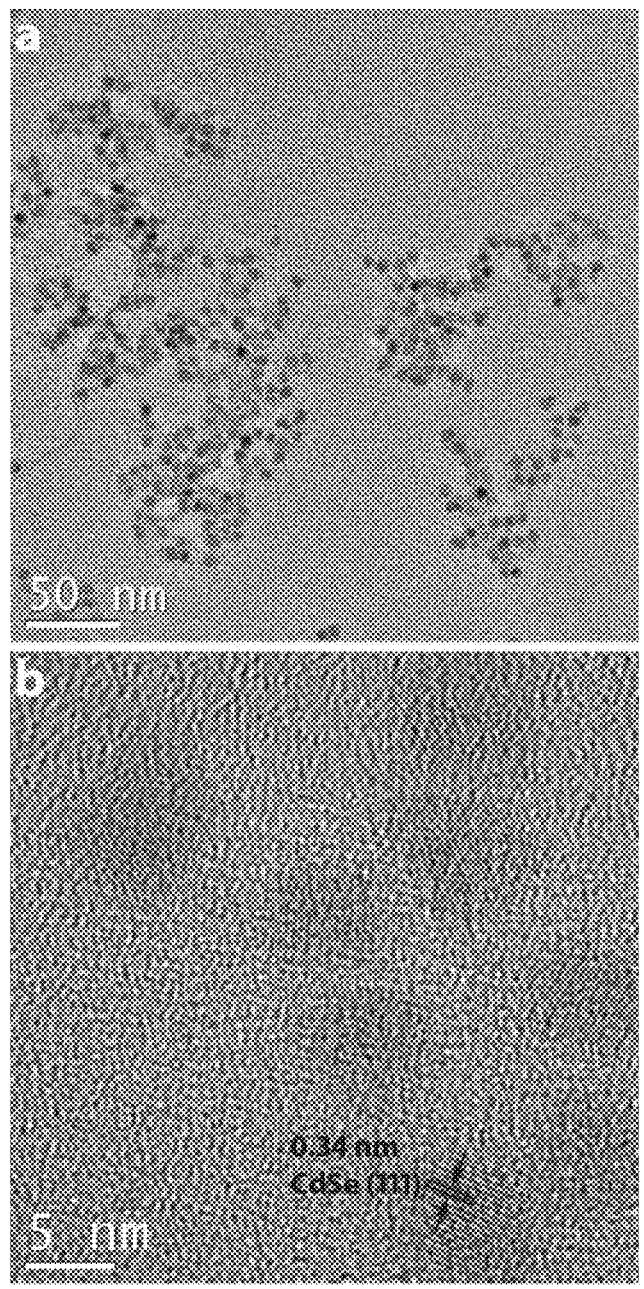
FIGS. 2A and 2B show examples of transmission electron microscopy (TEM) and high-resolution TEM (HRTEM) images of the CdSe/CdS QD-SpyCatcher conjugates.

Conjugates of CdSe/CdS QD-SpyCatcher were generated by attaching $Cys_2$-SpyCatcher proteins to QDs during the core/shell QD synthesis process (see Methods below). Oleic-acid-capped 6 nm CdSe QDs with a photoluminescence emission peak at 650 nm[38] (FIGS. 1B-1D) were first synthesized, and mercaptopropionic acid was added to make the CdSe QDs water-soluble. $Cys_2$-SpyCatcher proteins were then produced by genetically engineered *E. coli*, purified, added to shell-formation precursors and the water-soluble CdSe QDs, and gently heated at 90° C. for 30 minutes. The resulting CdSe/CdS QD-SpyCatcher conjugates, with ~8 nm diameters (FIGS. 2A and 2B), were purified and re-dispersed in 1× phosphate buffered saline (PBS). The organic-ligand-capped CdSe QDs displayed weak photoluminescence (FIG. 1H, bottom trace, no peak), while the Spy-Catcher-conjugated CdSe/CdS QDs exhibited much stronger photoluminescence with quantum yields of 35% (FIG. 1H, top trace, with peak). The enhanced photoluminescence emission can be attributed to CdS shell formation during the conjugation process. The energy dispersive spectroscopy (EDS) spectra of the starting CdSe QDs and assembled QD chains revealed the presence of Cd and Se from the QD core, S from the QD shell, and U from the stained amyloids (FIG. 1I).

In addition to the 5 nm red CdTe/CdS QD-SpyCatcher conjugates (650 nm, quantum yield of 67%), 3 nm green CdTe/CdS QD-Pilin-C conjugates (530 nm, quantum yield of 30%) and 4 nm blue ZnCdSe/ZnS QD-Pilin-N conjugates (440 nm, quantum yield of 32%) were generated (FIGS. 15A-15H and 16A-16B).

Figure 3:
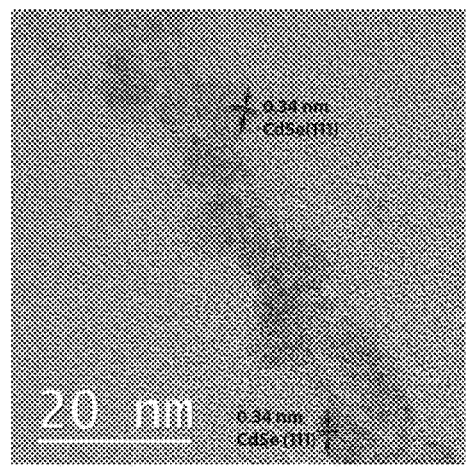
FIG. 3 shows an enlarged TEM image of FIG. 1M with CdSe/CdS QD-SpyCatcher conjugates self-assembled onto SpyTag-displaying amyloid fibrils.
Figures 4A, 4B, 4C:
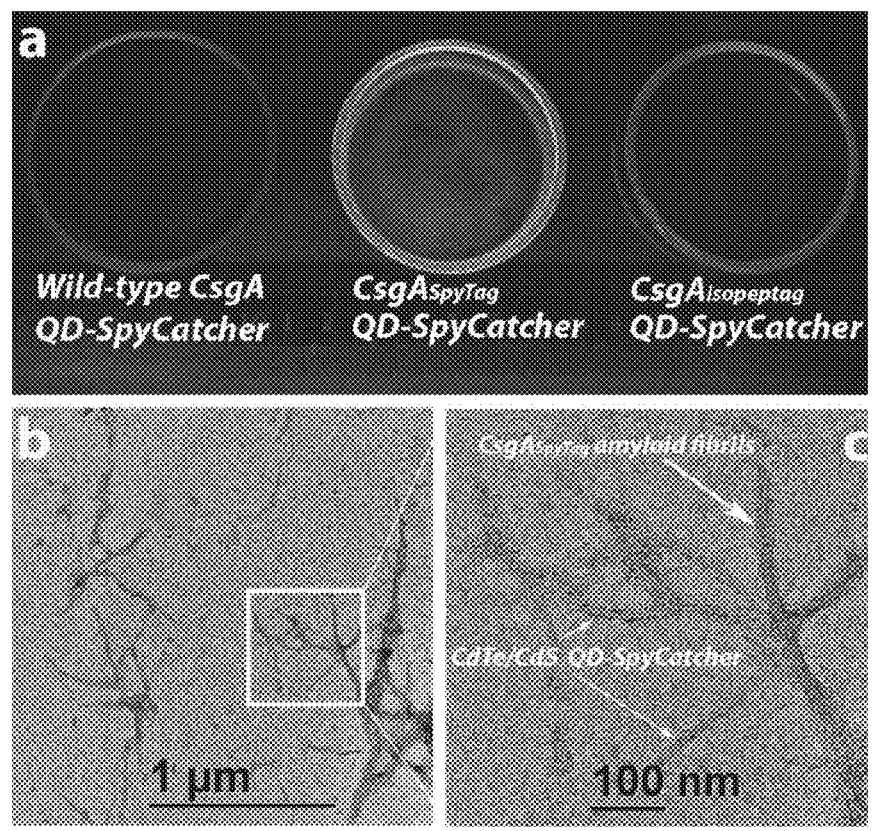
FIGS. 4A-4C show examples of wild-type (top left, FIG. 4A), SpyTag-displaying (top middle, FIG. 4A), and isopeptag-displaying (top right, FIG. 4A) curli amyloid fibrils self-assembled with 650-nm emitting CdTe/CdS QD-SpyCatcher conjugates in 6-cm diameter glass dishes.

Micron-level one-dimensional (1D) self-assembly of QDs was achieved by taking advantage of high-fidelity coupling between SpyCatcher on the CdSe/CdS QDs and SpyTag displayed on extracellular curli amyloid fibrils. To this end, *E. coli* cells that secrete CsgA$_{SpyTag}$ were engineered, resulting in the formation of SpyTag-displaying curli amyloid fibrils. For the self-organization of 1D QD chains, CdSe/CdS QD-SpyCatcher conjugates were incubated with SpyTag-encoded fibrils in 1×PBS at room temperature for 30 minutes to permit complete SpyTag-SpyCatcher coupling. Low-magnification TEM, HRTEM, and STEM images show that the 8 nm CdSe/CdS QDs surrounded the amyloid fibrils (FIGS. 1E-1N and FIGS. 4A-4C). A high resolution TEM image of a single chain (FIGS. 1M and 1N, and FIG. 3) confirmed the successful formation of QD chain structures. One-dimensional QD chains were not produced in a control experiment where CdSe/CdS QD-SpyCatcher conjugates were mixed with amyloids that did not contain SpyTag (FIG. 1O). One-dimensional QD chains organized by SpyTag-displaying curli fibrils had lengths that were an order of magnitude longer (e.g., up to 3-4 microns) than typically achievable via DNA origami. For example, biotinylated DNA origami has been used to assemble streptavidin-conjugated CdSe/ZnS QDs into 1D chains, but is limited to lengths of 300-400 nm due to the size of the M13 phage genome.[39] The ability to organize functional nanoparticles at the micron-level may be important for realizing the potential of nanophotonic and nanoelectronic devices.

FIG. 1A shows a schematic illustrating the conjugation strategy that involves expressing Cys2-SpyCatcher from bacteria (*E. coli* #1) and conjugating it with QDs during shell synthesis. Combining functionalized QDs with SpyTag-displaying curli amyloid fibrils synthesized by bacteria (*E. coli* #2) resulted in the self-assembly of 1D QD chains. FIGS. 1B-1D show TEM, HRTEM, and STEM images of the starting CdSe core QDs before conjugation. The circle in FIG. 1C indicates a single 6 nm CdSe QD. FIGS. 1E-1G show TEM and STEM images of QD-SpyCatcher conjugates self-assembled on SpyTag-displaying amyloid fibrils (inset FIG. 1F is from the marked square area in FIG. 1G). FIGS. 1H and 1I show photoluminescence emission spectra and EDS spectra of the same amount of CdSe core QDs (FIG. 1H, no peak; FIG. 1I, top trace) and QD-SpyCatcher conjugates (FIG. 1H, peak; FIG. 1I, bottom trace). The inset in FIG. 1H shows pictures of the QDs before (left) and after (right) conjugation with SpyCatcher. FIGS. 1J-1N show higher magnification TEM, STEM, and HRTEM images for self-assembled 1D QD structures on curli amyloids via SpyTag-SpyCatcher interactions (the image in FIG. 1M is from the marked square area in FIG. 1K; the image FIG. 1N is from the marked square area in FIG. 1M). The circle in FIG. 1N indicates a single 8 nm CdSe/CdS core/shell QD. FIG. 1O shows a TEM image of non-SpyTag-displaying wild-type curli amyloid fibrils (Table 1) after mixing with QD-SpyCatcher conjugates, demonstrating that no QDs are attached with the fibrils. The amyloid fibrils were visualized by negative staining with uranyl acetate.

Example 2

Figures 5A, 5B, 5C, 5D, 5E, 5F, 5G, 5H, 5I, 5J, 5K:
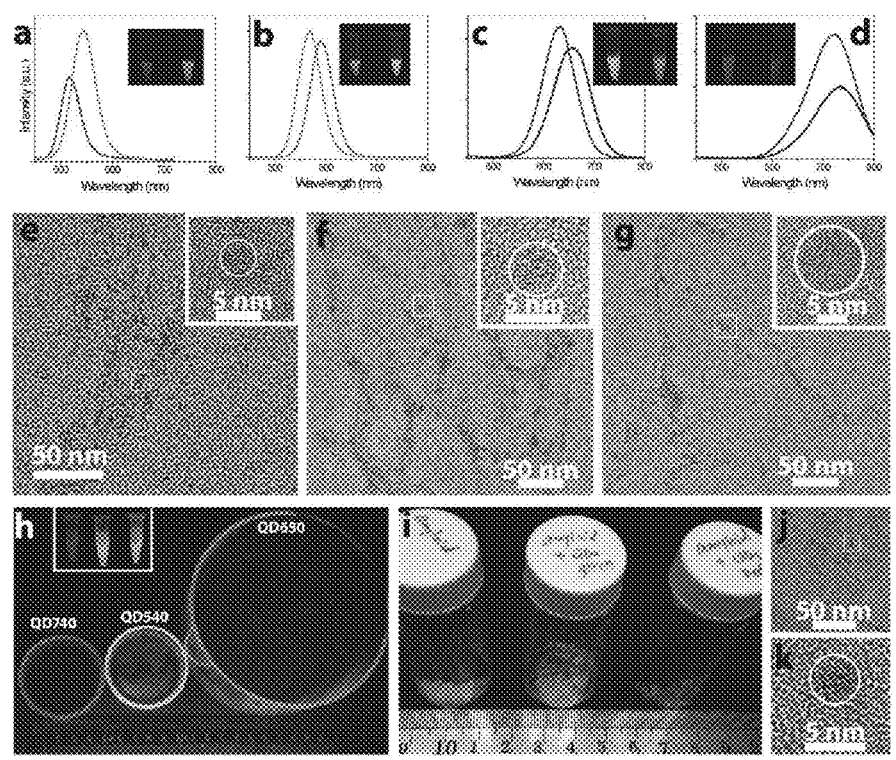
FIGS. 5A-5K show an example of the synthesis of CdTe/CdS core/shell QD-SpyCatcher with green, yellow, red, and near-infrared (NIR) photoluminescence emission and their self-assembly on SpyTag-displaying amyloid fibrils.
Figures 6A, 6B, 6C, 6D:
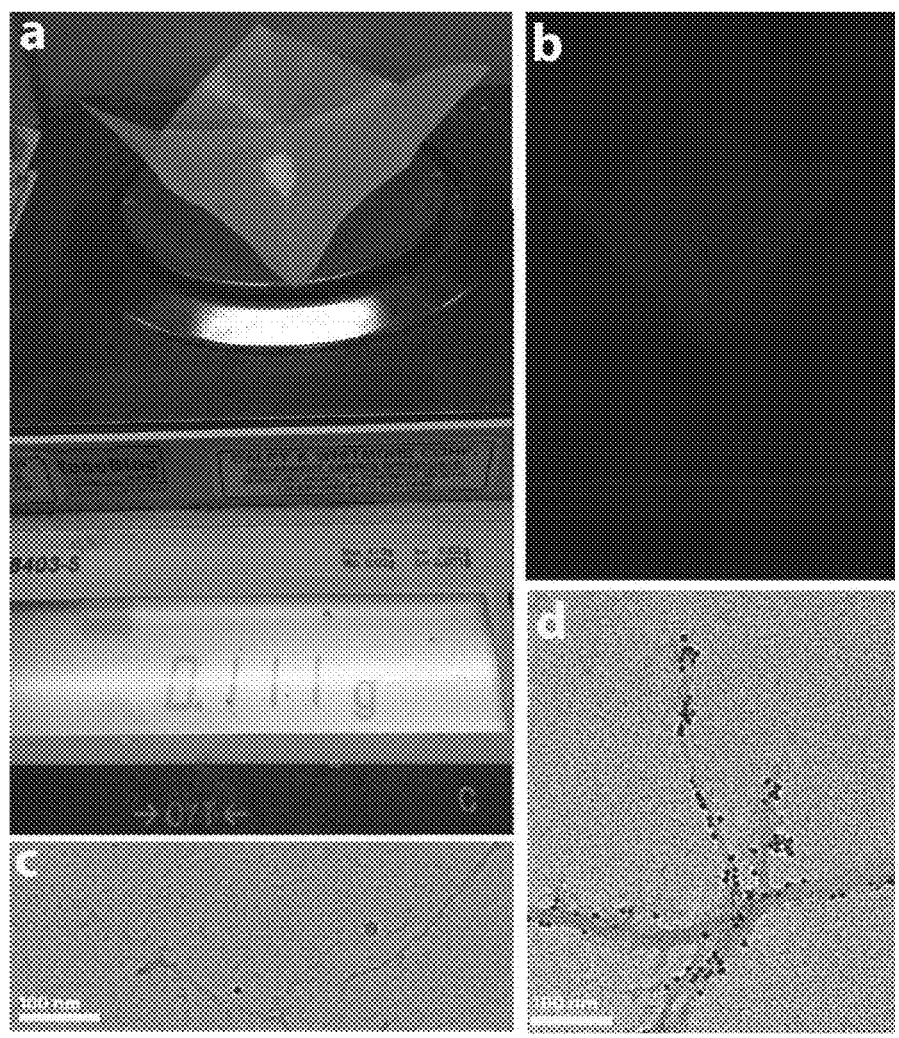
FIGS. 6A and 6B show an example of a large-scale synthesis of SpyTag-displaying amyloid fibrils (FIG. 6A, visible light.
FIGS. 6C and 6D show TEM images of freeze-dried SpyTag-displaying amyloid fibrils dispersed in buffer and then self-assembled with unconjugated CdSe/CdS core/shell QDs (FIG. 6C) and CdSe/CdS QD-SpyCatcher conjugates.

This Example describes the synthesis of CdTe/CdS core/shell QD-SpyCatcher with green, yellow, red, and near-infrared (NIR) photoluminescence emission and their self-assembly on SpyTag-displaying amyloid fibrils. The synthesis strategy for QD-SpyCatcher conjugates is versatile and generalizable to QDs with variable compositions and sizes. As shown in FIGS. 5A-5D, a series of CdTe/CdS core/shell QD-SpyCatcher conjugates were constructed with tunable photoluminescence emissions at 540, 590, 650, 740 nm, and with quantum yields of 43%, 56%, 65%, 38%, respectively. The 3 nm CdTe/CdS QD-SpyCatcher conjugates were achieved by coating 568 nm emission CdTe/CdS QDs with CdS shells in the presence of Cys2-SpyCatcher protein to form thicker-shell 590 nm emission CdTe/CdS QD-SpyCatcher conjugates (FIG. 5E). These 590 nm emission CdTe/CdS QD-SpyCatcher conjugates were self-assembled with SpyTag-displaying amyloid fibrils. Similarly, functionalization of 5 and 7 nm CdTe/CdS QDs with Cys2-SpyCatcher was achieved, and these red and near-infrared emission conjugates were organized on SpyTag-displaying amyloid fibrils (see FIGS. 5F and 5G, respectively). The red shift of the photoluminescence emission peak of CdTe/CdS core/shell QDs during the shell growth process is due to a transition from type-I to type-II QDs during the gradual growth of the CdS shell.[40-42]

Large-scale production of cell-synthesized SpyTag-displaying amyloid fibrils and Cys2-SpyCatcher protein for organizing QD-SpyCatcher conjugates was performed next. A 100-cm$^2$-scale self-assembly of CdTe/CdS QD-SpyCatcher conjugates on SpyTag-displaying curli amyloids synthesized by *E. coli* (FIG. 5H) was achieved. Self-organization only occurred in the presence of the SpyCatcher-SpyTag interaction. This was confirmed by the observation that wild-type and isopeptag-displaying curli amyloids did not bind significantly to QD-SpyCatcher (see FIG. 4C). Moreover, freeze-dried SpyTag-displaying amyloid fibrils were generated, both in the absence and presence of QD-SpyCatcher conjugates, at sub-gram scales (see FIG. 5I and FIG. 4A). In the absence of QD conjugates, the freeze-dried SpyTag-displaying amyloid fibrils showed no photoluminescence; however, when the amyloid fibrils were combined with green or red CdTe/CdS QD-SpyCatcher conjugates and then freeze-dried, the resulting self-assemblies exhibited stable and strong photoluminescence (FIG. 2I). The underlying nanostructures were retained after re-dispersing the freeze-dried powders in buffer (FIGS. 2J and 2K). Further, freeze-dried SpyTag-displaying amyloid fibrils were reconstituted in water and were able to organize QD-SpyCatcher conjugates, but could not organize unconjugated QDs (FIGS. 6A-6D).

FIGS. 5A-5D show photoluminescence emission spectra and the corresponding pictures (illuminated with a 365 nm UV lamp in the dark) for CdTe/CdS QDs before (left curves, with 520, 568, 620, and 720 nm emission peaks, respectively) and after (right curves, with 540 (green), 590 (yellow), 650 (red), and 740 (NIR) nm emission peaks, respectively) conjugation. FIGS. 5E-5G show TEM and HRTEM images (insets are from the rectangles marked in each figure) of the (FIG. 5E) yellow, (FIG. 5F) red, and (FIG. 5G) NIR CdTe/CdS QD-SpyCatcher conjugates (with emission peaks at 590, 650 nm, and 740 nm, respectively) self-assembled on SpyTag-displaying amyloid fibrils. FIG. 5H shows photographs (illuminated with a 365 nm UV lamp in the dark) of the green, red, and NIR CdTe/CdS QD-SpyCatcher conjugates (with emission peaks at 540, 650 nm, 740 nm, respectively) self-organized on SpyTag-displaying amyloid fibrils embedded in bacterial cultures on glass dishes. The inset image shows the QD-SpyCatcher conjugates (illuminated with a 365 nm UV lamp in the dark) prior to self-assembly with amyloids. FIG. 5 I shows photographs of freeze-dried SpyTag-displaying amyloid fibrils on their own (left), as well as the amyloid fibrils with green (middle) or red (right) CdTe/CdS QD-SpyCatcher conjugates under illumination with a 365 nm UV lamp under ambient light. FIGS. 5J and 5K show a TEM image and an HRTEM image (image in FIG. 5K is from the white rectangle marked in j) of amyloid fibrils with self-assembled 650 nm emission CdTe/CdS QD-SpyCatcher conjugates after freeze drying and subsequent resuspension in 1×PBS buffer. White circles in the images in FIGS. 5E-G and 5K mark single quantum dots.

Example 3

Figures 7A, 7B, 7C, 7D, 7E, 7F, 7G, 7H, 7I, 7J, 7K, 7L:
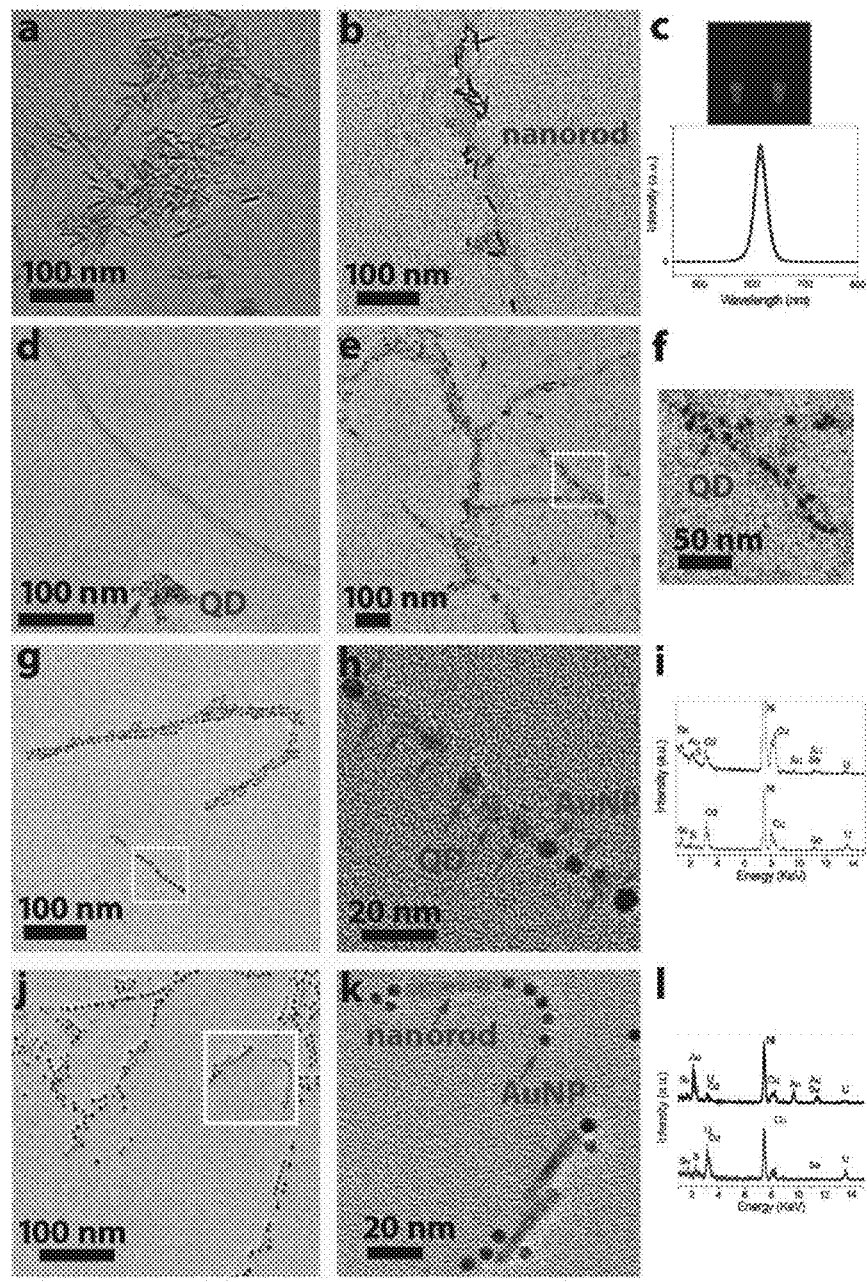
FIGS. 7A-7L show an example of the synthesis of CdSe/CdS core/shell nanorod-SpyCatcher and CdSe/CdS core/shell QD-pilin-C conjugates as well as their self-assembly and co-self-assembly with Au-NiNTA nanoparticles (NPs) on tag-displaying amyloid fibrils.
Figures 8A, 8B:
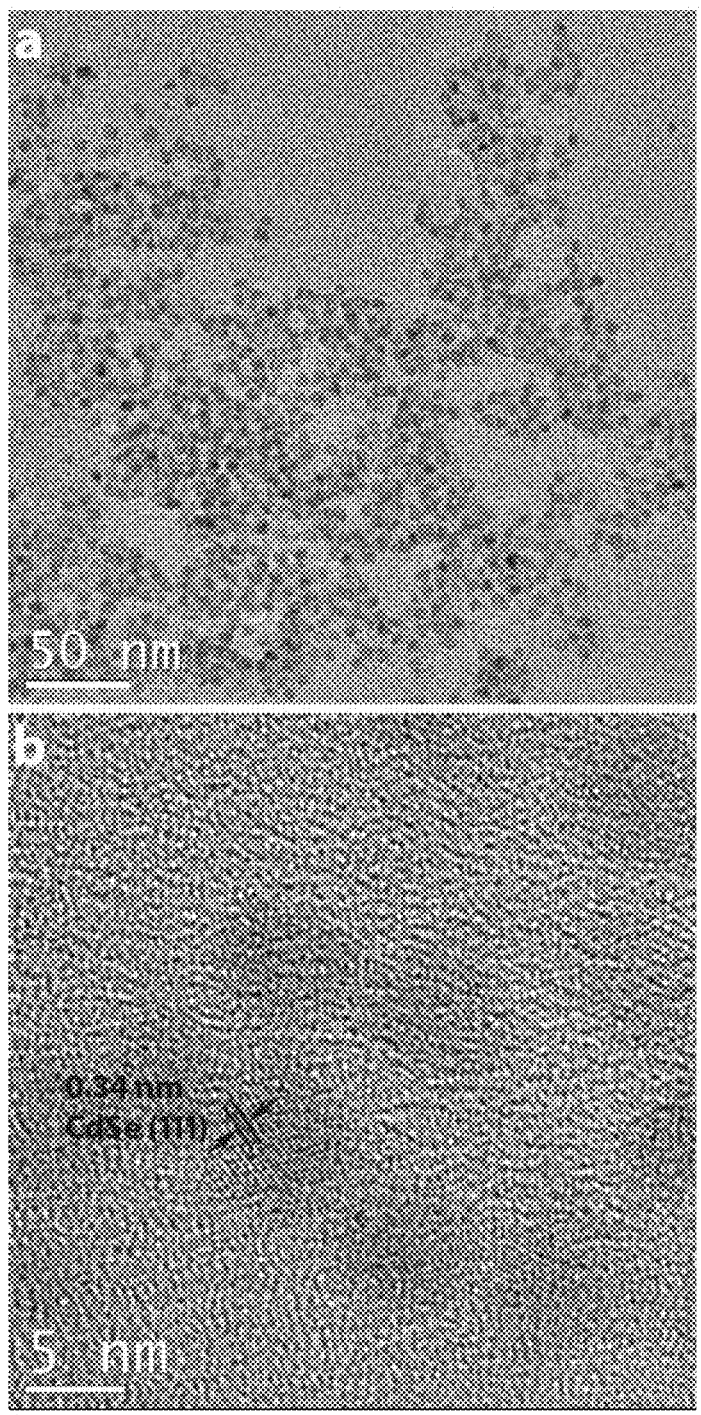
FIGS. 8A and 8B show examples of TEM and HRTEM images of CdSe/CdS QD-pilin-C conjugates.

This Example describes the synthesis of CdSe/CdS core/shell nanorod-SpyCatcher and CdSe/CdS core/shell QD-pillin-C conjugates as well as their self-assembly and co-self-assembly with Au-NiNTA NPs on tag-displaying amyloid fibrils. This example synthesis strategy for QD-SpyCatcher conjugates is generalizable to semiconductor nanocrystals with variable morphologies. In addition to zero-dimensional QDs, 1D CdSe/CdS core/shell nanorods were conjugated with SpyCatcher and self-assembled on SpyTag-displaying amyloid fibrils (FIGS. 7A-7C). The emission profiles of the nanorods had photoluminescence emission peaks at 616 nm with quantum yields of ~44% both before and after conjugation. The lack of change is likely due to the high starting thickness of the CdS shell.[42]

This example synthesis strategy for QD-protein conjugates is also applicable to other peptide-protein binding systems, such as isopeptag-pilin-C. The Cys2-pilin-C protein was expressed from genetically engineered *E. coli* and conjugated it to CdSe/CdS core/shell QDs with a photoluminescence emission peak at 650 nm and quantum yield of 37% (FIGS. 7D-7F, and FIGS. 8A and 8B). The QD-pilin-C conjugates were further self-assembled on isopeptag-displaying amyloid fibrils (FIGS. 7E and 7F). The QD-pilin-C conjugates did not self-assemble on SpyTag-displaying amyloid fibrils (FIG. 7D), thus demonstrating the specificity of the two orthogonal peptide-protein binding systems.

Figures 16A, 16B:
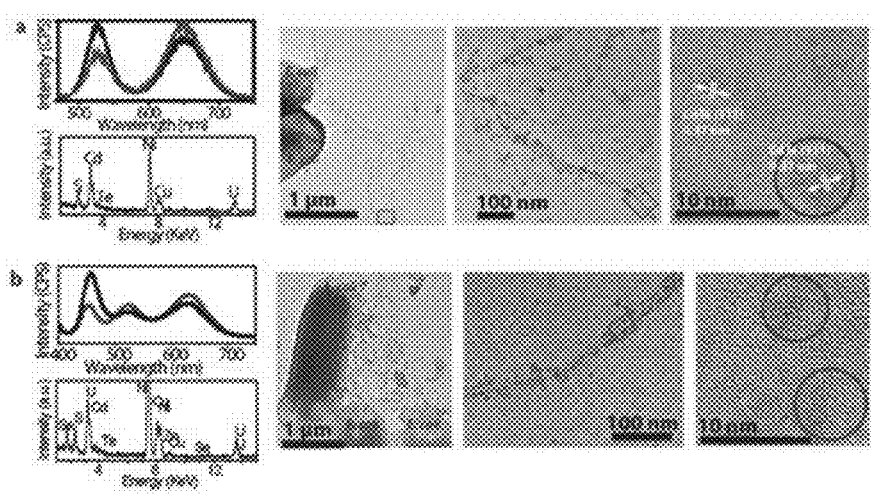
FIG. 16A shows photoluminescence (PL) emission spectra for red CdTe/CdS QD-SpyCatcher and green CdTe/CdS QD-Pilin-C conjugates with CsgAwt amyloid fibers (black curve) or co-organized on CsgASpyTag+CsgAIsopepTagC amyloid fibers (gray curve) fabricated by live cells. EDS spectra, TEM, and HRTEM of the red-emission CdTe/CdS QD-SpyCatcher and green-emission CdTe/CdS QD-Pilin-C conjugates co-assembled on mixed CsgASpyTag and CsgAIsopepTagC amyloid fibrils with live cells.
FIG. 16B shows PL emission spectra for red CdTe/CdS QD-SpyCatcher, green CdTe/CdS QD-Pilin-C, and blue ZnCdSe/ZnS QD-Pilin-N conjugates with CsgAwt amyloid fibers (black curve) or co-assembled on CsgASpyTag+CsgAIsopepTagC+CsgAIsopepTagN amyloid fibers (gray curve) produced by live cells. EDS spectra, TEM, and HRTEM of the red CdTe/CdS QD-SpyCatcher, green CdTe/CdS QD-Pilin-C, and blue ZnCdSe/ZnS QD-Pilin-N conjugates co-organized with mixed CsgASpyTag+CsgAIsopepTagC+CsgAIsopepTagN amyloid fibrils.
Figure 17A:
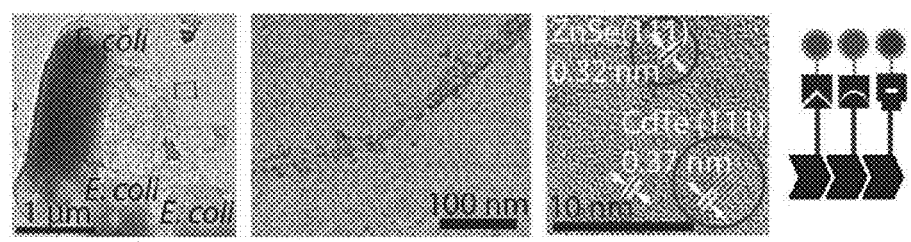
FIG. 17A shows red quantum dot (RQD)-SpyCatcher, green quantum dot (GQD)-Pilin-C, and blue quantum dot (BQD)-Pilin-N conjugates co-organized on mixed CsgASpyTag, CsgAIsopepTagC, and CsgAIsopepTagN amyloid fibrils.

The methods provided herein permit the simultaneous organization of multiple functionalized quantum dots (QDs) at the nanoscale. The methods were used to construct semiconductor-semiconductor heterostructures through specific and covalent SpyTag-SpyCatcher, IsopepTagN-Pilin-N, and IsopepTagC-Pilin-C binding interactions (genes encoding the proteins were appended with N-terminal $(Cys)_2$ and $(His)_7$ tags for SpyCatcher and Pilin-C or C-terminal $(Cys)_2$ and $(His)_7$ tags for Pilin-N). Red-emission CdTe/CdS QD-SpyCatcher conjugates and green-emission CdTe/CdS QD-Pilin-C conjugates were co-organized on composite amyloid fibrils containing $CsgA_{SpyTag}$ and $CsgA_{IsopepTagC}$ secreted by live cells (FIG. 16A). Red-emission CdTe/CdS QD-SpyCatcher, green-emission CdTe/CdS QD-Pilin-C, and blue-emission ZnCdSe/ZnS QD-Pilin-N conjugates were also co-organized on composite amyloid fibrils containing $CsgA_{SpyTag}$, $CsgA_{IsopepTagC}$, and $CsgA_{IsopepTagN}$ (FIG. 17A). As illustrated in FIGS. 16A and 16B, decreases in high-energy emission and concurrent increases in low-energy emission were observed in these heterostructures, which could be potentially attributed to energy transfer from the larger bandgap QDs to the smaller bandgap QDs (K. E. Sapsford, et al. *Biotecnol.* 16, 247-273 (2004)).

Figure 17B:
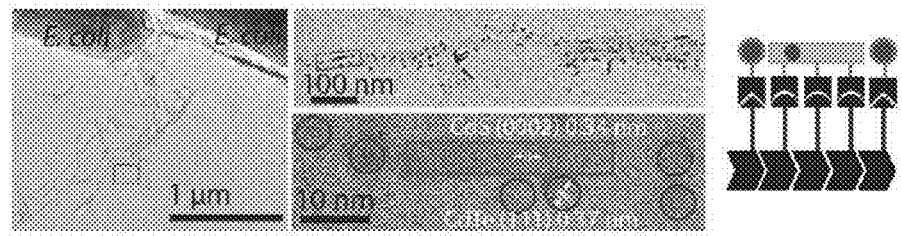
FIG. 17B shows CdSe/CdS heteronanocrystals (HNCs)-Pilin-C conjugates co-assembled with RQD-SpyCatcher conjugates on mixed $CsgA_{IsopepTagC}$ and $CsgA_{SpyTag}$ amyloid fibrils.
Figure 17C:
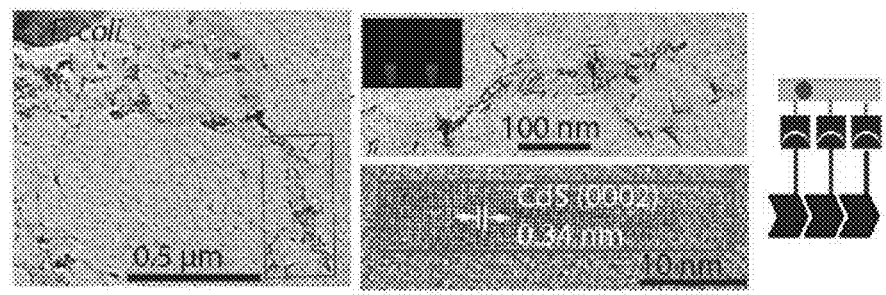
FIG. 17C shows CdSe/CdS HNCs-Pilin-C conjugates assembled on $CsgA_{IsopepTagC}$ amyloid fibrils.
Figure 17D:
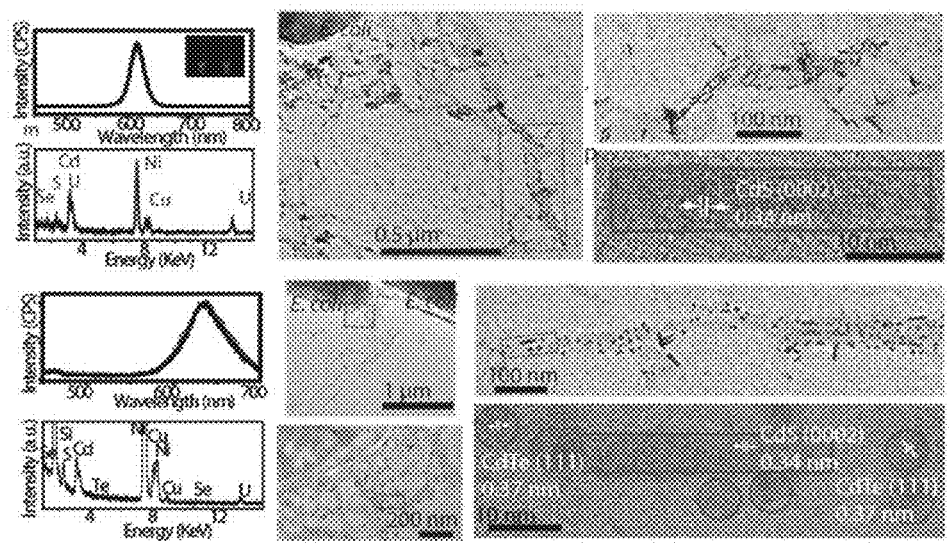
FIG. 17D shows self-organization of CdSe/CdS dot-in-rod HNC and HNC-QD semiconductor-semiconductor heteronanostructures with live cells. Top, PL emission spectra of CdSe/CdS HNC-Pilin-C conjugates before (black) and after (red) conjugation with Pilin-C proteins; the inset picture shows the HNCs before (left) and after (right) conjugation with Pilin-C proteins; EDS spectra, TEM, and HRTEM of CdSe/CdS HNC-Pilin-C conjugates assembled on CsgA$_{IsopepTagC}$ amyloid fibrils with live cells. Bottom, PL emission spectra of CdSe/CdS HNC-Pilin-C and red CdTe/CdS QD-SpyCatcher conjugates with wild-type CsgA (black) or mixed CsgA$_{IsopepTagC}$+CsgA$_{SpyTag}$ amyloid fibrils (red). EDS spectra, TEM, and HRTEM of CdSe/CdS HNC-Pilin-C and red CdTe/CdS QD-SpyCatcher conjugates organized on CsgA$_{IsopepTagC}$+CsgA$_{SpyTag}$ amyloid fibrils with live cells.
Figure 17E:
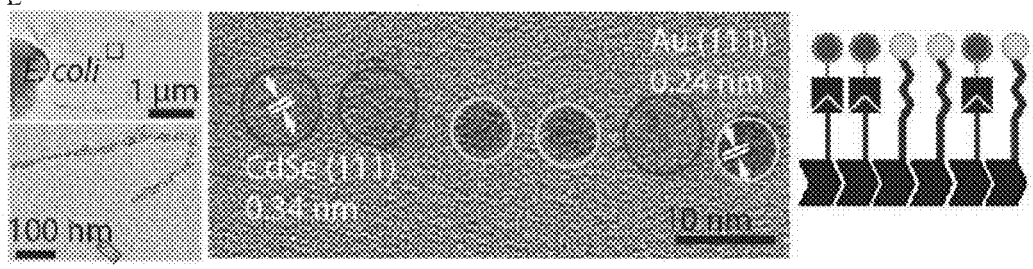
FIG. 17E shows CdSe/CdS QD-SpyCatcher conjugates and Au-NiNTA NPs co-patterned on mixed CsgA$_{SpyTag}$ and CsgA$_{HisTag}$ amyloid fibrils.

The present methods for synthesizing QD-protein conjugates are generalizable to semiconductor nanomaterials with variable geometries. In addition to zero-dimensional (0D) QDs, one-dimensional (1D) trioctylphosphine oxide/trioctylphosphine (TOPO/TOP)-capped CdSe/CdS dot-in-rod heteronanocrystals (HNCs) were conjugated with Cys2-Pilin-C and organize on IsopepTagC-displaying amyloid fibrils with live cells (FIGS. 17B-17D). The emission profiles of the HNCs had photoluminescence (PL) emission peaks at 630 nm with quantum yields of ~46% both before and after conjugation (FIG. 17D). The lack of change is likely due to the high starting thickness of the CdS shell (A. M. Smith, et al. *Chem. Res.* 43, 190-200 (2010)). HNC-Pilin-C conjugates and red-emission CdTe/CdS QD-SpyCatcher conjugates were co-organized on composite amyloid fibrils consisting of CsgASpyTag and CsgAIsopepTagC secreted by live cells to construct semiconductor-semiconductor 0D-1D heterostructures (FIGS. 17E and 17B).

Figures 11, 11A, 11B:
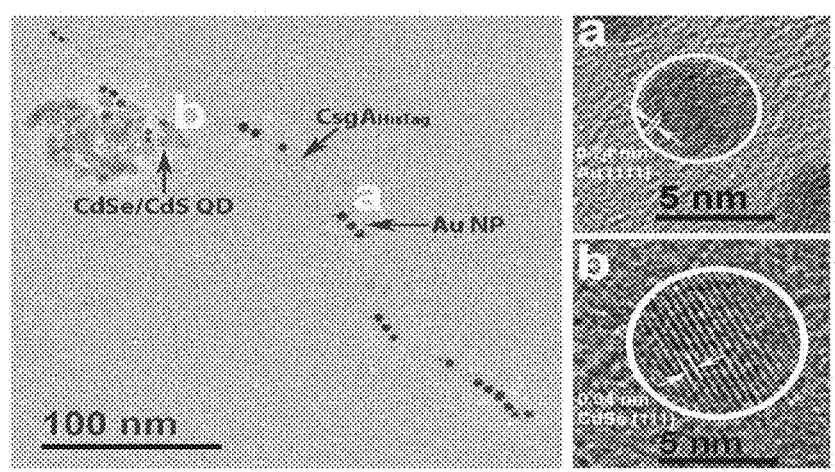
FIG. 11 shows examples of TEM and HRTEM images of CdSe/CdS QD-pilin-C conjugates and Au-NiNTA NPs co-self-assembled onto amyloid fibrils composed of only $CsgA_{HisTag}$ subunits.
FIGS. 11A and 11B show HRTEM images corresponding to the designated areas in the TEM image to the left.
Figures 12A, 12B, 12C:
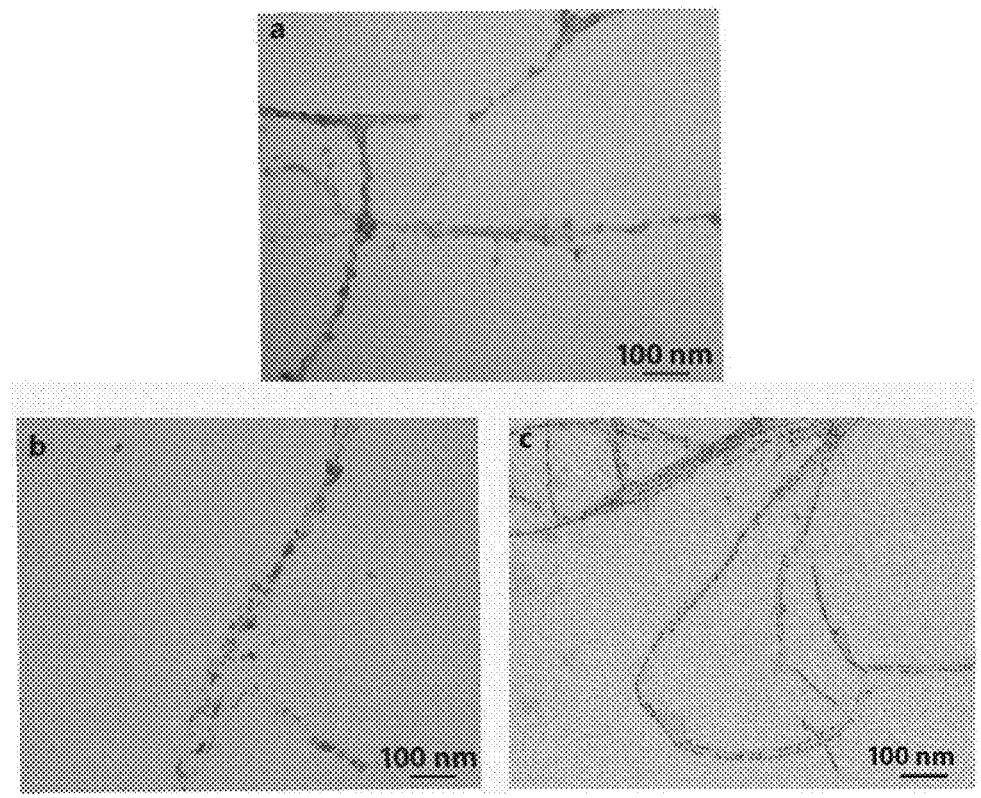
FIGS. 12A-12C show examples of TEM images showing that the histidine tags used to purify $Cys_2$-SpyCatcher are not accessible to Au-NiNTA nanoparticles after $Cys_2$-SpyCatcher is conjugated with QDs to form QD-SpyCatcher.
Figure 13:
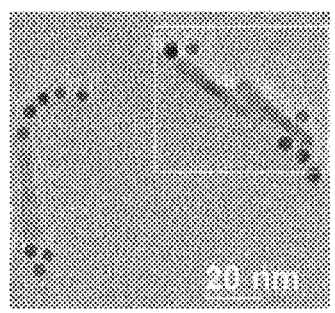
FIG. 13 shows an enlarged TEM image of FIG. 7K, which shows CdSe/CdS nanorod SpyCatcher conjugates and Au-NiNTA NPs co-self-assembled onto amyloid fibrils composed of mixed $CsgA_{SpyTag}$ and $CsgA_{HisTag}$ subunits.
Figures 15A, 15B, 15C, 15D, 15E, 15F, 15G, 15H:
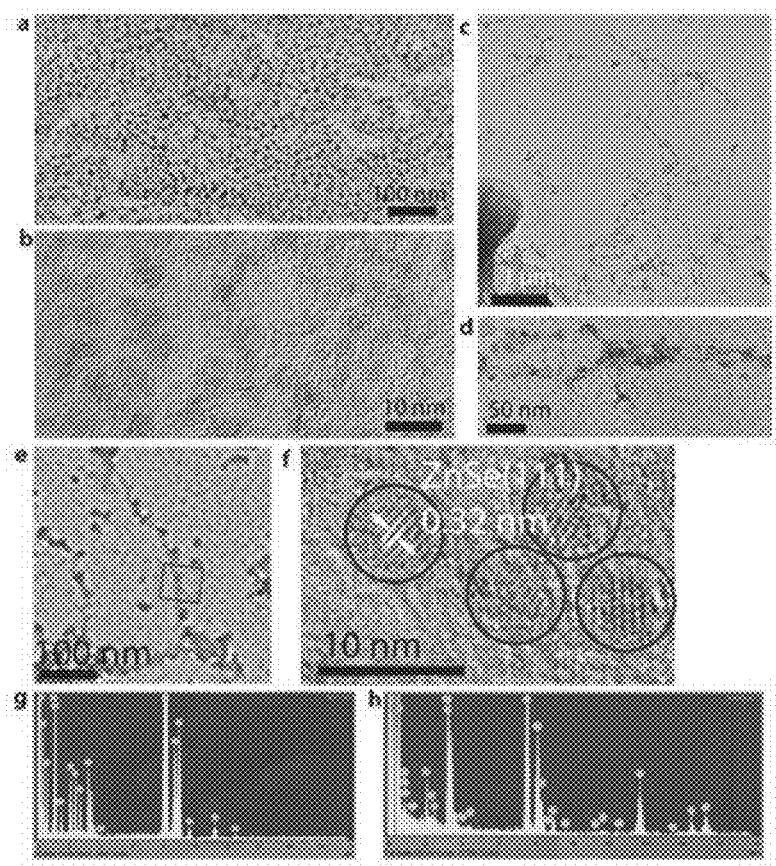
FIGS. 15A-15H show transmission electron microscopy (TEM) images (FIGS. 15A and 15B) and energy-dispersive X-ray spectroscopy (EDS) spectra (FIG. 15G) of the starting ZnCdSe quantum dots (QDs) and the resulting ZnCdSe/ZnS QD-Pilin-N conjugates organized with CsgAIsopepTagN displaying amyloid fibrils with live cells (FIGS. 15C-15F).

Genetically encoded amyloid fibrils displaying multiple peptide tags were also used assemble semiconductor-metal nanoheterostructures.[43,44] As shown in FIGS. 7G and 7H, FIGS. 9A and 9B, and FIGS. 10A and 10B, CdSe/CdS QD-pilin-C conjugates and gold-nickel-nitrilotriacetic-acid nanoparticles (Au-NiNTA NPs) were combined with amyloid fibrils composed of $CsgA_{isopeptag}$ and $CsgA_{HisTag}$. The HisTag mediates specific interactions with NiNTA.[44] Combining the two types of NPs with amyloid fibrils displaying isopeptag and HisTag resulted in the co-assembly of CdSe/CdS core/shell QDs and Au-NiNTA NPs along the amyloid fibrils. EDS spectra of the sample revealed the presence of Cd and Se from the QD CdSe core, S from the QD shell, Au from the Au-NiNTA NPs, and U from the stained amyloids (FIG. 7I), suggesting successful construction of 1D nanoheterostructures. The CdSe/CdS QD-pilin-C conjugates could not attach to CsgAHisTag amyloid fibrils, which do not display isopeptag (FIGS. 11, 11A and 11B). Furthermore, the histidine residues used to purify the SpyCatcher protein after synthesis by bacteria were not accessible to Au-NiNTA NPs during the self-organization of nanoparticles on amyloids (FIGS. 12A-12C).[25] These results demonstrate the orthogonality of the tags used.

In addition, SpyCatcher-conjugated CdSe/CdS core/shell nanorods and Au-NiNTA NPs were combined with amyloid fibrils displaying both SpyTag and HisTag; this resulted in the co-assembly of CdSe/CdS core/shell nanorods and Au-NiNTA NPs along the amyloid fibrils (FIGS. 7J-7K). The formation of the semiconductor-metal nanoheterostructures was verified using HRTEM (FIG. 13 and FIGS. 14, 14A and 14B) and EDS (FIG. 7L), indicating that our method is general.

FIGS. 7A and 7B show TEM images of 616 nm emission (FIG. 7A) unconjugated CdSe/CdS core/shell nanorods and (FIG. 7B) SpyCatcher-conjugated CdSe/CdS core/shell nanorods self-assembled on SpyTag-displaying amyloid fibrils. In FIG. 7C, the images show the CdSe/CdS nanorods before (left) and after (right) conjugation with SpyCatcher. The spectra are for the corresponding CdSe/CdS nanorods before (top curve) and after (bottom curve) conjugation with SpyCatcher. FIG. 7D shows a TEM image of CdSe/CdS QD-pilin-C conjugates with SpyTag-displaying amyloid fibrils. FIGS. 7E and 7F show TEM images of CdSe/CdS QD-pilin-C conjugates self-assembled on isopeptag-displaying fibrils. The image in FIG. 7F is the white rectangle marked area in FIG. 7E. FIGS. 7H and 7H show TEM images of CdSe/CdS QD-pilin-C conjugates co-self-assembled with Au-NiNTA NPs on amyloid fibrils composed of mixed CsgAisopeptag and CsgAHisTag subunits. The image in FIG. 7H is the white rectangle marked area in FIG. 7G. FIG. 7I shows EDS spectra for the samples shown in FIG. 7E (bottom trace) and FIG. 7G (top trace), respectively. FIGS. 7J and 7K show TEM images of CdSe/CdS nanorod-SpyCatcher conjugates co-assembled with Au-NiNTA NPs on fibrils composed of mixed CsgASpyTag and CsgAHisTag subunits. The image in FIG. 7K is the white rectangle marked area in FIG. 7J. FIG. 7L shows an EDS spectra for the samples shown in FIG. 7B (bottom trace) and FIG. 7K (top trace). In this figure, the red arrows label the semiconductor SpyCatcher-conjugated CdSe/CdS core/shell nanorods or the pilin-C-conjugated CdSe/CdS core/shell QDs. The blue arrows label the Au-NiNTA NPs.

Example 4

Multiplexed and scalable organization of nanomaterials enables the creation of fluorescent bacteria-QD "paints." This was demonstrated by first growing three different *Escherichia coli* (*E. coli*) strains in patterns defined by stencil templates. These bacteria produced curli fibrils displaying SpyTag, IsopepTagC, or IsopepTagN, respectively. The resulting cellular communities were then exposed to mixed solutions containing red CdTe/CdS QD-SpyCatcher, green CdTe/CdS QD-Pilin-C, and blue ZnCdSe/ZnS QD-Pilin-N conjugates.

Figure 18:
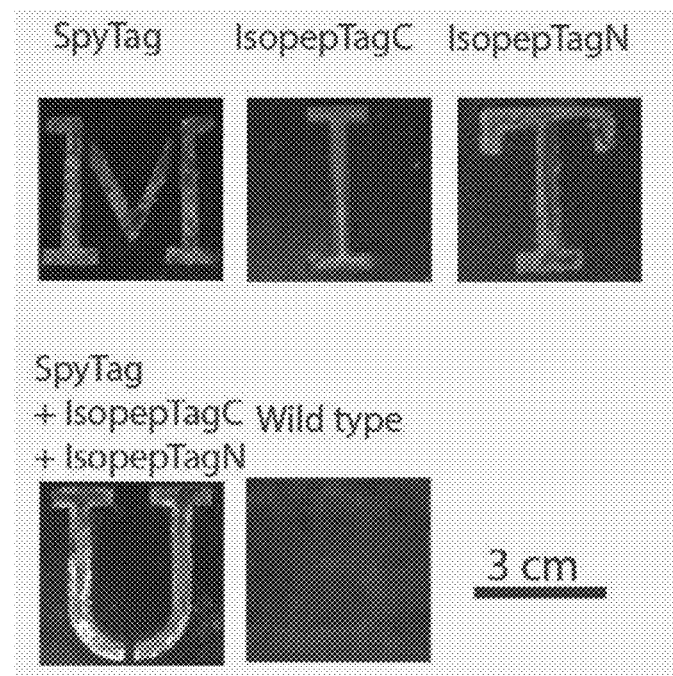
FIG. 18 shows photographs of mixed RQD-SpyCatcher, GQD-Pilin-C, and BQD-Pilin-N conjugates self-assembled with CsgASpyTag (Letter "M"), CsgAIsopepTagC (Letter "I"), CsgAIsopepTagN (Letter "T"), CsgASpyTag+CsgAIsopepTagC+CsgAIsopepTagN (Letter "U"), and CsgAwt (Letter "B") amyloid fibrils expressed by live cells grown with stencil templates.
Figure 19:
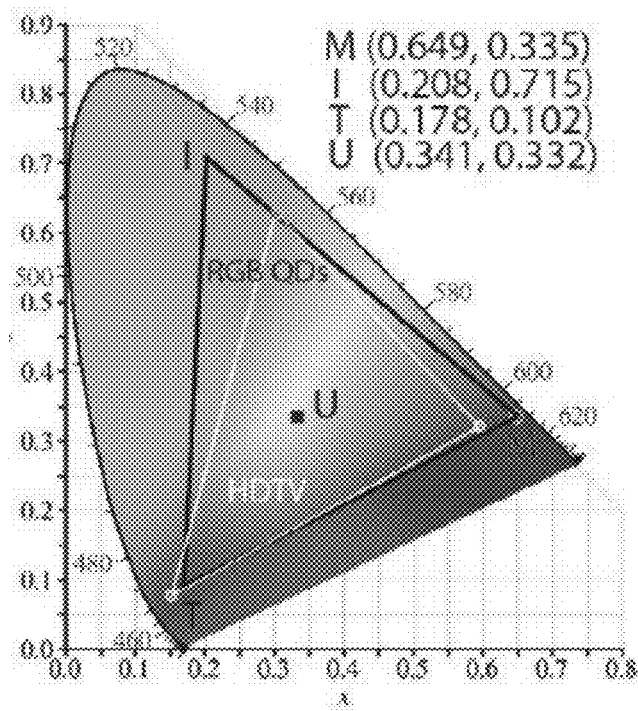
FIG. 19 shows a diagram of the Commission Internationale de l'Eclairage (CIE) 1931 color space that shows the color properties, rendered in grayscale, of the RGB bacterial-QD patterns ("M", "I", "T" & "U", in the black triangle). The HDTV (Rec. 709) color space standard is plotted as a white triangle for comparison.

*Escherichia coli* expressing SpyTag-displaying curli fibrils specifically organized the red QD-SpyCatcher conjugates into a red "M" (FIG. 18, top left panel, rendered in grayscale). *E. coli* expressing IsopepTagC-presenting curli fibrils specifically patterned the green QD-Pilin-C conjugates into a green "I" (FIG. 18, top middle panel, rendered in grayscale). *E. coli* expressing IsopepTagN-displaying curli fibrils specifically organized blue QD-Pilin-N conjugates into a blue "T" (FIG. 18, top right panel, rendered in grayscale). When three different *E. coli* strains expressing SpyTag-, IsopepTagC-, and IsopepTagN-displaying curli fibrils were grown together, the resulting bacterial community captured the red, green, and blue QDs, thus leading to a white "U" (FIG. 18, bottom left panel, rendered in grayscale). Thus, the resulting colors were programmable by the identities and relative compositions of the cellular communities that determine which peptide tags are displayed on the curli amyloid scaffolds. When wild-type *E. coli* was used, little QD fluorescence could be observed (FIG. 18, bottom middle panel). FIG. 19 shows the Commission Internationale de l'Eclairage (CIE) chromaticity coordinates of the red (0.649, 0.335), green (0.208, 0.715), and blue (0.178, 0.102) QD-protein conjugates with the living cell communities in the CIE 1931 chromaticity diagram, rendered in grayscale. A high-definition television (HDTV) standard (Rec. 709) for red (0.64, 0.33), green (0.30, 0.60), blue (0.15, 0.06) is plotted for comparison. The QD-protein conjugates can achieve a larger (130%) gamut than that of the HDTV standard, especially in the green and red region, and can be selectively organized based on the composition of living cell populations.

Example 5

Figures 20A, 20B, 20C, 20D, 20E, 20F, 20G, 20H, 20I, 20J, 20K, 20L:
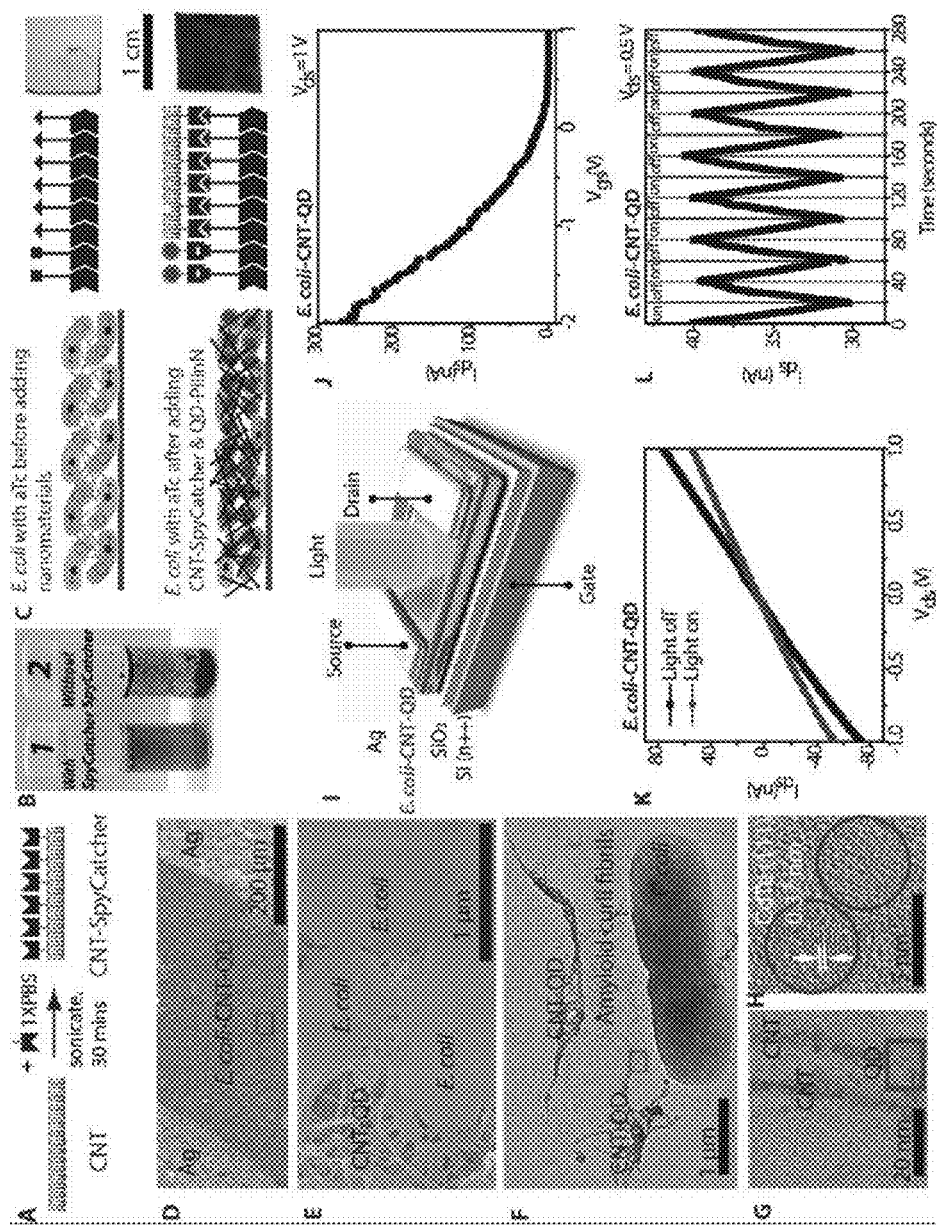
FIGS. 20A-20L show the organization of carbon nanotube (CNT)-SpyCatcher and QD-Pilin-N conjugates with cell-synthesized tag-displaying amyloid fibrils for field-effect transistors (FETs) and photodetector devices.
Figures 21A, 21B, 21C, 21D, 21E, 21F:
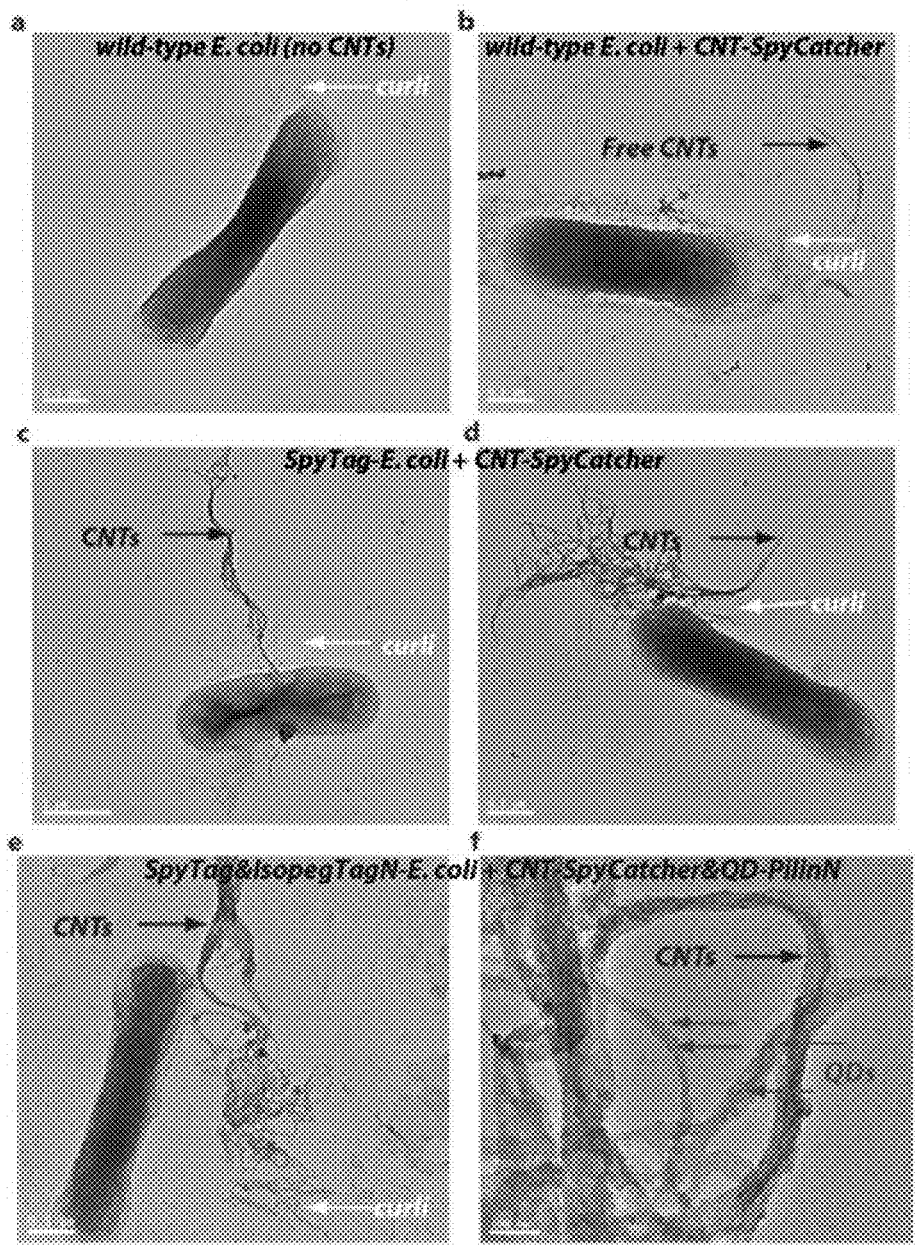
FIGS. 21A-21F show self-organization of CNT-SpyCatcher conjugates with E. coli.
Figures 22A, 22B, 22C, 22D:
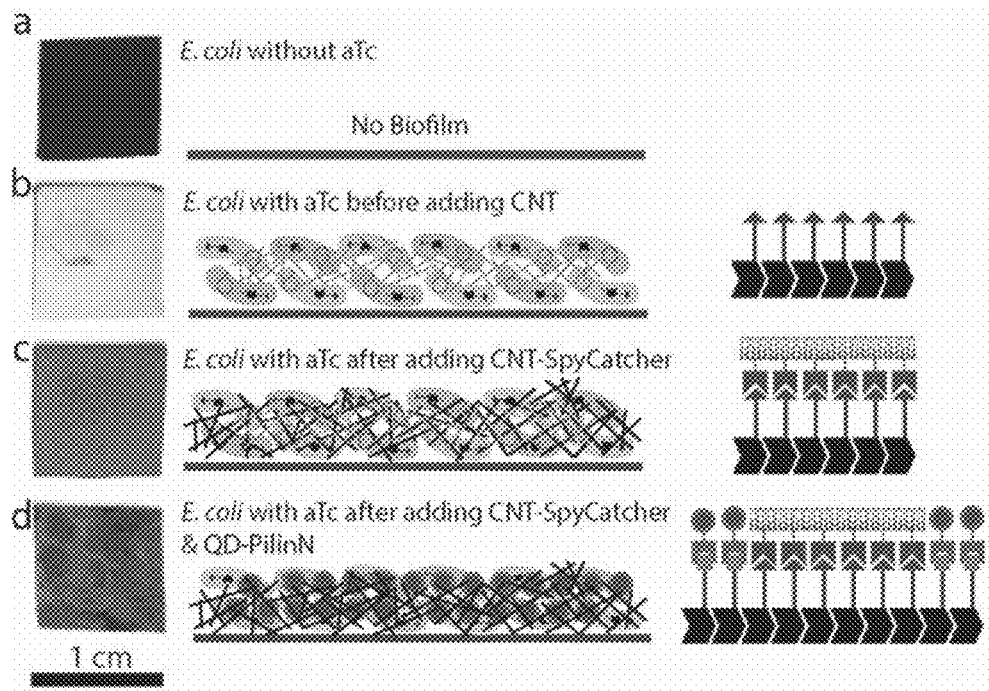
FIGS. 22A-22D show pictures and schematic figures of growth and self-organization of CNT-SpyCatcher and red QD-Pilin-N conjugates on mixed CsgASpyTag and CsgAIsopepTagN displaying amyloid fibrils with live cells in the biofilm on a SiO$_2$ covered silicon wafer.
Figures 23A, 23B:
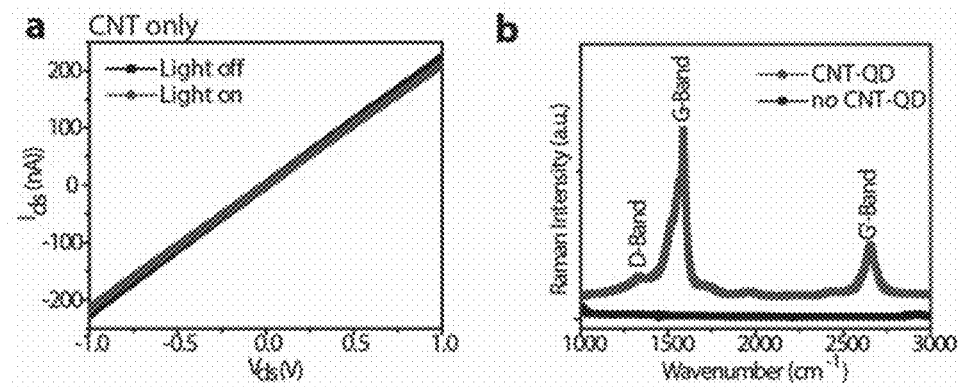
FIG. 23A shows typical drain current (I$_{ds}$) versus drain voltage (V$_{ds}$) at V$_{gs}$=0 V of the bacterially organized CNT device without QDs, along with optical illumination (532 nm light with Plight=20 mW cm−2).
FIG. 23B shows Raman spectra of the E. coli assembled CNT-QDs (gray trace) and E. coli cells without CNT-QDs (black trace, control).

The live cell platform provided herein can be used to assemble functional optoelectronic devices, such as transistors, using carbon nanotubes and QDs. Carbon nanotubes (CNTs) were functionalized with recombinant SpyCatcher proteins via sonication (FIG. 20). The resulting CNT-SpyCatcher conjugates dispersed well in 1×PBS buffer, while the CNTs did not disperse in the absence of protein functionalization (FIG. 20B). The interactions between proteins and CNTs could be mediated by tyrosine and histidine residues in SpyCatcher as well as pi-pi stacking interactions, hydrophobic interactions, and charge-pi interactions (M. Calvaresi, et al. *Acc. Chem. Res.* 46, 2454-2463 (2013)). Next, cell populations were grown with SpyTag- and IsopepTagN-amyloid fibrils on the surface of the highly doped n-type Si substrates (1 cm$^2$) covered with a 100 nm thick SiO$_2$ dielectric layer (FIG. 20C, FIG. 21, FIG. 22). CNT-SpyCatcher conjugates and red QD-Pilin-N conjugates were specifically co-assembled by mixed SpyTag- and Isopep-TagN-displaying amyloid fibrils within the live cell populations (FIGS. 21A-21F). Silver paint was deposited as source and drain electrodes on the cell populations, and gallium-indium eutectic was used as the back-gate electrode to make field-effect transistors (FETs). The SEM images of the channel material in FIG. 20D and FIG. 20E revealed assembled heterostructures containing *E. coli* cells and wire-like structures. TEM, HRTEM and Raman analysis further confirmed that the wire-like structures consisted of co-organized CNTs and QDs with amyloid fibrils (FIGS. 20F-10H, FIG. 23B). For the typical device in FIG. 20I, at a source-drain potential ($V_{ds}$) of 1 V, the assembled device had source-drain currents ($I_{ds}$) that decreased with increases in the gate potential ($V_{gs}$) (FIG. 20J). This suggests that holes, rather than electrons, were the major charge carriers inside the assembled CNT-QD-amyloid heterostructures and that the devices displayed p-type behavior. The hole mobility for these devices was calculated as ~1.1 cm$^2$V$^{-1}$s$^{-1}$ based on the known back-gate area capacitance and the device dimensions (FIG. 20D). Devices with enhanced performance may be achieved by using longer and purer semiconducting carbon nanotubes.

The steady-state photocurrent was measured under constant light illumination by a 532 nm laser while the source-drain voltage was varied between −1 and +1 V. The CNT-QD device displayed a decrease in source-drain current ($I_{ds}$) upon illumination, while the control CNT-only device did not (FIG. 20K, FIG. 23A), suggesting that QDs can endow the device with photosensitivity. The evolution of the source-drain current ($I_{ds}$) over time under intermittent illumination (FIG. 20L) revealed that the current reached a low value under light and recovered to a high value in dark conditions. The stability of the photo-switching behavior was demonstrated by performing repeated intermittent illumination of the device for 280 seconds (FIG. 20L). During illumination, excitons could be generated in the QDs. Electron transfer from QDs to CNTs could occur, resulting in enhanced electron-hole recombination within the CNTs and thus a reduction in the current from source to drain. The remaining holes in the QDs could have an electrostatic influence on the CNTs to reduce current flow (B. H. Juarez, et al. *Nano Lett.* 7, 3564-3568 (2007)). Thus, the present have demonstrated that living cell populations can be used to create functional FET devices with photosensitivity based on CNT-QD heterosystems assembled on multiplexed amyloid scaffolds. This platform is readily scaled-up at low-cost due to the ease of growing large bacterial populations, thus, cell-directed organization of CNT-QDs heterostructures could be used to enable the economical production of functional devices with controlled compositions.

In summary, as demonstrated in the above examples, cell-synthesized amyloid fibrils can be genetically engineered as nanoscaffolds for the large-scale organization of functionalized fluorescent semiconductor nanocrystals and other nanoparticles. Specific SpyTag-SpyCatcher and isopeptag-pilin-C interactions are mediated between isopeptide-bond-forming proteins conjugated to the nanocrystals and cognate binding tags displayed on curli amyloid fibrils. These Cys$_2$-linked isopeptide-bond-forming proteins were expressed by and purified from *E. coli* for the synthesis of highly fluorescent semiconductor nanocrystal-protein conjugates. In contrast to the classic carbodiimide crosslinker chemistry strategy, Cys$_2$-linked proteins were incorporated into the semiconductor nanocrystal surface during shell synthesis, thus providing robust conjugation at one defined attachment point on the protein. These engineered amyloid fibrils and genetically encoded chemistries enable, among other things, the self-assembly of micron-level one-dimensional semiconductor nanocrystal chains and semiconductor-metal nanoheterostructures.

Additional embodiments of the present disclosure may include controlling the synthesis of genetically engineered amyloid fibrils with synthetic gene circuits[45-46] to implement autonomous cell-based biofabrication platforms as well as integrating protein design[47-48] to achieve finer control of nanoscale structures. Aspects of the present disclosure may facilitate the patterning of functional nanomaterials for large-area light harvesting and emitting devices as well as biological applications using low-cost and renewable scaffolds.

Methods

Genetic Engineering of Tag-Displaying Amyloidfibrils.

E. coli bacteria were engineered to synthesize amyloid fibrils displaying heterologous peptides.[43-44] DNA encoding the desired peptides were appended to the 3' end of the gene encoding the major curlin subunit, CsgA, which forms curli amyloid fibrils, and a tightly regulated anhydrotetracycline (aTc)-inducible system[49] was used to express the modified csgA genes.[44] DNA containing the csgA$_{SpyTag}$, csgA$_{isopeptag}$, and csgA$_{HisTag}$ genes (Table 1) with KpnI and MluI sticky ends were generated by PCR and KpnI/MluI digest; these fragments were ligated with the pZA-CmR-rr12-pL(tetO)-vector[44] to create pZA-CmR-rr12-pL(tetO)-csgA$_{SpyTag}$, pZA-CmR-rr12-pL(tetO)-csgA$_{isopeptag}$, and pZA-CmR-rr12-pL(tetO)-csgA$_{HisTag}$ plasmids, respectively (Table 2). These plasmids were transformed into MG1655 PRO ΔcsgA ompR234 cells[44] to create aTc$_{Receiver}$/CsgA$_{SpyTag}$, aTc$_{Receiver}$/CsgA$_{isopeptag}$, and aTc$_{Receiver}$/CsgA$_{HisTag}$ cells, respectively (Table 3). The PRO cassette allows for high-level expression of the TetR protein[50], which is necessary for tight regulation of csgA with aTc via the pL(tetO) promoter. The endogenous csgA gene is knocked out (ΔcsgA) to ensure that all fibrils formed are composed of genetically engineered CsgA subunits. The ompR234 mutation enables fibril production in liquid media.[51]

For cell-based synthesis of amyloid fibrils, cells were inoculated from frozen stocks into LB with chloramphenicol (30 µg/mL) and grown at 37° C. with shaking for 12 hours. The cells were then spun down and the supernatant removed. The cells were re-suspended in 1×PBS buffer. Next, cells were inoculated into 1 mL M63 glucose with aTc (250 ng/mL) and chloramphenicol (30 µg/mL) in 24-well polystyrene plate wells, which had a diameter of 1.56 cm. A round glass coverslip (from Thermanox) with diameter of 1.3 cm was placed at bottom of each well. These cells were grown at 30° C. with no shaking for 16-24 hours. For production of SpyTag-displaying amyloid fibrils, aTc$_{Receiver}$/CsgA$_{SpyTag}$ cells were inoculated at a seeding concentration of 5×10$^7$ cells/mL. For production of isopeptag-displaying amyloid fibrils, aTc$_{Receiver}$/CsgA$_{isopeptag}$ cells were inoculated at a seeding concentration of 5×10$^7$ cells/mL. For production of fibrils displaying both SpyTag and HisTag, aTc$_{Receiver}$/CsgA$_{SpyTag}$ and aTc$_{Receiver}$/CsgA$_{HisTag}$ cells were inoculated at a concentration of 2.5×10$^7$ cells/mL each and co-cultured. For production of fibrils displaying both isopeptag and HisTag, aTc$_{Receiver}$/CsgA$_{isopeptag}$ and aTc$_{Receiver}$/CsgA$_{HisTag}$ cells were inoculated at a concentration of 2.5×10$^7$ cells/mL each and co-cultured (Table 2). The resulting cellular populations were washed, dislodged, and resuspended in 1×PBS buffer to obtain cell-synthesized amyloid fibrils for directing the micron-level assembly of QDs.

Production of Cys$_2$-SpyCatcher and Cys$_2$-Pilin-C Proteins.

To produce Cys$_2$-SpyCatcher protein, codons encoding two cysteine residues were introduced to the gene encoding SpyCatcher, expressed the protein in E. coli, and purified the recombinant protein.[31,51] Specifically, the QuikChange Lightning Kit (Agilent) was used on the pDEST14-T7-SpyCatcher plasmid to add codons encoding two cysteine residues after the start codon of the SpyCatcher gene, creating the pDEST14-T7-Cys$_2$-SpyCatcher expression plasmid (Table 2). This expression plasmid was transformed into E. coli BL21(DE3) pLysS, and BL21(DE3) pLysS/pDEST14-T7-Cys$_2$-SpyCatcher (Table 3) was then grown for 12-16 hours at 37° C. in LB-Miller with 50 µg/ml carbenicillin and 0.4 mM IPTG. To produce Cys$_2$-pilin-C protein, we used the QuikChange Lightning Kit (Agilent) on the pET28a-T7-pilinC plasmid[33] to add codons encoding two cysteine residues after the start codon of the pilin-C gene, creating the pET28a-T7-Cys$_2$-pilin-C expression plasmid (Table 2). This expression plasmid was transformed into E. coli BL21(DE3) pLysS, and BL21(DE3) pLysS/pET28a-T7-Cys$_2$-pilinC (Table 3) was grown for 12-16 hours at 37° C. in LB-Miller with 30 µg/ml kanamycin and 0.4 mM IPTG. These proteins also contain six histidine residues at the N-terminus following the cysteine residues, allowing them to be purified using Ni-NTA Spin Columns (Qiagen) with the native protein purification protocol described in the Ni-NTA Spin Kit Handbook. For further purification of proteins, the eluted Cys$_2$-SpyCatcher and Cys$_2$-pilin-C in elution buffer (NPI-500, 50 mM NaH$_2$PO$_4$, 300 mM NaCl, 500 mM imidazole, pH 8.0) were loaded into 0.5 mL Amicon filters (MWCO 3 KDa), 1×PBS buffer was added to the filters to make the total volumes 500 µL, and the samples were subjected to centrifugation at 11,000 rpm for 10 minutes. The washing (each wash process was performed with 400 µL of 1×PBS buffer) and centrifugation steps were repeated three times. This ultrafiltration process removed imidazole from the protein solutions.

CdSe/CdS Core/Shell QDs Conjugated with Cys$_2$-SpyCatcher or Cys$_2$-Pilin-C.

Published protocols were used for the synthesis of oleic-acid capped CdSe QDs, and then performed ligand exchange to produce water-soluble CdSe QDs.[38] For a typical conjugation experiment, a 20 µL water-soluble CdSe QD solution (OD$_{625}$ of 0.01) was added to 80 µL of DI-water. Then, 10 µL of Cd$^{2+}$ stock solution (25 mM) and 20 µL of MPA stock solution (25 mM) were added, vortexed, and gently sonicated in a 1.5 mL plastic tube. The pH was adjusted to 12.2 with 1M NaOH. Next, 20 µL of purified Cys$_2$-SpyCatcher stock solution (OD$_{280}$ of ~0.5) was added and gently vortexed. The mixture was heated on an Eppendorf thermomixer at 90° C. and 600 rpm for 30 minutes, and then cooled down by submerging it in an ice water bath. To remove free Cys$_2$-SpyCatcher and unreacted precursors from the QD-SpyCatcher conjugation, the reaction mixture was loaded into a 0.5 mL Amicon filter (MWCO 30 KDa) and 1×PBS buffer was added to the filter to make the total volume of the solution equal to 500 µL. The sample was subjected to centrifugation at 7,000 rpm for 7 minutes. The washing (each washing was performed by adding 400 µL of 1×PBS buffer) and centrifugation steps were repeated three times. This ultrafiltration process removed free Cys$_2$-SpyCatcher and unreacted precursors from the CdSe/CdS core/shell QD-SpyCatcher conjugates. For CdSe/CdS core/shell QDs conjugated with Cys$_2$-pilin-C, 20 µL of purified Cys$_2$-pilin-C stock solution (OD$_{280}$ of ~0.5) was added to water-soluble CdSe QD precursor solution and processed as described above. To remove free Cys$_2$-pilin-C and unreacted precursor from the QD-pilin-C conjugation, the reaction mixture was centrifuged at 12,000 rpm for 10 minutes. The unconjugated Cys$_2$-pilin-C and unreacted precursors were removed from the CdSe/CdS core/shell QD-pilin-C conjugates.

CdTe/CdS Core/Shell QDs Conjugated with Cys$_2$-SpyCatcher.

The synthesis of the CdTe/CdS core/shell QDs followed a published protocol.[38] Then, a series of 1 mL of QD precursor solutions were loaded into 1.5 mL plastic tubes, which were placed on an Eppendorf thermomixer at 90° C. and 600 rpm for various reactions times, and then cooled down by submerging the tubes in an ice-water bath. For producing green-emitting CdTe/CdS QDs (with a photoluminescence emission peak at 520 nm), the heating time was 20 minutes. In addition, 30 minutes of heating was performed for yellow CdTe/CdS QDs (with a photoluminescence emission peak at 568 nm), 50 minutes for red CdTe/CdS QDs (with a photoluminescence emission peak at 620 nm), and 70 minutes for NIR CdTe/CdS QDs (with a photoluminescence emission peak at 720 nm). Then, 50 µL of green, yellow, red, or NIR QD solutions was added to 50 µL of DI-water in clean plastic tubes, respectively. Next, 20 µL of purified Cys$_2$-SpyCatcher stock solution (OD$_{280}$ of ~0.5) was also added to each tubes and gently vortexed. The mixture was heated on an Eppendorf thermomixer at 90° C. and 600 rpm for another 30 minutes, and then cooled down by submerging it in an ice-water bath. The solutions were then loaded into 0.5 mL Amicon filters (MWCO 30 KDa), 400 µL 1×PBS buffer was added to the filters, and the samples were subjected to centrifugation at 7,000 rpm for 7 minutes. The washing (each washing was performed with 400 µL 1×PBS buffer) and centrifugation steps were repeated three times. This ultrafiltration process removed free Cys$_2$-SpyCatcher and unreacted precursors from the CdTe/CdS core/shell QDs conjugates, which had photoluminescence emission peaks at 540, 590, 650, 740 nm, respectively. The final samples were highly fluorescent and highly stable in 1×PBS buffer.

ZnCdSe/ZnS Core/Shell QDs Conjugated with Proteins.

The synthesis of core ZnCdSe QDs with blue emission at 440 nm followed a previously reported protocol (A. Kuzyk et al., Nature 483, 311-314 (2012)). Then, 1000 µL of core solutions in a plastic tube were mixed with ZnS precursors (100 µL 25 mM Zn(NO$_3$)$_2$, 100 µL 25 mM MPA), and the pH was tuned to 12.2 using 1 M NaOH. Then, 400 µL of purified Pilin-N-Cys$_2$ stock solution (OD$_{280}$ of ~0.5) was added to each tubes and gently vortexed. The mixture was heated in an Eppendorf thermomixer at 90° C. and 600 rpm for another 30 minutes, and then cooled down by submerging it in an ice-water bath. The solutions were then loaded into 0.5 mL Amicon filters (MWCO 100 KDa), and subjected to centrifugation at 7,000 rpm for 7 minutes. The washing (each was performed with 400 µL 1×PBS buffer) and centrifugation steps were repeated three times. This ultrafiltration process removed free Pilin-N-Cys$_2$ and unreacted precursors from the ZnCdSe/ZnS core/shell QDs-Pilin-N-Cys$_2$ conjugates. The final samples were highly fluorescent and stable in 1×PBS buffer.

CdSe/CdS Core/Shell Nanorods Conjugated with Cys$_2$-SpyCatcher.

First, a published protocol was used ligand exchange.[21] Trioctylphosphine oxide/trioctylphosphine (TOPO/TOP)-capped CdSe/CdS nanorods with emission at 616 nm were centrifuged at 15,000 rpm for 10 minutes and re-dissolved in hexane (200 µL) to make a solution with OD$_{590}$ of 0.002. Formamide (100 µL) mixed with 5 µL of 25 mM MPA solution was added. The mixture was vortexed and sonicated for 15 minutes to allow for ligand exchange in which MPA displaces TOPO/TOP on the nanorod surface to form Cd—S bonds (rather than Cd—P or Cd—O bonds). After ligand exchange, the MPA-capped nanorods were soluble in the polar solvent, thus enabling transfer from the non-polar hexane phase into the polar formamide phase. After settling, the upper hexane layer was removed, and the formamide layer was mixed with 1:1 IPA and centrifuged at 15,000 rpm for 10 minutes. The purified nanorods were re-dissolved in DI water. Then, for conjugation with SpyCatcher, 20 µL solution containing water-soluble nanorods (with absorption of 0.002 at OD$_{590}$ nm) was added to 80 µL of DI-water. Next, 10 µL of Cd$^{2+}$ stock solution (25 mM) and 20 µL of MPA stock solution (25 mM) were added, vortexed, and gently sonicated in a 1.5 mL plastic tube. The pH was tuned to 12.2 by adding NaOH (1M). Then, 20 µL of purified Cys$_2$-SpyCatcher stock solution (OD$_{280}$ of 0.5) was also added and gently vortexed. The mixture was heated on a heating block at 90° C. for 30 minutes, and then cooled down by submerging the tube in an ice-water bath. For removing free Cys$_2$-SpyCatcher and unreacted precursors from the nanorod-SpyCatcher conjugation, reaction mixtures were purified with 0.5 mL Amicon filters (MWCO 30 KDa), as described for CdSe/CdS QD-SpyCatcher QDs.

CdSe/CdS Dot-in-Rod Heteronanocrystals (HNCs) Conjugated with Proteins.

A protocol published previously for ligand exchange was used (Y. G. Zhang, et al. Nat. Nanotechol. 8, 865-872 (2013)). Trioctylphosphine oxide/trioctylphosphine (TOPO/TOP)-capped CdSe/CdS HNCs with emission at 616 nm were centrifuged at 15,000 rpm for 10 minutes and re-dissolved in hexane (200 µL) to make a solution with OD$_{590}$ of 0.002. Formamide (100 µL) mixed with 5 µL of 25 mM MPA solution was added. The mixture was vortexed and sonicated for 15 minutes to allow for ligand exchange in which MPA displaced TOPO/TOP on the HNC surface to form Cd—S bonds (rather than Cd—P or Cd—O bonds). After ligand exchange, the MPA-capped HNCs were soluble in the polar solvent, thus enabling transfer from the non-polar hexane phase into the polar formamide phase. After settling, the upper hexane layer was removed, and the formamide layer was mixed with 1:1 IPA and centrifuged at 15,000 rpm for 10 minutes. The purified HNCs were re-dissolved in DI water. Then, for conjugation with Pilin-C, 20 µL solution containing water-soluble HNCs (with absorption of 0.002 at OD$_{590}$ nm) was added to 80 µL of DI-water. Then, 10 µL of Cd$^{2+}$ stock solution (25 mM) and 20 µL of MPA stock solution (25 mM) were added, vortexed, and gently sonicated in a 1.5 mL plastic tube. The pH was tuned to 12.2 by adding NaOH (1M). Next, 20 µL of purified Cys$_2$-Pilin-C stock solution (OD$_{280}$ of 0.5) was also added and gently vortexed. The mixture was heated in a heating block at 90° C. for 30 minutes, and then cooled down by submerging the tube in an ice-water bath. For removing free Cys$_2$-Pilin-C and unreacted precursors from the HNC-Pilin-C conjugation, reaction mixtures were purified with 0.5 mL Amicon filters (MWCO 100 KDa), as described for CdSe/CdS QD-SpyCatcher QDs.

Self-Assembly of Nanocrystal-Protein Conjugates with Tag-Displaying Amyloidfibrils.

For self-assembly of nanocrystal-SpyCatcher conjugates with SpyTag-displaying amyloid fibrils, approximately 2 µL of conjugates were mixed with 100 µL of tag-displaying amyloid fibrils in 1×PBS in 600 µL plastic tubes, followed by incubation at room temperature for 30 minutes. A similar protocol was followed for the self-assembly of the nanocrystal-pilin-C conjugates with isopeptag-displaying amyloid fibrils. Then, 10 µL of the mixed solution was loaded onto TEM grids (Formvar/Carbon 200 mesh Nickel) for 30 seconds. The grids were subsequently washed twice with 10 µL droplets of 1×PBS buffer and DI H₂O, followed by negative staining with uranyl acetate and dried in air before TEM imaging. For co-self-assembly of the QD conjugates and Au-NiNTA NPs with mixed dual-tag-displaying amyloid fibrils, 1 µL of purified nanocrystal-protein conjugates (CdSe/CdS QD-pilin-C or CdSe/CdS nanorod-SpyCatcher) and 1 µL of 5 nm Au-NiNTA nanoparticles (from Nanoprobes) were added to 100 µL of mixed tag-displaying amyloid fibrils in selective binding buffer (1×PBS with 0.487 M NaCl, 80 mM imidazole, and 0.2 v/v % Tween20) in a 600 µL plastic tube, followed by incubation at room temperature for 30 minutes. The TEM samples were prepared and imaged as before. The selective binding buffer was used to reduce the non-specific binding for Au-NiNTA nanoparticles with amyloid fibrils.

Sample Characterization.

Ultraviolet-Visible (UV-Vis) absorption spectra were recorded at room temperature with a Varian Cary 6000i spectrophotometer. Photoluminescence spectra were measured at room temperature using a NanoLog spectrometer manufactured by HORIBA Jobin Yvon. High-resolution transmission electron microscopy (HRTEM), high angle annular dark field scanning transmission electron microscopy (HAADF-STEM), and energy dispersive X-ray spectroscopy (EDS) were performed on a JEOL JEM 2010F electron microscope operating at 200 kV. For preparation of the TEM samples, 10 µL of the solution samples were placed on TEM grids (from Electron Microscopy Sciences, Catalog Number: FCF200-Ni50) and remained for 30 seconds. The solution was then wiped away with a filter paper, and washed with two drops (10 µL) of 1×PBS buffer. The resulting grids were stained with 2% uranyl acetate solution and air-dried before TEM imaging. A cross-calibrated method was used to measure the photoluminescence quantum yield of the as-synthesized semiconductor nanocrystal-protein conjugates by referencing to Rhodamine 101 (QY=100% in ethanol+0.01 HCl) and Rhodamine 6G (QY=95% in ethanol).[38]

The Raman spectra were recorded with a confocal micro-Raman spectrometer (HORIBA Jobin Yvon LabRam 800). A cross-calibrated method was used to measure the photoluminescence quantum yield of QD-protein conjugates. The standard dyes used in the experiments were Rhodamine 101 (QY=92% in ethanol), Rhodamine 110 (QY=100% in ethanol+0.01 HCl), Coumarin 102 (QY=76.4% in ethanol). Standard 10 mm path length quartz fluorescence cuvettes were used for all measurements. Fluorescence spectra of QD-protein conjugates and dye were taken under identical spectrometer conditions.

The optical density was kept below 0.1 at the excitation wavelength, and the slope of the line generated by plotting the integrated fluorescence intensities against the absorption for multiple concentrations of the QD-protein conjugates and dyes were used to calculate the quantum yields using the expression:

$$\varphi = \varphi'\left(\frac{n}{n'}\right)^2 \times \frac{slope}{slope'}$$

where φ and φ' are the PL QY for the sample and standard, respectively; slope (sample) and slope' (standard) are the slope of the line generated by plotting the integrated fluorescence intensities against the absorption for multiple concentrations of the QD-protein conjugates and dyes at the same wavelength used for PL excitation; n (sample) and n' (standard) are the refractive indices of the solvents used.

Chemicals.

Cadmium nitrate tetrahydrate ($Cd(NO_3)_2 \cdot 4H_2O$, 99.8%), Cadmium oxide (CdO, 99.99+%, powder), Tellurium (Te, powder, −200 mesh, ≥99%, powder), Selenium (Se, powder, <100 mesh, 99.99%), Sulfur (S, 99.998% powder), paraffin liquid ($C_nH_{2n+2}$, n=16-22), oleic acid (OLA, $CH_3(CH_2)_7CH=CH(CH_2)_7COOH$, 90%), Sodium borohydride ($NaBH_4$, powder, ≥99%), 3-Mercaptopropionic acid (MPA, $HSCH_2CH_2CO_2H$, ≥99%), isopropyl alcohol (IPA, 99%), hexane (≥95%), methanol (≥99.5%), Uranyl acetate dehydrate ($UO_2(OCOCH_3)_2 \cdot 2H_2O$, ≥98%), Rhodamine 6G (QY=95% in ethanol), and Rhodamine 101 (QY=100% in ethanol+0.01 HCl), were purchased from Sigma-Aldrich and used without further purification. Ampicillin Sodium Salt (Amp, $C_{16}H_{18}N_3O_4SNa$), Spectinomycin Dihydrochloride (Spec, $C_{14}H_{24}N_2O_7 \cdot 2HCl \cdot 5H_2O$), Kanamycin Sulfate (Kan, $C_{18}H_{36}N_4O_{11} \cdot H_2SO_4$), Chloramphenicol (Cm, $C_{11}H_{12}Cl_2N_2O_5$), and Carbenicillin Disodium Salt (Carb, $C_{17}H_{16}N_2Na_2O_6S$) were purchased from Fisher Scientific and used without further purification.

Large-Scale Synthesis of QD-Protein Conjugates and Tag-Displaying Amyloid Fibrils for Self-Assembly.

For large-scale production of $Cys_2$-SpyCatcher, E. coli strain BL21(DE3) pLysS/pDEST14-T7-$Cys_2$-SpyCatcher from frozen stock was grown overnight in 50 mL LB-Miller with 50 µg/mL carbenicillin. Then, 10 mL of stationary phase cells were added to 1 liter LB-Miller with 50 µg/mL carbenicillin, and further grown to $OD_{600}$ of 0.5-0.7 at 37° C. with shaking for 3-4 hours. Finally, IPTG (0.4 µM) was added and the cultures was grown with shaking for 4 hours at 30° C. The cells were collected by centrifugation and lysed. Proteins were purified with Ni-NTA Resin (Qiagen). 2 mM β-mercaptoethanol was used to break the disulfide bonds. Through buffer exchange with Amicon columns, the resulting $Cys_2$-SpyCatcher proteins were re-dispersed in 1×PBS buffer with $OD_{280}$ of 0.5. For the synthesis of 650 nm emission CdTe/CdS $Cys_2$-SpyCatcher conjugates, 1000 µL unpurified CdTe/CdS QD solution ($OD_{615}$ of 0.02, photoluminescence peak at 630 nm) was mixed with 400 µL of purified $Cys_2$-SpyCatcher stock solution ($OD_{280}$ of ~0.5) and gently vortexed. The mixture was heated on a heating block at 90° C. for 30 minutes, and then cooled down by submerging in an ice-water bath. Unconjugated $Cys_2$-SpyCatcher was then removed with 0.5 mL Amicon filters (MWCO 30 KDa) as described in Methods. The resulting CdTe/CdS QD-SpyCatcher conjugates were resuspended in 1000 µL 1×PBS buffer ($OD_{625}$ of 0.023, photoluminescence peak at 650 nm). The large-scale synthesis of green-emission and NIR-emission CdTe/CdS-SpyCatcher conjugates was performed in a similar fashion.

For large-scale synthesis of tag-displaying amyloid fibrils, E. coli with pZA-CmR-rr12-pL(tetO)-csgA$_{SpyTag}$ or E. coli with pZA-CmR-rr12-pL(tetO)-csgA$_{isopeptag}$ were inoculated from frozen stocks into 50 mL LB with chloramphenicol (30 mg/L) and grown at 37° C. with shaking for 12 hours. The cells were then spun down and re-suspended in 5 mL 1×PBS buffer. The re-suspended cells were inoculated in 5 mL, 40 mL, or 1000 mL M63 glucose media containing aTc (100 µg/L) and chloramphenicol (30 mg/L), with a final cellular concentration of 5×10⁷ cells/mL, in glass dishes with diameters of 6.0 cm (VWR Catalog Number: 89000-300) or 12.5 cm (VWR Catalog Number: 89001-754), or glass flasks with a bottom diameter of 20.5 cm (VWR Catalog Number:

71000-350), respectively. These cells were grown at 30° C. with no shaking for 24 hours.

To achieve self-organization of QD-conjugates on amyloid fibrils synthesized by bacteria in glass dishes (FIG. 5H and FIGS. 4A-4C), M63 media was removed, and the resulting cellular populations attached to the glass walls were gently washed twice with 1×PBS buffer, and then dried in air. For 6.0 cm diameter glass dishes containing E. coli that secreted tag-displaying amyloid fibrils, 0.5 mL of the QD-SpyCatcher conjugates were added along with 4.5 mL 1×PBS buffer. For 12.5 cm diameter glass dishes containing E. coli that secreted tag-displaying amyloid fibrils, 2 mL of the QD-SpyCatcher conjugates were added with 28 mL 1×PBS buffer. Then, the solutions in the glass dishes were incubated at room temperature for 30 minutes. The resulting self-assembled products were obtained by removing the solutions, gently washing twice with 1×PBS buffer, and dried in air.

To obtain powders of amyloid fibrils (FIG. 5I, FIGS. 6A and 6B), M63 media was removed from the glass flasks, and the cellular populations attached to the glass wall were gently washed twice with 1×PBS buffer. Then, these cellular populations were dislodged and re-suspended in 1×PBS buffer. The amyloid fibrils were collected by removing the cells by centrifugation (4000 rpm for 10 minutes) and freeze dried. To verify that the freeze-dried amyloid fibril powders were still able to self-assemble QD-conjugate nanostructures (FIGS. 6C and 6D), 0.5 mg of the dried powder was re-dissolved in 0.5 mL 1×PBS buffer in a 1.5 mL plastic tube, 0.01 mL of the purified 650 nm emission CdTe/CdS QD-SpyCatcher conjugates was then added, and the mixture was incubated at room temperature for 30 minutes. Then, 10 μL of the resulting self-assembled product was placed on TEM grids for 30 seconds. The solution was wiped away with a filter paper, and washed with two drops (10 μL) of 1×PBS buffer. The resulting grids were stained with 2% uranyl acetate solution and air-dried before TEM imaging.

To obtain freeze-dried powders containing the green (540 nm emission) or red (650 nm emission) QD-SpyCatcher conjugates self-assembled on SpyTag-displaying amyloid fibrils (FIG. 5I), 4 mL of the green or red QD-SpyCatcher conjugates were mixed with 30 mL of the cell-free tag-displaying amyloid fibrils in 1×PBS within 50 mL plastic tubes, followed by incubation at room temperature for 30 minutes. The resulting self-assembled products were spun down and freeze-dried to obtain powders. To verify that the self-assembled QD-amyloid nanostructures were retained during the freeze-drying process (FIGS. 5J and 5K), 0.5 mg of the dried powder containing red QD-SpyCatcher with SpyTag-displaying amyloid fibrils was re-dissolved in 0.5 mL 1×PBS buffer in a 1.5 mL plastic tube. Then, 10 μL of the resulting solution was placed on TEM grids for 30 seconds. The solution was wiped away with a filter paper, and washed with two drops (10 μL) of 1×PBS buffer. The resulting grids were stained with 2% uranyl acetate solution and air-dried before TEM imaging.

For the stencil experiments, E. coli expressing $CsgA_{SpyTag}$ (Letter "M"), $CsgA_{IsopepTagC}$ (Letter "I"), $CsgA_{IsopepTagN}$ (Letter "T"), $CsgA_{SpyTag}+CsgA_{IsopepTagC}+CsgA_{IsopepTagN}$ (Letter "U"), and non-tag-displaying CsgA (Letter "B") were grown with the stencil templates (obtained from Michael's, Cambridge Mass.) stuck to the glass dishes. These cells were grown at 30° C. with no shaking for 24 hours. Then, M63 media was removed from the glass dishes, and the cellular populations were gently washed twice with 1×PBS buffer. Then, the cellular populations were exposed to mixed 0.5 mL red CdTe/CdS QD-SpyCatcher, 0.5 mL green CdTe/CdS QD-Pilin-C, 0.5 mL blue ZnCdSe/ZnS QD-Pilin-N with 4.5 mL 1×PBS buffer. After incubating at room temperature for 30 minutes, the resulting products were gently washed twice with 1×PBS buffer, and dried in air. The PL spectra of the bacterial-QD "paints" were measured via spectrometry (NanoLog spectrometer by HORIBA Jobin Yvon). The color coordinates for the spectra in the CIE 1931 color space were generated by a Matlab script.

Carbon Nanotube (CNT)-Protein Conjugates and Self-Assembly of Bacteria-CNT-QD Based Transistors.

For the synthesis of $CNT-Cys_2$-SpyCatcher conjugates, 10 mg of CNTs was added to 600 μL 1×PBS and then mixed with 400 μL of purified $Cys_2$-SpyCatcher stock solution ($OD_{280}$ of ~0.5) and vortexed. The mixture was sonicated for 30 minutes. Free $Cys_2$-SpyCatcher was then removed by centrifugation at 8000 rpm for 10 minutes. The resulting CNT-SpyCatcher conjugates were resuspended in 1000 μL 1×PBS buffer. Then, cells displaying SpyTag and IsopepTagN co-display amyloid fibrils were inoculated at a seeding concentration of $5\times10^7$ cells/mL into 1 mL M63 glucose with aTc (100-250 ng/mL) and chloramphenicol (30 μg/mL) in 24-well polystyrene plate wells with 1 cm² phosphorous-doped n-type silicon wafer (with 100 nm $SiO_2$ insulating layer). The cells were grown at 30° C. without shaking for 16-24 hours. Then, the cells were incubated in 1 mL 1×PBS solution containing purified CNT-SpyCatcher and red CdTe/CdS QD-Pilin-N conjugates in 24-well plates at room temperature for 30 minutes. The silicon wafers were then rinsed with 1×PBS buffer and dried in air. Control samples included cells grown without aTc (FIG. 22A), grown with aTc but without adding CNT and QDs (FIG. 22B), or grown with aTc but without adding the QDs (FIG. 22C). To make the transistors, two silver pastes (Leitsiber 200 from Ted Pella) were applied on cell populations as the source and drain electrodes, while gallium-indium eutectic (Sigma-Aldrich) was placed on the back of the silicon wafer as the gate electrode. Multiple devices (Y. G. Zheng, et al. *Adv. Mater.* 19, 1475-1479 (2007)) were fabricated and measured to confirm reproducible results. The electrical measurements were conducted with a Keithley 4200-SCS Semiconductor Characterization System. The hole mobility for the device were calculated based on the following equation (Z. Deng et al., *ACS Nano* 6, 6197-6207 (2012)):

$$\mu = L/(W \times C_{ox} \times V_{ds}) \times dI_{ds}/dV_{gs} \qquad (Eq.\ 1)$$

For the specific device shown in FIG. 4D, the channel length L was 500 μm, the channel width W was 2000 μm, the capacitance, $C_{ox}$ was $\varepsilon_o\varepsilon_r/d$ ($\varepsilon_0=8.854\times10^{-12}$ $Fm^{-1}$, $\varepsilon_r$ for $SiO_2$=3.9, d=the thickness of $SiO_2$~100 nm), $V_{ds}$ was 1 V, and $dI_{ds}/dV_{gs}$ obtained from the slope of the plot of $I_{ds}$ vs. $V_{gs}$ was −148 nA/V (FIG. 23A). The calculated hole mobility μ of this device was ca. 1.1 $cm^2V^{-1}s^{-1}$.

TABLE 1

Synthetic genes

| Part Name | Part Type | Sequence |
|---|---|---|
| csgA | Gene for the wild-type CsgA amyloid material subunit | ATGAAACTTTTAAAAGTAGCAGCAATTGCAGCA<br>ATCGTATTCTCCGGTAGCGCTCTGGCAGGTGTTG<br>TTCCTCAGTACGGCGGCGGCGGTAACCACGGTG<br>GTGGCGGTAATAATAGCGGCCCAAATTCTGAGC<br>TGAACATTTACCAGTACGGTGGCGGTAACTCTG<br>CACTTGCTCTGCAAACTGATGCCCGTAACTCTGA<br>CTTGACTATTACCCAGCATGGCGGCGGTAATGG<br>TGCAGATGTTGGTCAGGGCTCAGATGACAGCTC<br>AATCGATCTGACCCAACGTGGCTTCGGTAACAG<br>CGCTACTCTTGATCAGTGGAACGGCAAAAATTC<br>TGAAATGACGGTTAAACAGTTCGGTGGTGGCAA<br>CGGTGCTGCAGTTGACCAGACTGCATCTAACTCC<br>TCCGTCAACGTGACTCAGGTTGGCTTTGGTAACA<br>ACGCGACCGCTCATCAGTACTAA<br>(SEQ ID NO: 1)<br>Chapman, M. R. et al. Science 295, 851-855 (2002). |
| csgA$_{HisTag}$ | Gene for the CsgA amyloid aterial subunit with appended HisTag | ATGAAACTTTTAAAAGTAGCAGCAATTGCAGCA<br>ATCGTATTCTCCGGTAGCGCTCTGGCAGGTGTTG<br>TTCCTCAGTACGGCGGCGGCGGTAACCACGGTG<br>GTGGCGGTAATAATAGCGGCCCAAATCACCATC<br>ACCATCACCACCATTCTGAGCTGAACATTTACCA<br>GTACGGTGGCGGTAACTCTGCACTTGCTCTGCAA<br>ACTGATGCCCGTAACTCTGACTTGACTATTACCC<br>AGCATGGCGGCGGTAATGGTGCAGATGTTGGTC<br>AGGGCTCAGATGACAGCTCAATCGATCTGACCC<br>AACGTGGCTTCGGTAACAGCGCTACTCTTGATCA<br>GTGGAACGGCAAAAATTCTGAAATGACGGTTAA<br>ACAGTTCGGTGGTGGCAACGGTGCTGCAGTTGA<br>CCAGACTGCATCTAACTCCTCCGTCAACGTGACT<br>CAGGTTGGCTTTGGTAACAACGCGACCGCTCAT<br>CAGTACCACCATCACCATCACCACCATTAA<br>(SEQ ID NO: 2) |
| csgA$_{SpyTa}$ | Gene for the CsgA amyloid material subunit with appended SpyTag | ATGAAACTTTTAAAAGTAGCAGCAATTGCAGCA<br>ATCGTATTCTCCGGTAGCGCTCTGGCAGGTGTTG<br>TTCCTCAGTACGGCGGCGGCGGTAACCACGGTG<br>GTGGCGGTAATAATAGCGGCCCAAATTCTGAGC<br>TGAACATTTACCAGTACGGTGGCGGTAACTCTG<br>CACTTGCTCTGCAAACTGATGCCCGTAACTCTGA<br>CTTGACTATTACCCAGCATGGCGGCGGTAATGG<br>TGCAGATGTTGGTCAGGGCTCAGATGACAGCTC<br>AATCGATCTGACCCAACGTGGCTTCGGTAACAG<br>CGCTACTCTTGATCAGTGGAACGGCAAAAATTC<br>TGAAATGACGGTTAAACAGTTCGGTGGTGGCAA<br>CGGTGCTGCAGTTGACCAGACTGCATCTAACTCC<br>TCCGTCAACGTGACTCAGGTTGGCTTTGGTAACA<br>ACGCGACCGCTCATCAGTACGGCGGGGGCTCCG<br>GCGGGGGCTCCGCGCACATCGTTATGGTCGATG<br>CATATAAACCCACCAAATAA (SEQ ID NO: 3) |
| csgA$_{isopeptag}$ | Gene for the CsgA amyloid material subunit with appended isopeptag | ATGAAACTTTTAAAAGTAGCAGCAATTGCAGCA<br>ATCGTATTCTCCGGTAGCGCTCTGGCAGGTGTTG<br>TTCCTCAGTACGGCGGCGGCGGTAACCACGGTG<br>GTGGCGGTAATAATAGCGGCCCAAATTCTGAGC<br>TGAACATTTACCAGTACGGTGGCGGTAACTCTG<br>CACTTGCTCTGCAAACTGATGCCCGTAACTCTGA<br>CTTGACTATTACCCAGCATGGCGGCGGTAATGG<br>TGCAGATGTTGGTCAGGGCTCAGATGACAGCTC<br>AATCGATCTGACCCAACGTGGCTTCGGTAACAG<br>CGCTACTCTTGATCAGTGGAACGGCAAAAATTC<br>TGAAATGACGGTTAAACAGTTCGGTGGTGGCAA<br>CGGTGCTGCAGTTGACCAGACTGCATCTAACTCC<br>TCCGTCAACGTGACTCAGGTTGGCTTTGGTAACA<br>ACGCGACCGCTCATCAGTACGAGGTGGAAGTG<br>GCGGCGGAAGTACCGACAAAGATATGACTATCA<br>CCTTCACGAATAAAAAAGACGCGGAATAA (SEQ ID NO: 4) |
| Cys$_2$-SpyCatcher | Gene for the Cys$_2$-SpyCatcher protein | ATGTGTTGTTCGTACTACCATCACCATCACCATC<br>ACGATTACGACATCCCAACGACCGAAAACCTGT<br>ATTTTCAGGGCGCCATGGTTGATACCTTATCAGG<br>TTTATCAAGTGAGCAAGGTCAGTCCGGTGATAT<br>GACAATTGAAGAAGATAGTGCTACCCATATTAA<br>ATTCTCAAAACGTGATGAGGACGGCAAAGAGTT<br>AGCTGGTGCAACTATGGAGTTGCGTGATTCATCT |

TABLE 1-continued

Synthetic genes

| Part Name | Part Type | Sequence |
|---|---|---|
| | | GGTAAAACTATTAGTACATGGATTTCAGATGGA<br>CAAGTGAAAGATTTCTACCTGTATCCAGGAAAA<br>TATACATTTGTCGAAACCGCAGCACCAGACGGT<br>TATGAGGTAGCAACTGCTATTACCTTTACAGTTA<br>ATGAGCAAGGTCAGGTTACTGTAAATGGCAAAG<br>CAACTAAAGGTGACGCTCATATTTAA (SEQ ID<br>NO: 5) |
| Cys2-pilin-C | Gene for the Cys$_2$-pilin-c protein | ATGTGTTGTGGCAGCAGCCATCATCATCATCATC<br>ACAGCAGCGGCCTGGTGCCGCGCGGCAGCCATA<br>TGGCTACAACAGTTCACGGGGAGACTGTTGTAA<br>ACGGAGCCAAACTAACAGTTACAAAAAACCTTG<br>ATTTAGTTAATAGCAATGCATTAATTCCAAATAC<br>AGATTTTACATTTAAAATCGAACCTGATACTACT<br>GTCAACGAAGACGGAAATAAGTTTAAAGGTGTA<br>GCTTTGAACACACCGATGACTAAAGTCACTTAC<br>ACCAATTCAGATAAAGGTGGATCAAATACGAAA<br>ACTGCAGAATTTGATTTTTCAGAAGTTACTTTTG<br>AAAAACCAGGTGTTTATTATTACAAAGTAACTG<br>AGGAGAAGATAGATAAAGTTCCTGGTGTTTCTT<br>ATGATACAACATCTTACACTGTTCAAGTTCATGT<br>CTTGTGGAATGAAGAGCAACAAAAACCAGTAGC<br>TACTTATATTGTTGGTTATAAAGAAGGTAGTAAG<br>GTGCCAATTCAGTTCAAAAATAGCTTAGATTCTA<br>CTACATTAACGGTGAAGAAAAAAGTTTCAGGTA<br>CCGGTGGAGATCGCTCTAAAGATTTTAATTTTGG<br>TCTGACTTTAAAAGCAAATCAGTATTATAAGGC<br>GTCAGAAAAAGTCATGATTGAGAAGACAACTAA<br>AGGTGGTCAAGCTCCTGTTCAAACAGAGGCTAG<br>TATAGATCAACTCTATCATTTTACCTTGAAAGAT<br>GGTGAATCAATCAAAGTCACAAATCTTCCAGTA<br>GGTGTGGATTATGTTGTCACTGAAGACGATTAC<br>AAATCAGAAAAATATACAACCAACGTGGAAGTT<br>AGTCCTCAAGATGGAGCTGTAAAAAATATCGCA<br>GGTAATTCAACTGAACAAGAGACATCTACTGAT<br>AAAGATATGACCATTTAG (SEQ ID NO: 6) |
| isopeptag | Protein | TDKDMTITFTNKKDAE (SEQ ID NO: 7) |
| SpyTag | Protein | AHIVMVDAYKPTK (SEQ ID NO: 8) |

TABLE 2

Plasmids

| Plasmid Name | Plasmid ID | Description |
|---|---|---|
| pZA-CmR-rr12-pL(tetO)-csgAHisTag | PAYC003 | p15A origin, Cm resistance, rr12 riboregulator, pL(tetO) promoter, csgA$_{HisTag}$ output gene |
| pDEST14-T7-Cys$_2$-SpyCatcher | PAYC016 | pBR322 origin, Amp resistance, T7 promoter, Cys$_2$-SpyCatcher output gene |
| pET28a-T7-Cys$_2$-pilin-C | PAYC018 | pBR322 origin, Kan resistance, T7 promoter, Cys2-pilin-C output gene |
| pZA-CmR-rr12-pL(tetO)-csgA$_{SpyTag}$ | PAYC019 | p15A origin, Cm resistance, rr12 riboregulator, pL(tetO) promoter, csgA$_{SpyTag}$ output gene |
| pZA-CmR-rr12-pL(tetO)-csgA$_{isopeptag}$ | PAYC020 | p15A origin, Cm resistance, rr12 riboregulator, pL(tetO) promoter, csgA$_{isopeptag}$ output gene |

TABLE 3

Cell strains

| Strain Name | Strain ID | Description | Antibiotic Resistance |
|---|---|---|---|
| MG1655 PRO ΔcsgA ompR234 | FAYC002 | E. coli host strain with PRO cassette (Placi$^q$/lacI, P$_{N25}$/tetR, Spec$^R$) that constitutively expresses TetR and LacI repressors, with knock-out of endogenous csgA, and with a ompR234 allele that confers ability to produce fibrils in liquid M63 minimal media. | Kan |
| aTc$_{Receiver}$/CsgA$_{HisTag}$ | FAYC003 | E. coli strain that expresses CsgA$_{His}$ under tight regulation by an anhydrotetracycline (aTc) inducer-responsive riboregulator. Made by transforming pZA-CmR-rr12-pL(tetO)-csgA$_{HisTag}$ plasmid into MG1655 PRO ΔcsgA ompR234. | Spec, Kan, Cm |

TABLE 3-continued

Cell strains

| Strain Name | Strain ID | Description | Antibiotic Resistance |
|---|---|---|---|
| BL21(DE3) pLysS/ pDEST14-T7- Cys2-SpyCatcher | FAYC016 | E. coli strain that expresses $Cys_2$-SpyCatcher when induced by IPTG. Made by transforming pDEST14-T7-$Cys_2$-SpyCatcher into BL21(DE3) pLysS. | Cm, Amp |
| BL21(DE3) pLysS/ pET28a-T7- $Cys_2$-pilin-C | FAYC021 | E. coli strain that expresses $Cys_2$-pilin-C when induced by IPTG. Made by transforming pET28a-T7-$Cys_2$-pilin-C into BL21(DE3) pLysS. | Cm, Kan |
| $aTc_{Receiver}$/$CsgA_{SpyTag}$ | FAYC022 | E. coli strain that expresses $CsgA_{SpyTag}$ under tight regulation by an aTc inducer-responsive riboregulator. Made by transforming pZA-CmR-rr12-pL(tetO)-$csgA_{SpyTag}$ into MG1655 PRO ΔcsgA ompR234. | Spec, Kan, Cm |
| $aTc_{Receiver}$/$CsgA_{isopeptag}$ | FAYC023 | E. coli strain that expresses $CsgA_{isopeptag}$ under tight regulation by an aTc inducer-responsive riboregulator. Made by transforming pZA-CmR-rr12-pL(tetO)-$csgA_{isopeptag}$ into MG1655 PRO ΔcsgA ompR234. | Spec, Kan, Cm |

The indefinite articles "a" and "an," as used herein in the specification and in the claims, unless clearly indicated to the contrary, should be understood to mean "at least one."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements).

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements).

It should also be understood that, unless clearly indicated to the contrary, in any methods claimed herein that include more than one step or act, the order of the steps or acts of the method is not necessarily limited to the order in which the steps or acts of the method are recited.

All references (e.g., published journal articles, books, etc.), patents and patent applications disclosed herein are incorporated by reference with respect to the subject matter for which each is cited, which, in some cases, may encompass the entirety of the document.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

REFERENCES

1. Alivisatos, A. P. et al. Organization of 'nanocrystal molecules' using DNA. *Nature* 382, 609-611 (1996).
2. Braun, E., Eichen, Y., Sivan, U. & Ben-Yoseph, G. DNA-templated assembly and electrode attachment of a conducting silver wire. *Nature,* 391, 775-778 (1998).
3. Fu, A. H. et al. Discrete nanostructures of quantum dots/Au with DNA. *J. Am. Chem. Soc.* 126, 10832-10833 (2004).
4. Sharma, J. et al. Control of Self-Assembly of DNA Tubules Through Integration of Gold Nanoparticles. *Science* 323, 112-116 (2009).
5. Wang, T. et al. Self-Assembled Colloidal Superparticles from Nanorods. *Science* 338, 358-363 (2012).
6. Groschel, A. H. et al. Guided hierarchical co-assembly of soft patchy nanoparticles. *Nature* 503, 247-251 (2013).
7. Pinheiro, A. V., Han, D. R., Shih, W. M. & Yan, H. Challenges and opportunities for structural DNA nanotechnology. *Nature Nanotech.* 6, 763-772 (2011).
8. Liu, N., Hentschel, M., Weiss, T., Alivisatos, A. P. & Giessen, H. Three-Dimensional Plasmon Rulers. *Science* 332, 1407-1410 (2011).
9. Schreiber, R. et al. Hierarchical assembly of metal nanoparticles, quantum dots and organic dyes using DNA origami scaffolds. *Nature Nanotech.* 9, 74-78 (2014).
10. Zhang, Y. G., Lu, F., Yager, K. G., van der Lelie, D. & Gang, O. A general strategy for the DNA-mediated self-assembly of functional nanoparticles into heterogeneous systems. *Nature Nanotech.* 8, 865-872 (2013).
11. Walker, D. A., Leitsch, E. K., Nap, R. J., Szleifer, I. & Grzybowski, B. A. Geometric curvature controls the chemical patchiness and self-assembly of nanoparticles. *Nature Nanotech.* 8, 676-681 (2013).
12. Kostiainen, M. A. et al. Electrostatic assembly of binary nanoparticle superlattices using protein cages. *Nature Nanotech.* 8, 52-56 (2013).
13. Kuzyk, A. et al. DNA-based self-assembly of chiral plasmonic nanostructures with tailored optical response. *Nature* 483, 311-314 (2012).
14. Gao, B., Arya, G. & Tao, A. R. Self-orienting nanocubes for the assembly of plasmonic nanojunctions. *Nature Nanotech.* 7, 433-437 (2012).
15. Tikhomirov, G. et al. DNA-based programming of quantum dot valency, self-assembly and luminescence. *Nature Nanotech.* 6, 485-490 (2011).
16. Malkoch, M. et al. Self-assembled arrays of dendrimer-gold-nanoparticle hybrids for functional cell studies *Angew. Chem., Int. Ed.* 50, 3450-3453 (2011).
17. Hung, A. M. et al. Large-area spatially ordered arrays of gold nanoparticles directed by lithographically confined DNA origami. *Nature Nanotech.* 5, 121-126 (2010).
18. Nie, Z. H., Fava, D., Kumacheva, E., Zou, S., Walker, G. C. & Rubinstein, M. Self-assembly of metal-polymer analogues of amphiphilic triblock copolymers. *Nature Mater.* 6, 609-614 (2007).
19. Fu, X. et. al. Assemblies of Metal Nanoparticles and Self-Assembled Peptide Fibrils-Formation of Double Helical and Single-Chain Arrays of Metal Nanoparticles. *Adv. Mater.* 15, 902-906 (2003).
20. Djalali, R., Chen, Y. F. & Matsui, H. Au Nanowire Fabrication from Sequenced Histidine-Rich Peptide. *J. Am. Chem. Soc.* 124, 13660-13661 (2002).
21. Deng, Z. T., Pal, S., Samanta, A., Yan, H. & Liu, Y. DNA functionalization of colloidal II-VI semiconductor nanowires for multiplex nanoheterostructures. *Chem. Sci.* 4, 2234-2240 (2013).
22. Scheibel, T. et al. Conducting nanowires built by controlled self-assembly of amyloid fibers and selective metal deposition. *Proc. Natl. Acad. Sci. USA* 100, 4527-4532 (2003).
23. Dong, J. J., Castro, C. E., Boyce, M. C., Lang, M. J. & Lindquist, S. Optical trapping with high forces reveals unexpected behaviors of prion fibrils. *Nat. Struct. Mol. Biol.* 17, 1422-U1449 (2010).
24. Knowles, T. P. J. & Buehler, M. J. Nanomechanics of functional and pathological amyloid materials. *Nature Nanotech.* 6, 469-479 (2011).
25. Smith, J. F., Knowles, T. P. J., Dobson, C. M., MacPhee, C. E. & Welland, M. E. Characterization of the nanoscale properties of individual amyloid fibrils. *Proc. Natl. Acad. Sci. USA* 103, 15806-15811 (2006).
26. Zakeri, B. et al. Peptide tag forming a rapid covalent bond to a protein, through engineering a bacterial adhesin. *Proc. Natl. Acad. Sci. USA* 109, E690-E697 (2012).
27. Zhang, W. B., Sun, F., Tirrell, D. A. & Arnold, F. H., Controlling Macromolecular Topology with Genetically Encoded SpyTag-SpyCatcher Chemistry. *J. Am. Chem. Soc.* 135, 13988-13997 (2013).
28. Zakeri, B. & Howarth, M. Spontaneous Intermolecular Amide Bond Formation between Side Chains for Irreversible Peptide Targeting. *J. Am. Chem. Soc.* 132, 4526-4527 (2010).
29. Michalet, X. et al. Quantum dots for live cells, in vivo imaging, and diagnostics. *Science* 307, 538-544 (2005).
30. Medintz, I. L., Uyeda, H. T., Goldman, E. R. & Mattoussi, H. Quantum dot bioconjugates for imaging, labelling and sensing. *Nature Mater.* 4, 435-446 (2005).
31. Choi, C. L. & Alivisatos, A. P. From Artificial Atoms to Nanocrystal Molecules: Preparation and Properties of More Complex Nanostructures. *Annu. Rev. Phys. Chem.* 61, 369-389 (2010).
32. Larson, D. R. et al. Water-soluble quantum dots for multiphoton fluorescence imaging in vivo. *Science* 300, 1434-1436 (2003).
33. Sapsford, K. E. et al. Functionalizing Nanoparticles with Biological Molecules: Developing Chemistries that Facilitate Nanotechnology. *Chem. Rev.* 113, 1904-2074 (2013).
34. Qian, J. et al. Imaging pancreatic cancer using surface-functionalized quantum dots. *J. Phys. Chem. B* 111, 6969-6972 (2007).
35. Chan, W. C. W. & Nie, S. M. Quantum dot bioconjugates for ultrasensitive nonisotopic detection. *Science* 281, 2016-2018 (1998).
36. Bruchez, M., Moronne, M., Gin, P., Weiss, S. & Alivisatos, A. P. Semiconductor nanocrystals as fluorescent biological labels. *Science* 281, 2013-2016 (1998).
37. Song, F. Y. & Chan, W. C. W. Principles of conjugating quantum dots to proteins via carbodiimide chemistry. *Nanotechnology* 22 (2011).
38. Deng, Z. T., Samanta, A., Nangreave, J., Yan, H. & Liu, Y. Robust DNA-Functionalized Core/Shell Quantum Dots with Fluorescent Emission Spanning from UV-vis to Near-IR and Compatible with DNA-Directed Self-Assembly. *J. Am. Chem. Soc.* 134, 17424-17427 (2012).
39. Bui, H. et al. Programmable Periodicity of Quantum Dot Arrays with DNA Origami Nanotubes. *Nano Lett.* 10, 3367-3372 (2010).
40. Smith, A. M. & Nie, S. M. Semiconductor Nanocrystals: Structure, Properties, and Band Gap Engineering. *Acc. Chem. Res.* 43, 190-200 (2010).
41. Deng, Z. T. et al. Aqueous Synthesis of Zinc Blende CdTe/CdS Magic-Core/Thick-Shell Tetrahedral-Shaped Nanocrystals with Emission Tunable to Near-Infrared. *J. Am. Chem. Soc.* 132, 5592-5593 (2010).
42. Smith, A. M., Mohs, A. M. & Nie, S. Tuning the optical and electronic properties of colloidal nanocrystals by lattice strain. *Nature Nanotech.* 4, 56-63 (2009).
43. Chapman, M. R. et al. Role of *Escherichia coli* curli operons in directing amyloid fiber formation. *Science* 295, 851-855 (2002).
44. Chen, A. Y. et al. Synthesizing and patterning tunable multiscale materials with engineered cells. *Nature Mater.* in review (2014).
45. Payne, S., Li, B., Cao, Y., Schaeffer, D., Ryser, M. D. & You, L. C. Temporal control of self-organized pattern formation without morphogen gradients in bacteria. *Mol. Syst. Biol.* 9, 697 (2013).
46. Gübeli, R. J., Burger, K. & Weber, W. Synthetic biology for mammalian cell technology and materials sciences. *Biotechnol Adv.* 31, 68-78 (2013).
47. King, N. P. et al. Computational design of self-assembling protein nanomaterials with atomic level accuracy. *Science* 336, 1171-1174 (2012).
48. Fletcher, J. M. et al. Self-assembling cages from coiled-coil peptide modules. *Science* 340, 595-599 (2013).
49. Callura, J. M., Cantor, C. R. & Collins, J. J. Genetic switchboard for synthetic biology applications. *Proc. Natl. Acad. Sci. USA* 109, 5850-5855 (2012).
50. Lutz, R. & Bujard, H. Independent and tight regulation of transcriptional units in *Escherichia coli* via the LacR/O, the TetR/O and AraC/I1-I2 regulatory elements. *Nucleic Acids Res.* 25, 1203-1210 (1997).
51. Prigent-Combaret, C. et al. Complex regulatory network controls initial adhesion and biofilm formation in *Escherichia coli* via regulation of the csgD gene. *J Bacteriol.* 183, 7213-7223 (2001).

What is claimed is:

1. A composition comprising:
   (a) a first plurality of conjugates, wherein each conjugate of the first plurality comprises a nanoparticle linked to a first polypeptide; and
   (b) a second plurality of conjugates, wherein each conjugate of the second plurality comprises an amyloid fibril subunit linked to a second polypeptide that is heterologous to the amyloid fibril subunit,
   wherein each conjugate of the first plurality irreversibly binds to a conjugate of the second plurality through an isopeptide bond between the first and second polypeptides; and
   wherein the amyloid fibril subunits assemble to form an amyloid fibril.

2. The composition of claim 1, wherein the at least one nanoparticle comprises at least one material selected from a metal, a noble metal, an oxide, a semiconductor material, or a combination of two or more of the foregoing.

3. The composition of claim 2, wherein the composition comprises at least one semiconductor material selected from cadmium sulfide (CdS), cadmium selenide (CdSe), cadmium telluride (CdTe), zinc sulfide (ZnS), zinc selenide (ZnSe), indium phosphide (InP), lead sulfide (PbS), and lead selenide (PbSe).

4. The composition of claim 1, wherein the at least one nanoparticle comprises a core material and at least one shell material.

5. The composition of claim 1, wherein the nanoparticle is linked to the first polypeptide through a peptide linker.

6. The composition of claim 5, wherein the peptide linker is a dipeptide linker.

7. The composition of claim 6, wherein the dipeptide linker is a cysteine-cysteine ($Cys_2$) linker or a histidine-histidine ($His_2$) linker.

8. The composition of claim 5, wherein the peptide linker links a terminus of the first polypeptide to an external surface of the nanoparticle.

9. The composition of claim 8, wherein the peptide linker links the N-terminus of the first polypeptide to an external surface of the nanoparticle.

10. The composition of claim 1, wherein the amyloid fibril subunit is a CsgA protein subunit.

11. The composition of claim 1, wherein the amyloid fibril has a length of one micron to five microns.

12. The composition of claim 1, wherein one of the first and second polypeptides comprises a peptide tag, and the other of the first and second polypeptides comprises a protein.

13. The composition of claim 12, wherein the protein is SpyCatcher and the peptide tag is SpyTag.

14. The composition of claim 13, wherein the SpyTag comprises the sequence identified by SEQ ID NO: 8.

15. The composition of claim 12, wherein the protein is pilin-C and the peptide tag is isopeptag.

16. The composition of claim 15, wherein the isopeptag comprises the sequence identified by SEQ ID NO: 7.

* * * * *

SEQUENCE LISTING

<160> NUMBER OF SEQ ID NOS: 8

<210> SEQ ID NO 1
<211> LENGTH: 456
<212> TYPE: DNA
<213> ORGANISM: Artificial Sequence
<220> FEATURE:
<223> OTHER INFORMATION: Synthetic polynucleotide

<400> SEQUENCE: 1

| | |
|---|---|
| atgaaacttt taaaagtagc agcaattgca gcaatcgtat tctccggtag cgctctggca | 60 |
| ggtgttgttc ctcagtacgg cggcggcggt aaccacggtg gtggcggtaa taatagcggc | 120 |
| ccaaattctg agctgaacat ttaccagtac ggtggcggta actctgcact tgctctgcaa | 180 |
| actgatgccc gtaactctga cttgactatt acccagcatg gcggcggtaa tggtgcagat | 240 |
| gttggtcagg gctcagatga cagctcaatc gatctgaccc aacgtggctt cggtaacagc | 300 |
| gctactcttg atcagtggaa cggcaaaaat tctgaaatga cggttaaaca gttcggtggt | 360 |
| ggcaacggtg ctgcagttga ccagactgca tctaactcct ccgtcaacgt gactcaggtt | 420 |
| ggctttggta acaacgcgac cgctcatcag tactaa | 456 |

<210> SEQ ID NO 2
<211> LENGTH: 498
<212> TYPE: DNA
<213> ORGANISM: Artificial Sequence
<220> FEATURE:
<223> OTHER INFORMATION: Synthetic Polynucleotide

<400> SEQUENCE: 2

| | |
|---|---|
| atgaaacttt taaaagtagc agcaattgca gcaatcgtat tctccggtag cgctctggca | 60 |
| ggtgttgttc ctcagtacgg cggcggcggt aaccacggtg gtggcggtaa taatagcggc | 120 |
| ccaaatcacc atcaccatca ccaccattct gagctgaaca tttaccagta cggtggcggt | 180 |
| aactctgcac ttgctctgca aactgatgcc cgtaactctg acttgactat tacccagcat | 240 |
| ggcggcggta atggtgcaga tgttggtcag ggctcagatg acagctcaat cgatctgacc | 300 |
| caacgtggct tcggtaacag cgctactctt gatcagtgga acggcaaaaa ttctgaaatg | 360 |
| acggttaaac agttcggtgg tggcaacggt gctgcagttg accagactgc atctaactcc | 420 |
| tccgtcaacg tgactcaggt tggctttggt aacaacgcga ccgctcatca gtaccaccat | 480 |
| caccatcacc accattaa | 498 |

<210> SEQ ID NO 3
<211> LENGTH: 519
<212> TYPE: DNA
<213> ORGANISM: Artificial Sequence
<220> FEATURE:
<223> OTHER INFORMATION: Synthetic Polynucleotide

<400> SEQUENCE: 3

| | |
|---|---|
| atgaaacttt taaaagtagc agcaattgca gcaatcgtat tctccggtag cgctctggca | 60 |
| ggtgttgttc ctcagtacgg cggcggcggt aaccacggtg gtggcggtaa taatagcggc | 120 |
| ccaaattctg agctgaacat ttaccagtac ggtggcggta actctgcact tgctctgcaa | 180 |
| actgatgccc gtaactctga cttgactatt acccagcatg gcggcggtaa tggtgcagat | 240 |
| gttggtcagg gctcagatga cagctcaatc gatctgaccc aacgtggctt cggtaacagc | 300 |
| gctactcttg atcagtggaa cggcaaaaat tctgaaatga cggttaaaca gttcggtggt | 360 |
| ggcaacggtg ctgcagttga ccagactgca tctaactcct ccgtcaacgt gactcaggtt | 420 |

| ggctttggta acaacgcgac cgctcatcag tacggcgggg gctccggcgg gggctccgcg | 480 |
| cacatcgtta tggtcgatgc atataaaccc accaaataa | 519 |

<210> SEQ ID NO 4
<211> LENGTH: 528
<212> TYPE: DNA
<213> ORGANISM: Artificial Sequence
<220> FEATURE:
<223> OTHER INFORMATION: Synthetic Polynucleotide

<400> SEQUENCE: 4

| atgaaacttt taaaagtagc agcaattgca gcaatcgtat tctccggtag cgctctggca | 60 |
| ggtgttgttc ctcagtacgg cggcggcggt aaccacggtg gtggcggtaa taatagcggc | 120 |
| ccaaattctg agctgaacat ttaccagtac ggtggcggta actctgcact tgctctgcaa | 180 |
| actgatgccc gtaactctga cttgactatt acccagcatg gcggcggtaa tggtgcagat | 240 |
| gttggtcagg gctcagatga cagctcaatc gatctgaccc aacgtggctt cggtaacagc | 300 |
| gctactcttg atcagtggaa cggcaaaaat tctgaaatga cggttaaaca gttcggtggt | 360 |
| ggcaacggtg ctgcagttga ccagactgca tctaactcct ccgtcaacgt gactcaggtt | 420 |
| ggctttggta acaacgcgac cgctcatcag tacggaggtg gaagtggcgg cggaagtacc | 480 |
| gacaaagata tgactatcac cttcacgaat aaaaagacg cggaataa | 528 |

<210> SEQ ID NO 5
<211> LENGTH: 426
<212> TYPE: DNA
<213> ORGANISM: Artificial Sequence
<220> FEATURE:
<223> OTHER INFORMATION: Synthetic Polynucleotide

<400> SEQUENCE: 5

| atgtgttgtt cgtactacca tcaccatcac catcacgatt acgacatccc aacgaccgaa | 60 |
| aacctgtatt ttcagggcgc catggttgat accttatcag gtttatcaag tgagcaaggt | 120 |
| cagtccggtg atatgacaat tgaagaagat agtgctaccc atattaaatt ctcaaaacgt | 180 |
| gatgaggacg gcaaagagtt agctggtgca actatggagt tgcgtgattc atctggtaaa | 240 |
| actattagta catggatttc agatggacaa gtgaaagatt tctacctgta tccaggaaaa | 300 |
| tatacatttg tcgaaaccgc agcaccagac ggttatgagg tagcaactgc tattaccttt | 360 |
| acagttaatg agcaaggtca ggttactgta aatggcaaag caactaaagg tgacgctcat | 420 |
| atttaa | 426 |

<210> SEQ ID NO 6
<211> LENGTH: 918
<212> TYPE: DNA
<213> ORGANISM: Artificial Sequence
<220> FEATURE:
<223> OTHER INFORMATION: Synthetic Polynucleotide

<400> SEQUENCE: 6

| atgtgttgtg gcagcagcca tcatcatcat catcacagca gcggcctggt gccgcgcggc | 60 |
| agccatatgg ctacaacagt tcacggggag actgttgtaa acgagccaa actaacagtt | 120 |
| acaaaaaacc ttgatttagt taatagcaat gcattaattc aaatacaga ttttacattt | 180 |
| aaaatcgaac ctgatactac tgtcaacgaa gacggaaata gtttaaagg tgtagctttg | 240 |
| aacacaccga tgactaaagt cacttacacc aattcagata aaggtggatc aaatacgaaa | 300 |

```
actgcagaat ttgattttc agaagttact tttgaaaaac caggtgttta ttattacaaa      360
gtaactgagg agaagataga taaagttcct ggtgtttctt atgatacaac atcttacact      420
gttcaagttc atgtcttgtg gaatgaagag caacaaaaac cagtagctac ttatattgtt      480
ggttataaag aaggtagtaa ggtgccaatt cagttcaaaa atagcttaga ttctactaca      540
ttaacggtga agaaaaaagt ttcaggtacc ggtggagatc gctctaaaga ttttaattt       600 ggtctgactt taaaagcaaa tcagtattat aaggcgtcag aaaaagtcat gattgagaag      660
acaactaaag gtggtcaagc tcctgttcaa acagaggcta gtatagatca actctatcat      720
tttaccttga aagatggtga atcaatcaaa gtcacaaatc ttccagtagg tgtggattat      780
gttgtcactg aagacgatta caaatcagaa aaatatacaa ccaacgtgga agttagtcct      840
caagatggag ctgtaaaaaa tatcgcaggt aattcaactg aacaagagac atctactgat      900
aaagatatga ccatttag                                                   918

<210> SEQ ID NO 7
<211> LENGTH: 16
<212> TYPE: PRT
<213> ORGANISM: Artificial Seqeunce
<220> FEATURE:
<223> OTHER INFORMATION: Synthetic Polypeptide

<400> SEQUENCE: 7

Thr Asp Lys Asp Met Thr Ile Thr Phe Thr Asn Lys Lys Asp Ala Glu
1               5                   10                  15

<210> SEQ ID NO 8
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 8

Ala His Ile Val Met Val Asp Ala Tyr Lys Pro Thr Lys
1               5                   10
```